US012580072B2

(12) United States Patent
Shelton, IV et al.

(10) Patent No.: US 12,580,072 B2
(45) Date of Patent: Mar. 17, 2026

(54) CLOUD ANALYTICS PACKAGES

(71) Applicant: Cilag GmbH International, Zug (CH)

(72) Inventors: Frederick L. Shelton, IV, New Vienna, OH (US); Jason L. Harris, Lebanon, OH (US); Shane R. Adams, Lebanon, OH (US); Michael J. Vendely, Lebanon, OH (US); Kevin M. Fiebig, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 289 days.

(21) Appl. No.: 17/062,526

(22) Filed: Oct. 2, 2020

(65) Prior Publication Data

US 2022/0108789 A1 Apr. 7, 2022

(51) Int. Cl.
*G16H 40/20* (2018.01)
*A61B 34/10* (2016.01)
(Continued)

(52) U.S. Cl.
CPC ............. *G16H 40/20* (2018.01); *A61B 34/10* (2016.02); *G16H 10/60* (2018.01); *G16H 20/40* (2018.01);
(Continued)

(58) Field of Classification Search
CPC ......... H04L 67/12; H04L 41/0813–082; H04L 41/0866–0869
See application file for complete search history.

(56) References Cited

U.S. PATENT DOCUMENTS

| 5,754,192 A | 5/1998 | Sugaya |
| 6,451,015 B1 | 9/2002 | Rittman, III et al. |
| | (Continued) | |

FOREIGN PATENT DOCUMENTS

| CA | 3089858 A1 | 8/2019 |
| EP | 2 491 872 A1 | 8/2012 |
| | (Continued) | |

OTHER PUBLICATIONS

U.S. Appl. No. 17/062,504, filed Oct. 2, 2020, Shelton IV, et al.
(Continued)

*Primary Examiner* — Karen A Hranek
(74) *Attorney, Agent, or Firm* — Condo Roccia Koptiw LLP

(57) ABSTRACT
Examples here describe a surgical system that may include a cloud computing system, a surgical hub, and a surgical instrument. The cloud computing system may be configured to aggregate data from multiple surgical devices. The surgical hub may determine whether communication is available with the cloud computing system, may receive the aggregate data from the multiple surgical devices via the receiver, may update one or more surgical hub control algorithms based on the aggregated data received, and may continue to communicate with the cloud computing system to receive additional updates, wherein the additional updates relate to updated aggregate data determined by the cloud computing system. The surgical instrument may determine whether communication is available with the cloud computing system and with the surgical hub and may receive the aggregate data relating to the multiple surgical devices from the cloud computing system or the surgical hub via the receiver.

20 Claims, 36 Drawing Sheets

(51) Int. Cl.

| | |
|---|---|
| *G16H 10/60* | (2018.01) |
| *G16H 20/40* | (2018.01) |
| *G16H 40/40* | (2018.01) |
| *G16H 40/67* | (2018.01) |
| *G16H 50/70* | (2018.01) |
| *G16H 70/20* | (2018.01) |
| *H04B 1/02* | (2006.01) |
| *H04B 1/06* | (2006.01) |
| *H04L 67/12* | (2022.01) |
| *G16H 15/00* | (2018.01) |

(52) U.S. Cl.

CPC ............. *G16H 40/40* (2018.01); *G16H 40/67* (2018.01); *G16H 50/70* (2018.01); *G16H 70/20* (2018.01); *H04B 1/02* (2013.01); *H04B 1/06* (2013.01); *H04L 67/12* (2013.01); *G16H 15/00* (2018.01)

(56) References Cited

U.S. PATENT DOCUMENTS

| | | | |
|---|---|---|---|
| 6,847,336 | B1 | 1/2005 | Lemelson et al. |
| 7,032,798 | B2 | 4/2006 | Whitman et al. |
| 7,164,940 | B2 | 1/2007 | Hareyama et al. |
| 7,496,395 | B2 | 2/2009 | Serov et al. |
| 7,667,592 | B2 | 2/2010 | Ohyama et al. |
| 7,670,334 | B2 | 3/2010 | Hueil et al. |
| 7,803,151 | B2 | 9/2010 | Whitman |
| 7,833,219 | B2 | 11/2010 | Tashiro et al. |
| 7,839,354 | B2 | 11/2010 | Moriwaki |
| 8,157,145 | B2 | 4/2012 | Shelton, IV et al. |
| 8,255,045 | B2 | 8/2012 | Gharib et al. |
| 8,476,227 | B2 | 7/2013 | Kaplan et al. |
| 8,523,043 | B2 | 9/2013 | Ullrich et al. |
| 8,608,045 | B2 | 12/2013 | Smith et al. |
| 8,851,354 | B2 | 10/2014 | Swensgard et al. |
| 8,918,207 | B2 | 12/2014 | Prisco |
| 8,960,519 | B2 | 2/2015 | Whitman et al. |
| 9,011,427 | B2 | 4/2015 | Price et al. |
| 9,072,535 | B2 | 7/2015 | Shelton, IV et al. |
| 9,123,155 | B2 | 9/2015 | Cunningham et al. |
| 9,250,172 | B2 | 2/2016 | Harris |
| 9,283,054 | B2 | 3/2016 | Morgan et al. |
| 9,345,481 | B2 | 5/2016 | Hall et al. |
| 9,516,239 | B2 | 12/2016 | Blanquart et al. |
| 9,538,962 | B1 | 1/2017 | Hannaford et al. |
| 9,582,055 | B2 | 2/2017 | De Jong et al. |
| 9,743,016 | B2 | 8/2017 | Nestares et al. |
| 9,777,913 | B2 | 10/2017 | Talbert et al. |
| 9,913,642 | B2 | 3/2018 | Leimbach et al. |
| 10,492,783 | B2 | 12/2019 | Shelton, IV et al. |
| 10,639,037 | B2 | 5/2020 | Shelton, IV et al. |
| 10,695,081 | B2 | 6/2020 | Shelton, IV et al. |
| 10,881,399 | B2 | 1/2021 | Shelton et al. |
| 10,912,567 | B2 | 2/2021 | Shelton, IV et al. |
| 10,987,178 | B2 | 4/2021 | Shelton, IV et al. |
| 11,123,074 | B2 | 9/2021 | Adams et al. |
| 11,185,331 | B2 | 11/2021 | Adams et al. |
| 11,284,963 | B2 | 3/2022 | Shelton, IV et al. |
| 2004/0108825 | A1 | 6/2004 | Lee et al. |
| 2005/0033117 | A1 | 2/2005 | Ozaki et al. |
| 2005/0128184 | A1 | 6/2005 | Mcgreevy |
| 2005/0134525 | A1 | 6/2005 | Tanghe et al. |
| 2005/0206583 | A1 | 9/2005 | Lemelson et al. |
| 2006/0004286 | A1 | 1/2006 | Chang et al. |
| 2006/0076385 | A1 | 4/2006 | Etter et al. |
| 2006/0082542 | A1 | 4/2006 | Morita et al. |
| 2006/0184160 | A1 | 8/2006 | Ozaki et al. |
| 2006/0273135 | A1 | 12/2006 | Beetel |
| 2007/0013336 | A1 | 1/2007 | Nowlin et al. |
| 2007/0055304 | A1 | 3/2007 | Whitman |
| 2007/0151390 | A1 | 7/2007 | Blumenkranz et al. |
| 2007/0173689 | A1 | 7/2007 | Ozaki et al. |
| 2007/0225690 | A1 | 9/2007 | Sekiguchi et al. |
| 2007/0255348 | A1* | 11/2007 | Holtzclaw .............. G16H 40/67 607/60 |
| 2008/0319275 | A1 | 12/2008 | Chiu et al. |
| 2009/0036750 | A1* | 2/2009 | Weinstein .............. G16H 40/67 600/300 |
| 2009/0046146 | A1 | 2/2009 | Hoyt |
| 2009/0090763 | A1 | 4/2009 | Zemlok et al. |
| 2009/0128084 | A1 | 5/2009 | Johnson et al. |
| 2009/0248022 | A1 | 10/2009 | Falkenstein et al. |
| 2010/0096431 | A1 | 4/2010 | Smith et al. |
| 2011/0181394 | A1 | 7/2011 | Blair |
| 2012/0069131 | A1 | 3/2012 | Abelow |
| 2012/0116365 | A1 | 5/2012 | Price et al. |
| 2012/0138658 | A1 | 6/2012 | Ullrich et al. |
| 2012/0182409 | A1 | 7/2012 | Moriyama et al. |
| 2012/0211542 | A1 | 8/2012 | Racenet |
| 2012/0248167 | A1 | 10/2012 | Flanagan et al. |
| 2012/0253329 | A1 | 10/2012 | Zemlok et al. |
| 2013/0116218 | A1 | 5/2013 | Kaplan et al. |
| 2013/0197531 | A1 | 8/2013 | Boukhny et al. |
| 2013/0245456 | A1 | 9/2013 | Ferguson, Jr. et al. |
| 2014/0018637 | A1* | 1/2014 | Bennett .............. H04L 43/0817 607/51 |
| 2014/0066700 | A1 | 3/2014 | Wilson et al. |
| 2014/0087999 | A1 | 3/2014 | Myers et al. |
| 2014/0160002 | A1 | 6/2014 | Dent |
| 2014/0160259 | A1 | 6/2014 | Blanquart et al. |
| 2014/0160260 | A1 | 6/2014 | Blanquart et al. |
| 2014/0160318 | A1 | 6/2014 | Blanquart et al. |
| 2014/0160319 | A1 | 6/2014 | Nestares et al. |
| 2014/0166728 | A1 | 6/2014 | Swayze et al. |
| 2014/0201126 | A1 | 7/2014 | Zadeh et al. |
| 2014/0214311 | A1 | 7/2014 | Stevens et al. |
| 2014/0263541 | A1 | 9/2014 | Leimbach et al. |
| 2014/0263551 | A1 | 9/2014 | Hall et al. |
| 2014/0263552 | A1 | 9/2014 | Hall et al. |
| 2014/0267655 | A1 | 9/2014 | Richardson et al. |
| 2014/0268860 | A1 | 9/2014 | Talbert et al. |
| 2015/0125447 | A1 | 5/2015 | Heider |
| 2015/0157416 | A1 | 6/2015 | Andersson |
| 2015/0181629 | A1* | 6/2015 | Jun ........................ A61B 6/468 455/420 |
| 2015/0182220 | A1 | 7/2015 | Yates et al. |
| 2015/0223890 | A1 | 8/2015 | Miller et al. |
| 2015/0342621 | A1 | 12/2015 | Jackson, III |
| 2016/0045661 | A1* | 2/2016 | Gray ....................... A61M 5/142 604/67 |
| 2016/0066915 | A1 | 3/2016 | Baber et al. |
| 2016/0066916 | A1 | 3/2016 | Overmyer et al. |
| 2016/0100839 | A1 | 4/2016 | Marczyk et al. |
| 2016/0148052 | A1 | 5/2016 | Tsuda et al. |
| 2016/0154620 | A1 | 6/2016 | Tsuda et al. |
| 2016/0171330 | A1 | 6/2016 | Mentese et al. |
| 2016/0171947 | A1 | 6/2016 | Chen |
| 2016/0249919 | A1 | 9/2016 | Savage et al. |
| 2016/0253472 | A1* | 9/2016 | Pedersen .............. A61B 5/0013 705/2 |
| 2016/0256156 | A1 | 9/2016 | Shelton, IV et al. |
| 2016/0256184 | A1 | 9/2016 | Shelton, IV et al. |
| 2016/0265938 | A1 | 9/2016 | Hryb et al. |
| 2016/0332296 | A1 | 11/2016 | Kurnianto |
| 2017/0000551 | A1 | 1/2017 | Ward et al. |
| 2017/0000575 | A1 | 1/2017 | Griffiths et al. |
| 2017/0086914 | A1 | 3/2017 | Wiener et al. |
| 2017/0105706 | A1 | 4/2017 | Berger et al. |
| 2017/0172381 | A1 | 6/2017 | Morimoto |
| 2017/0199632 | A1 | 7/2017 | Ohmura |
| 2017/0220769 | A1* | 8/2017 | Miller ................ G06Q 30/0601 |
| 2017/0227754 | A1 | 8/2017 | Huang |
| 2017/0249431 | A1 | 8/2017 | Shelton, IV et al. |
| 2017/0272838 | A1 | 9/2017 | Glazer et al. |
| 2017/0296169 | A1 | 10/2017 | Yates et al. |
| 2017/0296178 | A1 | 10/2017 | Miller et al. |
| 2017/0296213 | A1 | 10/2017 | Swensgard et al. |
| 2017/0323062 | A1 | 11/2017 | Djajadiningrat et al. |
| 2017/0333033 | A1 | 11/2017 | Valentine et al. |
| 2018/0032130 | A1 | 2/2018 | Meglan |
| 2018/0098049 | A1 | 4/2018 | Sugano et al. |
| 2018/0098768 | A1 | 4/2018 | Zhang et al. |

(56) References Cited

U.S. PATENT DOCUMENTS

| | | |
|---|---|---|
| 2018/0165051 A1 | 6/2018 | Kim et al. |
| 2018/0197624 A1 | 7/2018 | Robaina et al. |
| 2018/0214009 A1 | 8/2018 | Endo |
| 2018/0256025 A1 | 9/2018 | Yi et al. |
| 2018/0329504 A1 | 11/2018 | Ziraknejad et al. |
| 2018/0353186 A1 | 12/2018 | Mozdzierz et al. |
| 2018/0360449 A1 | 12/2018 | Shelton, IV et al. |
| 2018/0360452 A1 | 12/2018 | Shelton, IV et al. |
| 2018/0360460 A1 | 12/2018 | Mozdzierz et al. |
| 2019/0000446 A1 | 1/2019 | Shelton, IV et al. |
| 2019/0000464 A1 | 1/2019 | Shelton, IV et al. |
| 2019/0000478 A1 | 1/2019 | Messerly et al. |
| 2019/0020420 A1 | 1/2019 | Zocher et al. |
| 2019/0099180 A1 | 4/2019 | Leimbach et al. |
| 2019/0104919 A1 | 4/2019 | Shelton, IV et al. |
| 2019/0117070 A1 | 4/2019 | Muhsin et al. |
| 2019/0123978 A1* | 4/2019 | Shaw ...................... H04W 4/24 |
| 2019/0125361 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0183591 A1 | 6/2019 | Johnson et al. |
| 2019/0200844 A1 | 7/2019 | Shelton et al. |
| 2019/0200905 A1 | 7/2019 | Shelton, IV et al. |
| 2019/0200906 A1 | 7/2019 | Shelton, IV et al. |
| 2019/0200981 A1 | 7/2019 | Harris et al. |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton et al. |
| 2019/0201029 A1 | 7/2019 | Shelton, IV et al. |
| 2019/0201033 A1* | 7/2019 | Yates .................... G16H 40/63 |
| 2019/0201034 A1 | 7/2019 | Shelton, IV et al. |
| 2019/0201044 A1 | 7/2019 | Shelton et al. |
| 2019/0201102 A1 | 7/2019 | Shelton, IV et al. |
| 2019/0201104 A1 | 7/2019 | Shelton, IV et al. |
| 2019/0201115 A1 | 7/2019 | Shelton, IV et al. |
| 2019/0201119 A1 | 7/2019 | Harris et al. |
| 2019/0201122 A1 | 7/2019 | Shelton, IV et al. |
| 2019/0201129 A1 | 7/2019 | Shelton, IV et al. |
| 2019/0201136 A1 | 7/2019 | Shelton et al. |
| 2019/0201137 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201144 A1 | 7/2019 | Shelton, IV et al. |
| 2019/0201146 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0206003 A1 | 7/2019 | Harris et al. |
| 2019/0206050 A1 | 7/2019 | Yates et al. |
| 2019/0206555 A1 | 7/2019 | Morgan et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton et al. |
| 2019/0206565 A1 | 7/2019 | Shelton, IV |
| 2019/0206569 A1* | 7/2019 | Shelton, IV ........... A61B 34/71 |
| 2019/0250873 A1 | 8/2019 | Blume et al. |
| 2019/0314015 A1 | 10/2019 | Shelton, IV et al. |
| 2019/0388137 A1 | 12/2019 | Henrywood |
| 2020/0030044 A1 | 1/2020 | Wang et al. |
| 2020/0046208 A1 | 2/2020 | Kasai et al. |
| 2020/0078078 A1 | 3/2020 | Henderson et al. |
| 2020/0078079 A1 | 3/2020 | Morgan et al. |
| 2020/0090412 A1 | 3/2020 | Harviainen |
| 2020/0120308 A1 | 4/2020 | Mcmillan et al. |
| 2020/0162664 A1 | 5/2020 | Maeda et al. |
| 2020/0188057 A1 | 6/2020 | Brandao et al. |
| 2020/0214571 A1 | 7/2020 | Bradbury et al. |
| 2020/0219319 A1 | 7/2020 | Lashmar et al. |
| 2020/0281790 A1 | 9/2020 | Augustine et al. |
| 2020/0342228 A1 | 10/2020 | Prevrhal et al. |
| 2020/0350063 A1 | 11/2020 | Thornton et al. |
| 2020/0356255 A1 | 11/2020 | Qing et al. |
| 2020/0405304 A1 | 12/2020 | Mozdzierz et al. |
| 2020/0405439 A1 | 12/2020 | Shelton, IV et al. |
| 2021/0007574 A1* | 1/2021 | Hirayama ........... A61B 1/0661 |
| 2021/0015461 A1 | 1/2021 | Karasawa |
| 2021/0060243 A1* | 3/2021 | Dave ..................... G01D 5/145 |
| 2021/0077110 A1 | 3/2021 | Adams et al. |
| 2021/0077111 A1 | 3/2021 | Adams et al. |
| 2021/0077112 A1 | 3/2021 | Adams et al. |
| 2021/0092007 A1* | 3/2021 | Danilchenko ....... H04L 41/0895 |
| 2021/0113269 A1 | 4/2021 | Vilsmeier et al. |
| 2021/0137581 A1 | 5/2021 | Reid et al. |
| 2021/0169578 A1 | 6/2021 | Calloway et al. |
| 2021/0196384 A1 | 7/2021 | Shelton, IV et al. |
| 2021/0196423 A1 | 7/2021 | Shelton, IV et al. |
| 2021/0196425 A1 | 7/2021 | Shelton, IV et al. |
| 2021/0205027 A1 | 7/2021 | Leist |
| 2021/0240279 A1 | 8/2021 | Harviainen et al. |
| 2021/0307833 A1 | 10/2021 | Farley et al. |
| 2021/0375439 A1* | 12/2021 | Mckinnon .............. A61B 34/20 |
| 2021/0401533 A1 | 12/2021 | Im |
| 2022/0022982 A1 | 1/2022 | Hares et al. |
| 2022/0025258 A1 | 1/2022 | Ichikawa et al. |
| 2022/0104694 A1 | 4/2022 | Shelton, IV et al. |
| 2022/0104713 A1 | 4/2022 | Shelton, IV |
| 2022/0104765 A1 | 4/2022 | Shelton, IV et al. |
| 2022/0104806 A1 | 4/2022 | Shelton, IV et al. |
| 2022/0104807 A1 | 4/2022 | Shelton, IV et al. |
| 2022/0104813 A1 | 4/2022 | Shelton, IV et al. |
| 2022/0104814 A1 | 4/2022 | Shelton, IV et al. |
| 2022/0104820 A1 | 4/2022 | Shelton, IV et al. |
| 2022/0104821 A1 | 4/2022 | Shelton, IV et al. |
| 2022/0104822 A1 | 4/2022 | Shelton, IV et al. |
| 2022/0104843 A1 | 4/2022 | Shelton, IV et al. |
| 2022/0104867 A1 | 4/2022 | Shelton, IV et al. |
| 2022/0104889 A1 | 4/2022 | Shelton, IV et al. |
| 2022/0104896 A1 | 4/2022 | Shelton, IV et al. |
| 2022/0104897 A1 | 4/2022 | Shelton, IV et al. |
| 2022/0104908 A1 | 4/2022 | Shelton, IV et al. |
| 2022/0104910 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0108783 A1 | 4/2022 | Shelton, IV et al. |
| 2022/0108788 A1 | 4/2022 | Shelton, IV et al. |
| 2022/0108789 A1 | 4/2022 | Shelton, IV et al. |
| 2022/0246287 A1 | 8/2022 | Dawson et al. |
| 2024/0260966 A1 | 8/2024 | Shelton, IV et al. |

FOREIGN PATENT DOCUMENTS

| | | | |
|---|---|---|---|
| EP | 2659852 A2 | 11/2013 | |
| EP | 2 789 299 A1 | 10/2014 | |
| EP | 3061405 A1 | 8/2016 | |
| EP | 3064141 A1 | 9/2016 | |
| EP | 3336849 A1 * | 6/2018 | ............. G16H 40/60 |
| EP | 3 412 225 A1 | 12/2018 | |
| EP | 3 449 800 A1 | 3/2019 | |
| EP | 3466348 A2 | 4/2019 | |
| EP | 3 506 273 A1 | 7/2019 | |
| EP | 3506299 A1 | 7/2019 | |
| EP | 3547324 A1 | 10/2019 | |
| EP | 3628207 A1 | 4/2020 | |
| KR | 2001-0001630 A | 1/2001 | |
| WO | 00/70529 A2 | 11/2000 | |
| WO | 2008/135736 A1 | 11/2008 | |
| WO | 2015/125447 A1 | 8/2015 | |
| WO | 2016/171947 A1 | 10/2016 | |
| WO | 2019/130108 A1 | 7/2019 | |
| WO | 2019/133056 A1 | 7/2019 | |
| WO | 2020/101283 A1 | 5/2020 | |
| WO | 2020/129916 A1 | 6/2020 | |
| WO | 2020/154351 A1 | 7/2020 | |

OTHER PUBLICATIONS

"FPGA Fundamentals", Available at <https://www.ni.com/en-us/innovations/white-papers/08/fpga-fundamentals.html>, Jun. 17, 2020, pp. 1-9.

Alsos et al., "Interaction Techniques for Using Handhelds and PCs Together in a Clinical Setting", Department of Computer and Information Science, Norwegian University of Science and Technology, Oct. 14-18, 2006, pp. 125-134.

Google Scholar, "Google Scholar", 2 pages.

(56)         References Cited

OTHER PUBLICATIONS

Qamar, Rahil, "Semantic Mapping of Clinical Model Data to Biomedical Terminologies to Facilitate Interoperability", A thesis submitted to the University of Manchester, 2008, 260 pages.
Slade, G. W., "The Fast Fourier Transform in Hardware: A Tutorial Based on an FPGA Implementation", Available at <http://web.mit.edu/>, Mar. 21, 2013, 27 pages.

* cited by examiner

23000

23002

Identify hub connectivity control parameter(s) ─ 16104

Determine a hub connectivity mode based on the identified hub connectivity control parameter(s) ─ 16108

Communicate with devices and/ or network(s) in the determined hub connectivity mode ─ 16110

11500

Determine, based on the operation mode, whether to obtain a sensed parameter from a sensor — 11510

Determine, based on the operation mode, whether to receive an instrument usage instruction — 11520

Communicate with a surgical hub based on the determination via the transmitter. — 11530

CLOUD ANALYTICS PACKAGES

CROSS-REFERENCE TO RELATED APPLICATIONS

This application is related to an application filed contemporaneously, with U.S. patent application Ser. No. 17/062,504, filed Oct. 2, 2020, entitled METHOD FOR OPERATING TIERED OPERATION MODES IN A SURGICAL SYSTEM, the contents of which is incorporated by reference herein.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

A surgical hub is provided. The surgical hub comprises a transmitter and a receiver configured to establish a communication pathway between the surgical hub and a cloud computing system; and a processor. The processor is configured is determine whether communication is available with the cloud computing system that is configured to aggregate data from multiple surgical devices; receive the aggregate data from the multiple surgical devices via the receiver; update one or more control algorithms based on the aggregated data received; and continue to communicate with the cloud computing system to receive additional updates, wherein the additional updates relate to updated aggregate data determined by the cloud computing system.

A surgical instrument is provided. The surgical instrument comprises a transmitter and a receiver configured to establish a communication pathway between the surgical hub and a cloud computing system; and a processor. The processor is configured to: determine whether communication is available with the cloud computing system that is configured to aggregate data from multiple surgical devices; receive the aggregate data from the multiple surgical devices via the receiver; update one or more control algorithms based on the aggregated data received; and continue to communicate with the cloud computing system to receive additional updates, wherein the additional updates relate to updated aggregate data determined by the cloud computing system.

A surgical system is provided. The surgical system comprises a cloud computing system, a surgical hub, and a surgical instrument. The cloud computing system is configured to aggregate data from multiple surgical devices. The surgical hub comprises: a transmitter and a receiver configured to establish a communication pathway between the surgical hub and the cloud computing system and a processor. The processor is configured to: determine whether communication is available with the cloud computing system; receive the aggregate data from the multiple surgical devices via the receiver; update one or more surgical hub control algorithms based on the aggregated data received; and continue to communicate with the cloud computing system to receive additional updates, wherein the additional updates relate to updated aggregate data determined by the cloud computing system. The surgical instrument comprises a transmitter and a receiver configured to establish a communication pathway between the surgical hub and the cloud computing system and a processor. The process is configured to: determine whether communication is available with the cloud computing system and with the surgical hub; receive the aggregate data relating to the multiple surgical devices from the cloud computing system or the surgical hub via the receiver; update one or more surgical instrument control algorithms based on the aggregated data received; and continue to communicate with the cloud computing system and the surgical hub to receive additional updates, wherein the additional updates relate to updated aggregate data determined by the cloud computing system.

DETAILED DESCRIPTION

Applicant of the present application owns the following U.S. Patent Applications, filed contemporaneously, each of which is herein incorporated by reference in its entirety:

U.S. patent application Ser. No. 15/940,636, entitled "ADAPTIVE CONTROL PROGRAM UPDATES FOR SURGICAL DEVICES," filed Mar. 29, 2018, now U.S. Patent Application Publication No. 2019/0206003; and U.S. patent application Ser. No. 16/209,490, entitled "METHOD FOR FACILITY DATA COLLECTION AND INTERPRETATION," filed Dec. 4, 2018, now U.S. Patent Application Publication No. 2019/0206564.

Figure 1:
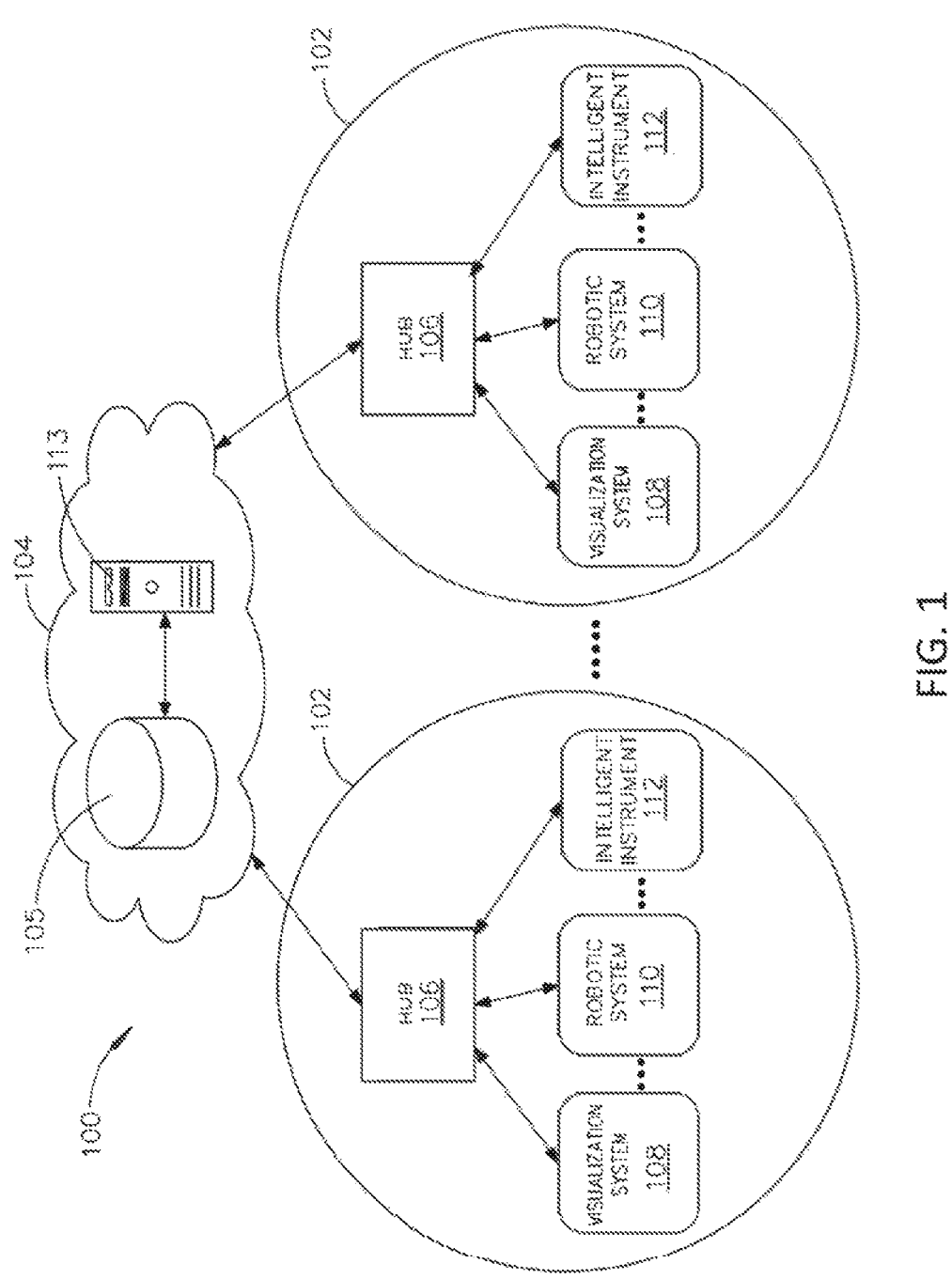
FIG. 1 is a block diagram of a computer-implemented interactive surgical system, in accordance with at least one aspect of the present disclosure.

Referring to FIG. 1, a computer-implemented interactive surgical system 100 may include one or more surgical systems 102 and a cloud-based system (e.g., the cloud 104 that may include a remote server 113 coupled to a storage device 105). Each surgical system 102 may include at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P may be integers greater than or equal to one.

Figure 2:
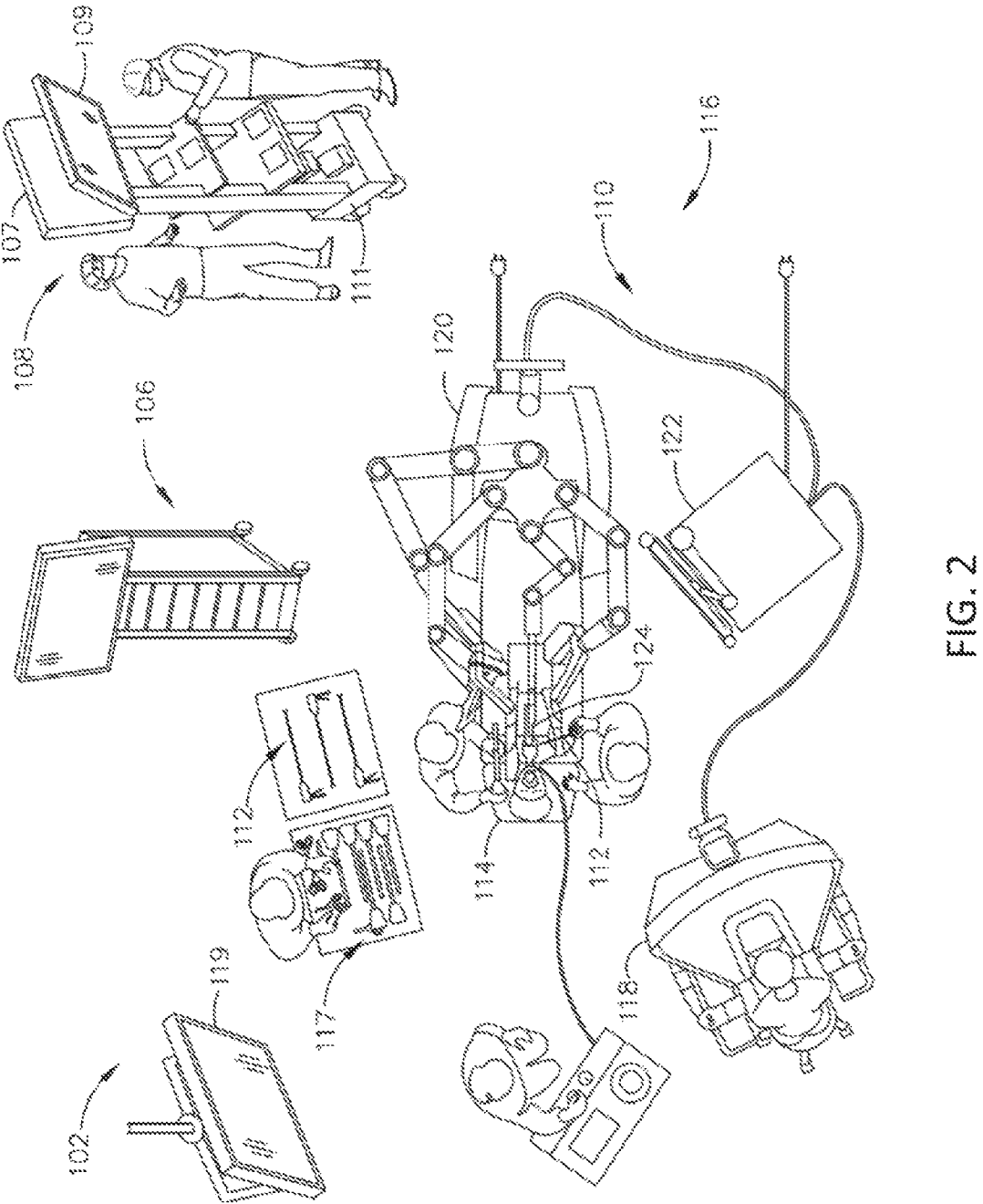
FIG. 2 is a surgical system being used to perform a surgical procedure in an operating room, in accordance with at least one aspect of the present disclosure.

In various aspects, the visualization system 108 may include one or more imaging sensors, one or more image-processing units, one or more storage arrays, and one or more displays that are strategically arranged with respect to the sterile field, as illustrated in FIG. 2. In one aspect, the visualization system 108 may include an interface for HL7, PACS, and EMR. Various components of the visualization system 108 are described under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 may include a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 may also be configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 may also be configured to coordinate information flow to a display of the surgical instrument 112. For example, in U.S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 depicts an example of a surgical system 102 being used to perform a surgical procedure on a patient who is lying down on an operating table 114 in a surgical operating room 116. A robotic system 110 may be used in the surgical procedure as a part of the surgical system 102. The robotic system 110 may include a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud 104, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 124 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209, 385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 3:
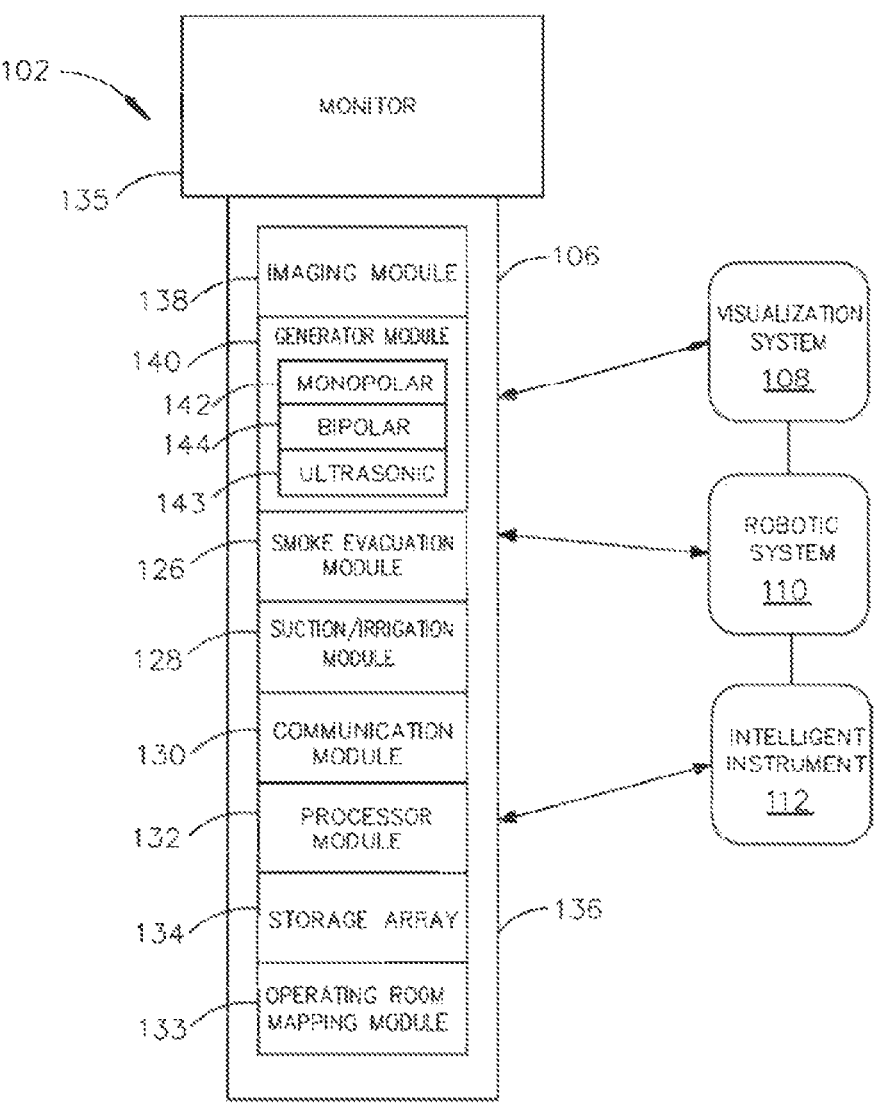
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, a storage array 134, and an operating-room mapping module 133. In certain aspects, as illustrated in FIG. 3, the hub 106 further includes a smoke evacuation module 126 and/or a suction/irrigation module 128. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines. Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line is a first fluid line and a second fluid line extends from the remote surgical site to a suction and irrigation module slidably received in the hub enclosure. In one aspect, the hub enclosure comprises a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module con-figured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate com-munication between the first energy-generator module and the second energy-generator module. Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 146. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

Figure 4:
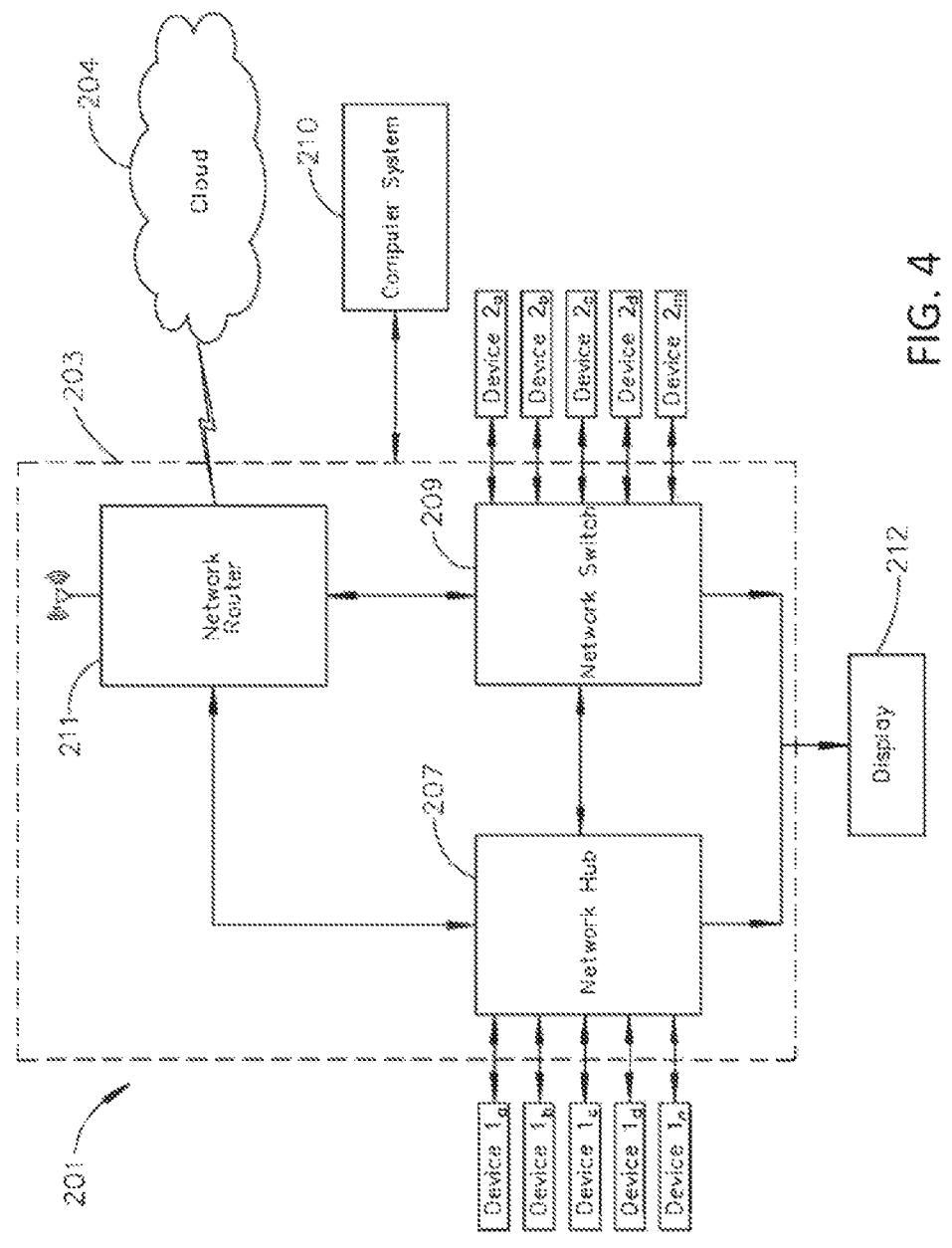
FIG. 4 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 4 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

The operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub may provide connectivity to the devices 1a-1n located in the same operating theater network. The network hub 207 may collect data in the form of packets and sends them to the router in half duplex mode. The network hub 207 may not store any media access control/Internet Protocol (MAC/IP) to transfer the device data. Only one of the devices 1a-1n can send data at a time through the network hub 207. The network hub 207 may not have routing tables or intelligence regarding where to send information and broadcasts all network data across each connection and to a remote server 213 (FIG. 4) over the cloud 204. The network hub 207 can detect basic network errors such as collisions, but having all information broadcast to multiple ports can be a security risk and cause bottlenecks.

The operating theater devices 2a-2m may be connected to a network switch 209 over a wired channel or a wireless channel. The network switch 209 works in the data link layer of the OSI model. The network switch 209 may be a multicast device for connecting the devices 2a-2m located in the same operating theater to the network. The network switch 209 may send data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 may be coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 may send data in the form of packets to the cloud 204 and works in full duplex mode. Multiple devices can send data at the same time. The network router 211 uses IP addresses to transfer data.

In an example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHZ) from fixed and mobile devices and building personal area networks (PANs). The the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and may handle a data type known as frames. Frames may carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 can be generally easy to install, configure, and maintain, making it a good option for networking the operating theater devices 1a-1n/2a-2m.

Figure 5:
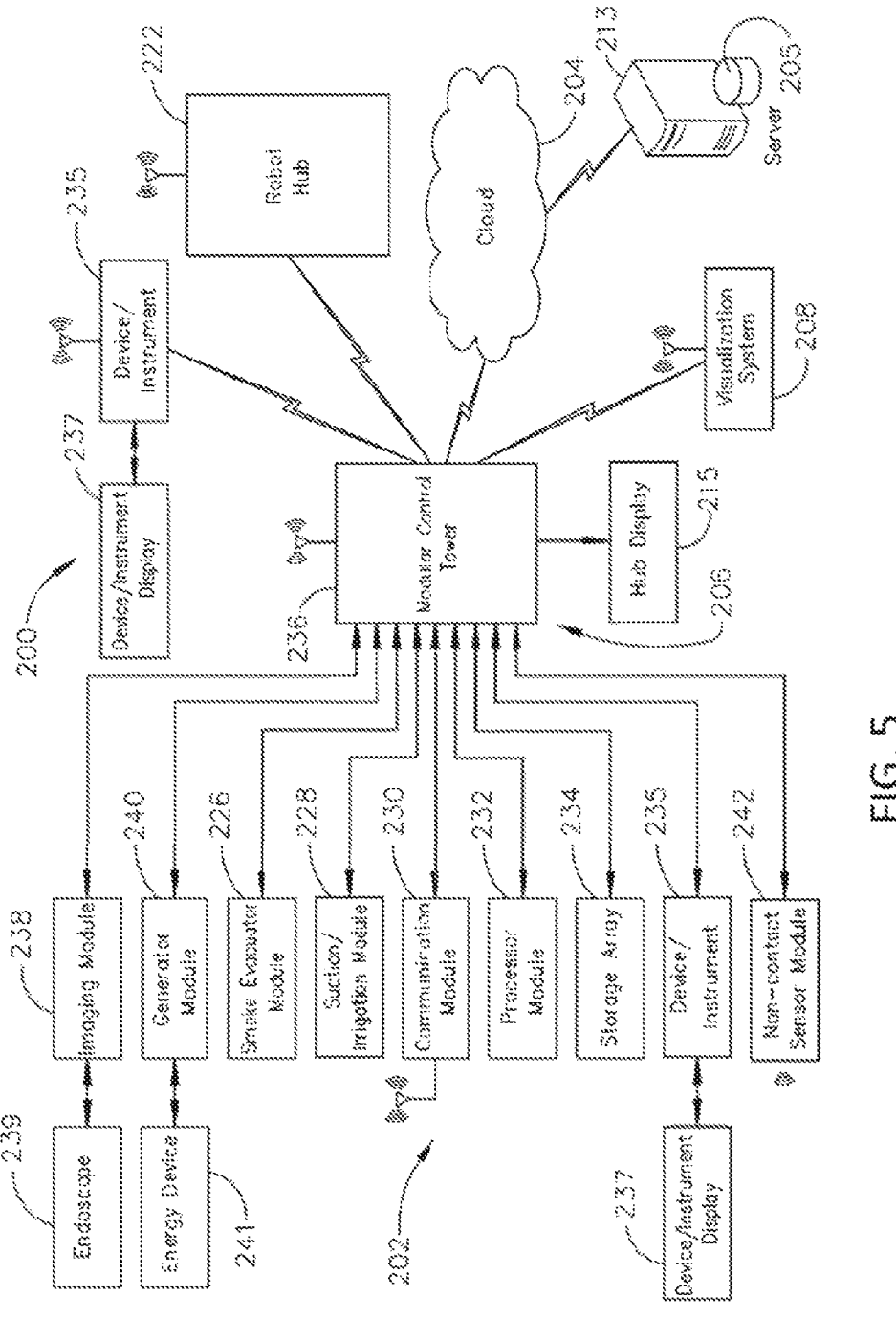
FIG. 5 illustrates a computer-implemented interactive surgical system, in accordance with at least one aspect of the present disclosure.
Figure 6:
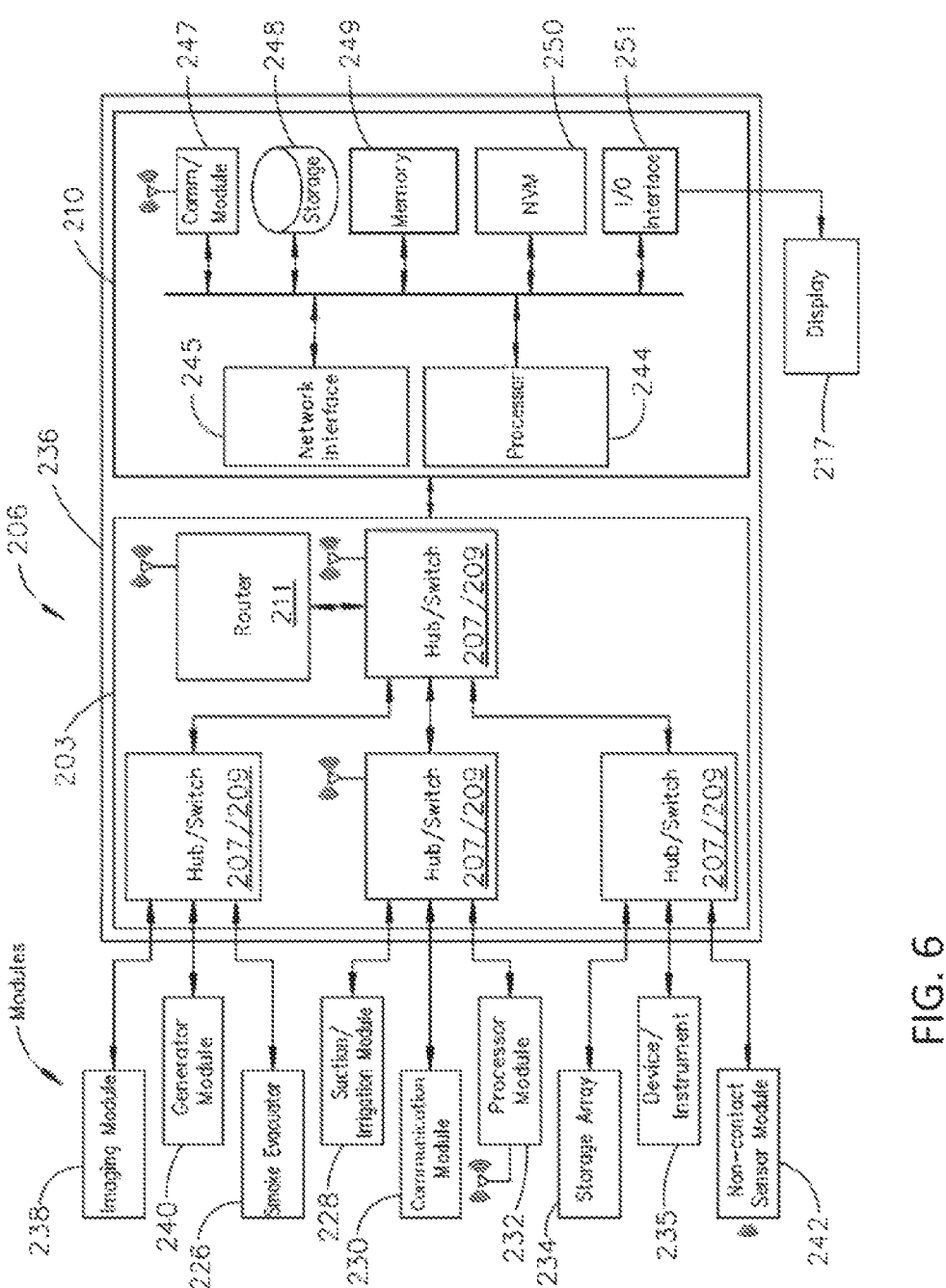
FIG. 6 illustrates a surgical hub comprising a plurality of modules coupled to the modular control tower, in accordance with at least one aspect of the present disclosure.

FIG. 5 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 6, the modular control tower 236 comprises a modular communication hub 203 coupled to a computer system 210.

As illustrated in the example of FIG. 5, the modular control tower 236 may be coupled to an imaging module 238 that may be coupled to an endoscope 239, a generator module 240 that may be coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices may be coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 6 illustrates a surgical hub 206 comprising a plurality of modules coupled to the modular control tower 236. The modular control tower 236 may comprise a modular communication hub 203, e.g., a network connectivity device, and a computer system 210 to provide local processing, visualization, and imaging, for example. As shown in FIG. 6, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 6, each of the network hubs/switches in the modular communication hub 203 may include three downstream ports and one upstream port. The upstream network hub/switch may be connected to a processor to provide a communication connection to the cloud computing resources and a local display 217. Communication to the cloud 204 may be made either through a wired or a wireless communication channel.

The surgical hub 206 may employ a non-contact sensor module 242 to measure the dimensions of the operating theater and generate a map of the surgical theater using either ultrasonic or laser-type non-contact measurement devices. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, which is herein incorporated by reference in its entirety, in which the sensor module is configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 may comprise a processor 244 and a network interface 245. The processor 244 can be coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHZ, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory may include volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also may include removable/non-removable, volatile/non-volatile computer storage media, such as for example disk storage. The disk storage can include, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 210 through input device(s) coupled to the I/O interface 251. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5 and the like. WAN technologies may include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 6, the imaging module 238 and/or visualization system 208, and/or the processor module 232 of FIGS. 5-6, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system, it can also be external to the computer system 210. The hardware/software necessary for connection to the network interface may include, for illustrative purposes only, internal and external technologies such as modems, including regular telephone-grade modems, cable modems, and DSL modems, ISDN adapters, and Ethernet cards.

Figure 7:
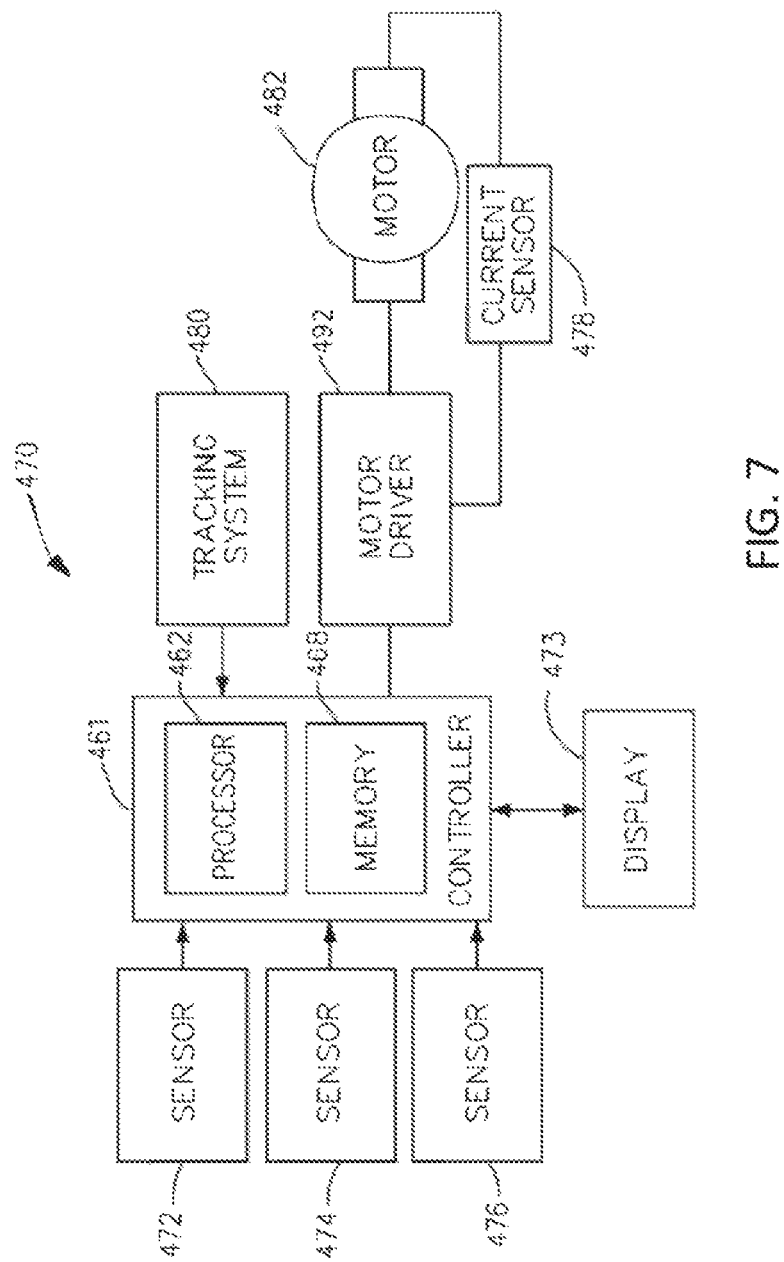
FIG. 7 illustrates a logic diagram of a control system of a surgical instrument or tool, in accordance with at least one aspect of the present disclosure.

FIG. 7 illustrates a logic diagram of a control system 470 of a surgical instrument or tool in accordance with one or more aspects of the present disclosure. The system 470 may comprise a control circuit. The control circuit may include a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 may be configured to determine the position of the longitudinally movable displacement member. The position information may be provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 may display a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHZ, a prefetch buffer to improve performance above 40 MHZ, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 may include a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

In some examples, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In some examples, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 may be a full-bridge controller for use with external N-channel power metal-oxide semiconductor field-effect transistors (MOS-FETs) specifically designed for inductive loads, such as brush DC motors. The driver 492 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the lowside FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 may comprise a controlled motor drive circuit arrangement comprising a position sensor 472 according to one aspect of this disclosure. The position sensor 472 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source may supplie power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 472 may be equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches may be fed back to the microcontroller 461 that applies logic to determine a unique position signal corresponding to the longitudinal linear displacement $d1+d2+ . . . dn$ of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system may comprise a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 may be a low-voltage and low-power component and includes four Hall-effect elements in an area of the position sensor 472 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bitshift, and table lookup operations. The angle position, alarm bits, and magnetic field information may be transmitted over a standard serial communication interface, such as a serial peripheral interface (SPI) interface, to the microcontroller 461. The position sensor 472 may provide 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertial, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force may be converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 474, such as, for example, a micro-strain gauge, that can be configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain can be converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub 203 as shown in FIGS. 5 and 6.

Figure 8:
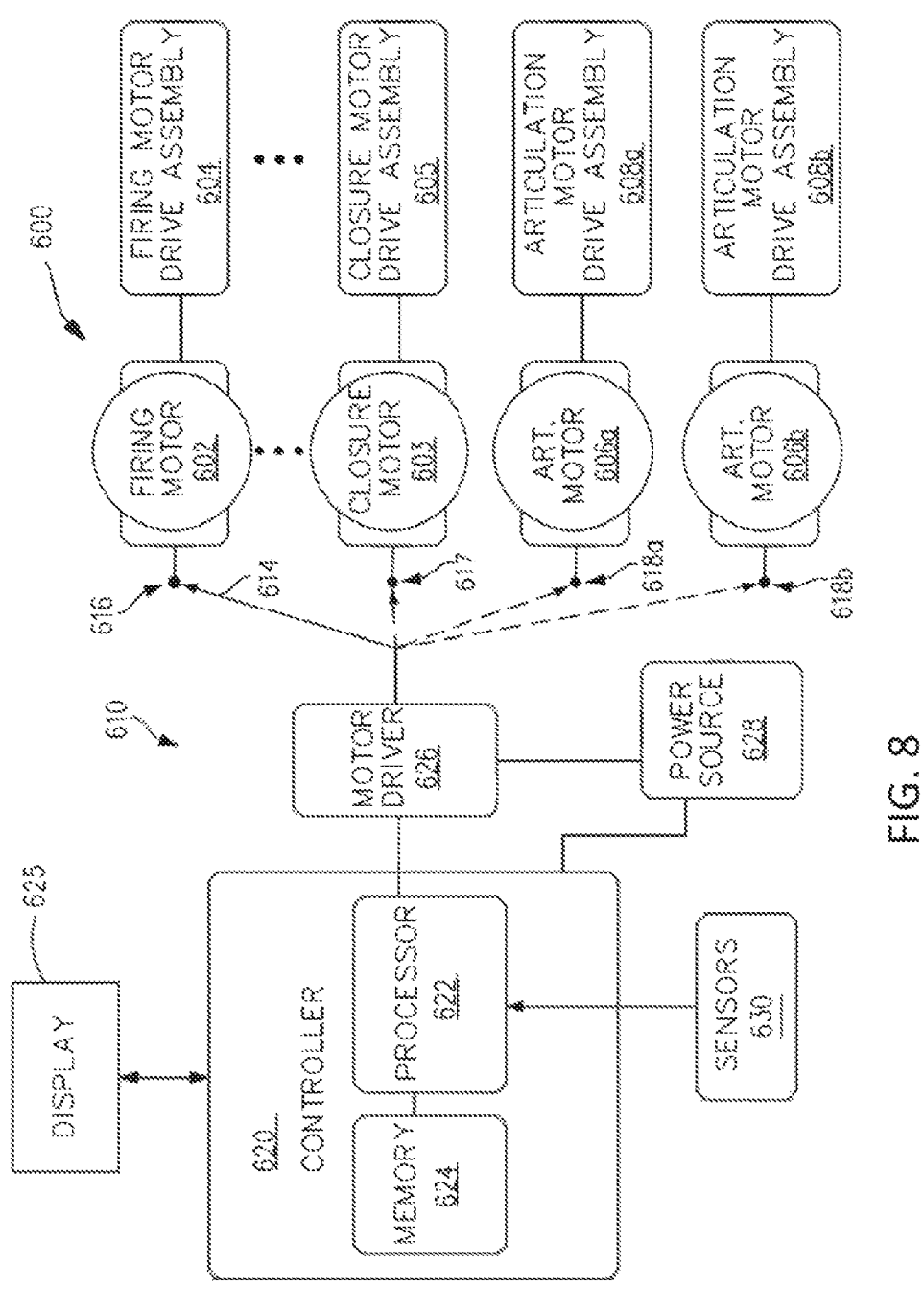
FIG. 8 illustrates a surgical instrument or tool comprising a plurality of motors which can be activated to perform various functions, in accordance with at least one aspect of the present disclosure.

FIG. 8 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described herein, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 8, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 8, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described herein.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor can be a multipurpose, programmable device that accepts digital data as input, processes it according to instructions stored in its memory, and provides results as output. It can be an example of sequential digital logic, as it may have internal memory. Processors may operate on numbers and symbols represented in the binary numeral system.

The processor 622 may be any single-core or multicore processor such as those known under the trade name ARM Cortex by Texas Instruments. In certain instances, the microcontroller 620 may be an LM4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHZ, a prefetch buffer to improve performance above 40 MHZ, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

The memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

One or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 9:
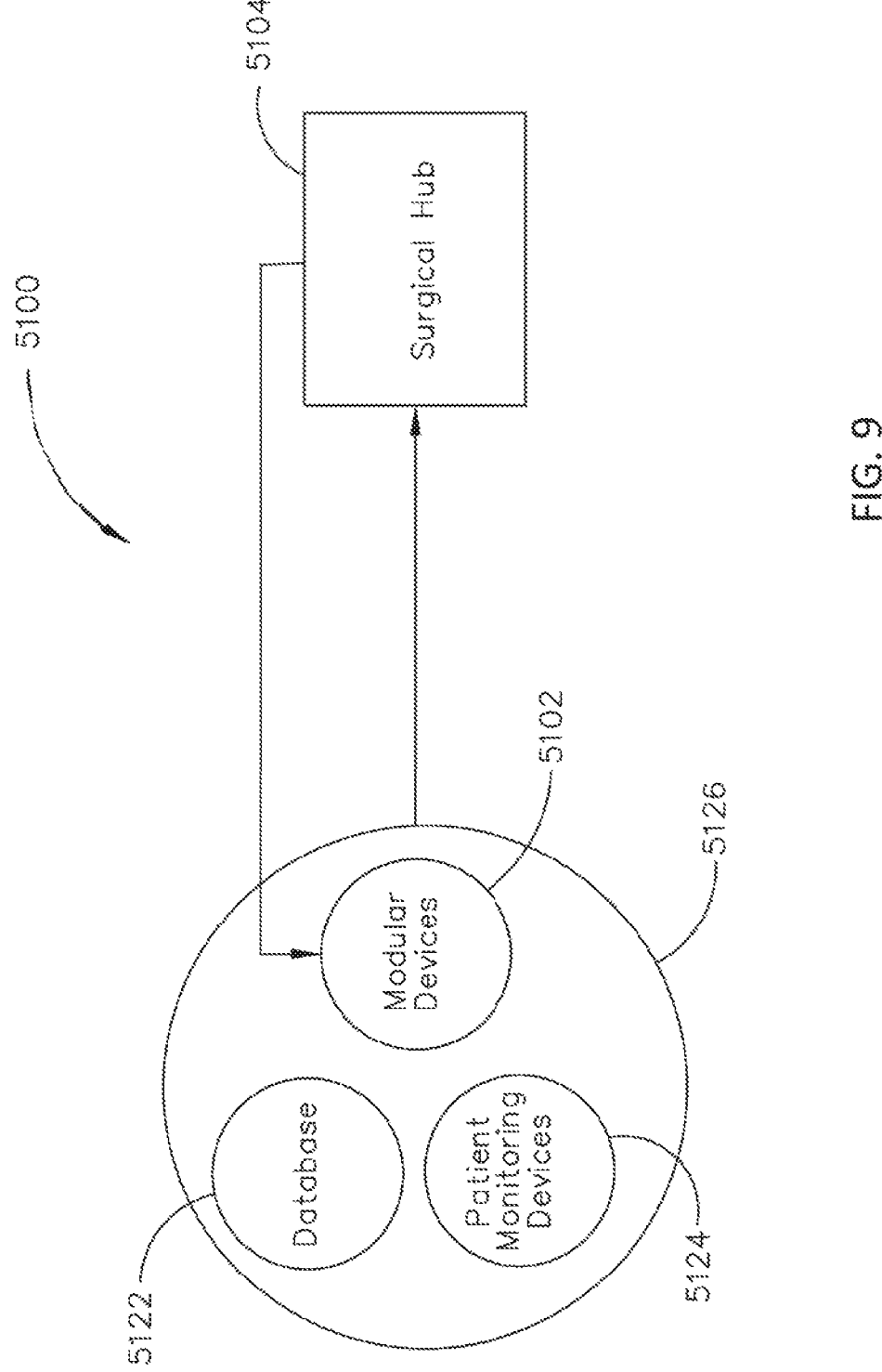
FIG. 9 illustrates a diagram of a situationally aware surgical system, in accordance with at least one aspect of the present disclosure.

FIG. 9 illustrates a diagram of a situationally aware surgical system 5100, in accordance with at least one aspect of the present disclosure. In some exemplifications, the data sources 5126 may include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiogramonitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In an exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In an exemplification, the situational awareness system can include a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in an exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use a soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can be configured to compare the list of items for the procedure and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In some exemplifications, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In some exemplifications, the surgical hub 5104 can be configured to provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Figure 10:
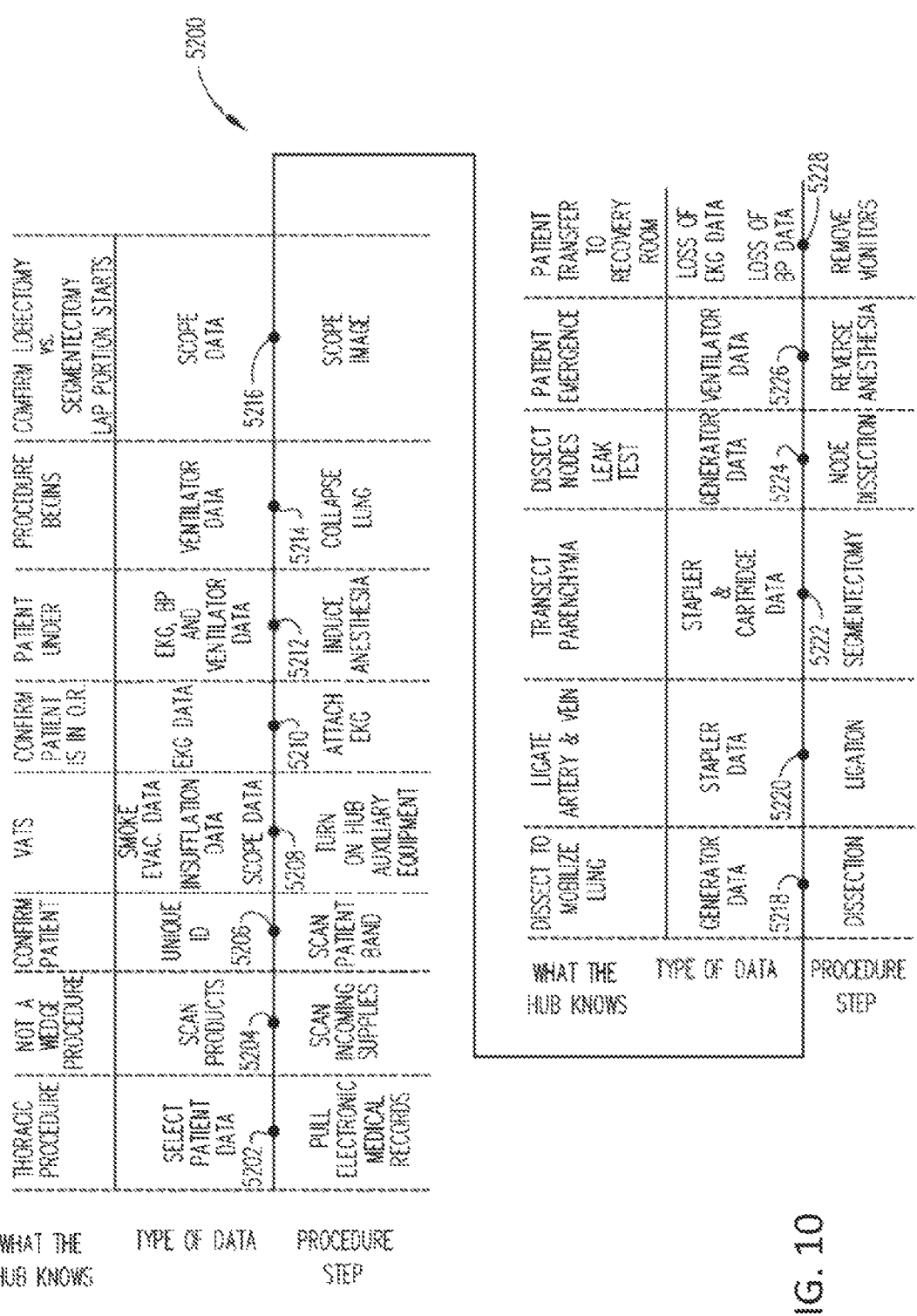
FIG. 10 illustrates a timeline of an illustrative surgical procedure and the inferences that the surgical hub can make from the data detected at each step in the surgical procedure, in accordance with at least one aspect of the present disclosure.

FIG. 10 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 9, reference should also be made to FIG. 9. The timeline 5200 may depict the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 may receive data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 can be able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described herein.

As the first step S202 in this illustrative procedure, the hospital staff members may retrieve the patient's EMR from the hospital's EMR database. Based on select patient data in the EMR, the surgical hub 5104 determines that the procedure to be performed is a thoracic procedure. Second 5204, the staff members may scan the incoming medical supplies for the procedure. The surgical hub 5104 cross-references the scanned supplies with a list of supplies that can be utilized in various types of procedures and confirms that the mix of supplies corresponds to a thoracic procedure. Further, the surgical hub 5104 may also be able to determine that the procedure is not a wedge procedure (because the incoming supplies either lack certain supplies that are necessary for a thoracic wedge procedure or do not otherwise correspond to a thoracic wedge procedure). Third 5206, the medical personnel may scan the patient band via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that may be located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 may determine that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 may pair with the surgical hub 5104. As the surgical hub 5104 begins receiving data from the patient monitoring devices 5124, the surgical hub 5104 may confirm that the patient is in the operating theater, as described in the process 5207, for example. Sixth 5212, the medical personnel may induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof. for example. Upon completion of the sixth step S212, the pre-operative portion of the lung segmentectomy procedure is completed and the operative portion begins.

Seventh 5214, the patient's lung that is being operated on may be collapsed (while ventilation is switched to the contralateral lung). The surgical hub 5104 can infer from the ventilator data that the patient's lung has been collapsed, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung can be the first operative step in this particular procedure. Eighth 5216, the medical imaging device 5108 (e.g., a scope) may be inserted and video from the medical imaging device may be initiated. The surgical hub 5104 may receive the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy may place the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. An example technique for performing a VATS lobectomy may utilize a single medical imaging device. An example technique for performing a VATS segmentectomy utilizes multiple cameras. An example technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team may begin the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team may proceed to the ligation step of the procedure. The surgical hub 5104 can infer that the surgeon is ligating arteries and veins because it may receive data from the surgical stapling and cutting instrument indicating that the instrument is being fired. Similar to the prior step, the surgical hub 5104 can derive this inference by cross-referencing the receipt of data from the surgical stapling and cutting instrument with the retrieved steps in the process. Eleventh 5222, the segmentectomy portion of the procedure can be performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (e.g., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step S224, the incisions and closed up and the post-operative portion of the procedure may begin.

Thirteenth 5226, the patient's anesthesia can be reversed. The surgical hub 5104 can infer that the patient is emerging from the anesthesia based on the ventilator data (i.e., the patient's breathing rate begins increasing), for example. Lastly, the fourteenth step S228 may be that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step S202 of the timeline 5200 depicted in FIG. 10, the patient data can also be utilized by a situationally aware surgical hub 5104 to generate control adjustments for the paired modular devices 5102.

Figure 11:
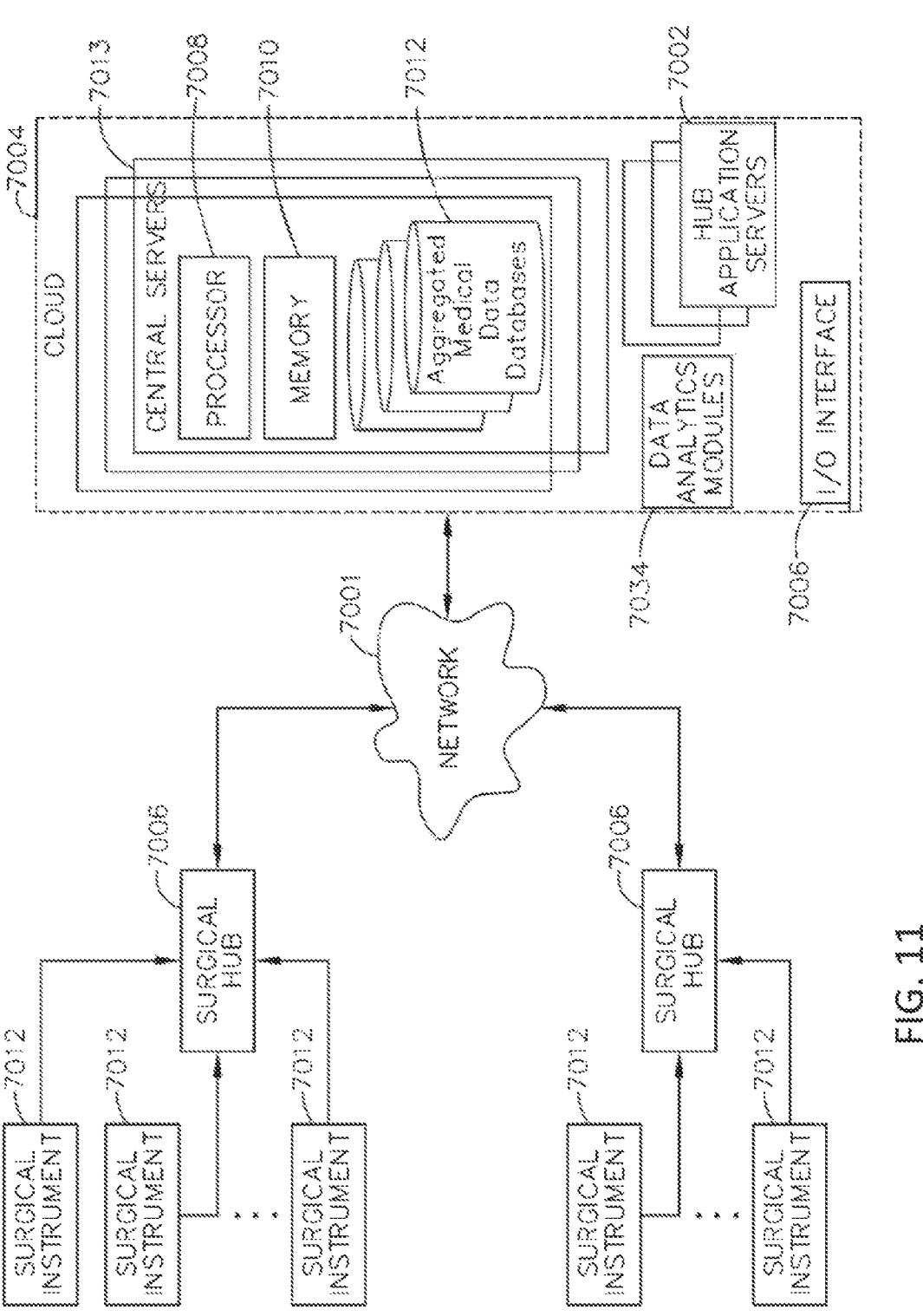
FIG. 11 is a block diagram of the computer-implemented interactive surgical system, in accordance with at least one aspect of the present disclosure.

FIG. 11 is a block diagram of the computer-implemented interactive surgical system, in accordance with at least one aspect of the present disclosure. In one aspect, the computer-implemented interactive surgical system may be configured to monitor and analyze data related to the operation of various surgical systems that include surgical hubs, surgical instruments, robotic devices and operating theaters or healthcare facilities. The computer-implemented interactive surgical system may comprise a cloud-based analytics system. Although the cloud-based analytics system may be described as a surgical system, it may not be necessarily limited as such and could be a cloud-based medical system generally. As illustrated in FIG. 11, the cloud-based analytics system may comprise a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 may be communicatively coupled to one or more surgical instruments 7012. The hubs 7006 may also be communicatively coupled to the cloud 7004 of the computer-implemented interactive surgical system via the network 7001. The cloud 7004 may be a remote centralized source of hardware and software for storing, manipulating, and communicating data generated based on the operation of various surgical systems. As shown in FIG. 11, access to the cloud 7004 may be achieved via the network 7001, which may be the Internet or some other suitable computer network. Surgical hubs 7006 that may be coupled to the cloud 7004 can be considered the client side of the cloud computing system (i.e., cloud-based analytics system). Surgical instruments 7012 may be paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 11, the cloud 7004 comprises central servers 7013 (may be same or similar to remote server 7013), hub application servers 7002, data analytics modules 7034, and an input/output ("I/O") interface 7006. The central servers 7013 of the cloud 7004 collectively administer the cloud computing system, which includes monitoring requests by client surgical hubs 7006 and managing the processing capacity of the cloud 7004 for executing the requests. Each of the central servers 7013 may comprise one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also may comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7012 of the cloud 7004. In particular, the cloud 7004 may advantageously perform data analysis and operations on the aggregated data to yield insights and/or perform functions that individual hubs 7006 could not achieve on their own. To this end, as shown in FIG. 11, the cloud 7004 and the surgical hubs 7006 are communicatively coupled to transmit and receive information. The I/O interface 7006 is connected to the plurality of surgical hubs 7006 via the network 7001. In this way, the I/O interface 7006 can be configured to transfer information between the surgical hubs 7006 and the aggregated medical data databases 7011. Accordingly, the I/O interface 7006 may facilitate read/write operations of the cloud-based analytics system. Such read/write operations may be executed in response to requests from hubs 7006. These requests could be transmitted to the hubs 7006 through the hub applications. The I/O interface 7006 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 may be configured to host and supply shared capabilities to software applications (e.g., hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 12.

The particular cloud computing system configuration described in the present disclosure may be specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch-controlled user interfaces such that clinicians may control aspects of interaction between the surgical instruments 7012 and the cloud 7004. Other suitable user interfaces for control such as auditory controlled user interfaces can also be used.

Figure 12:
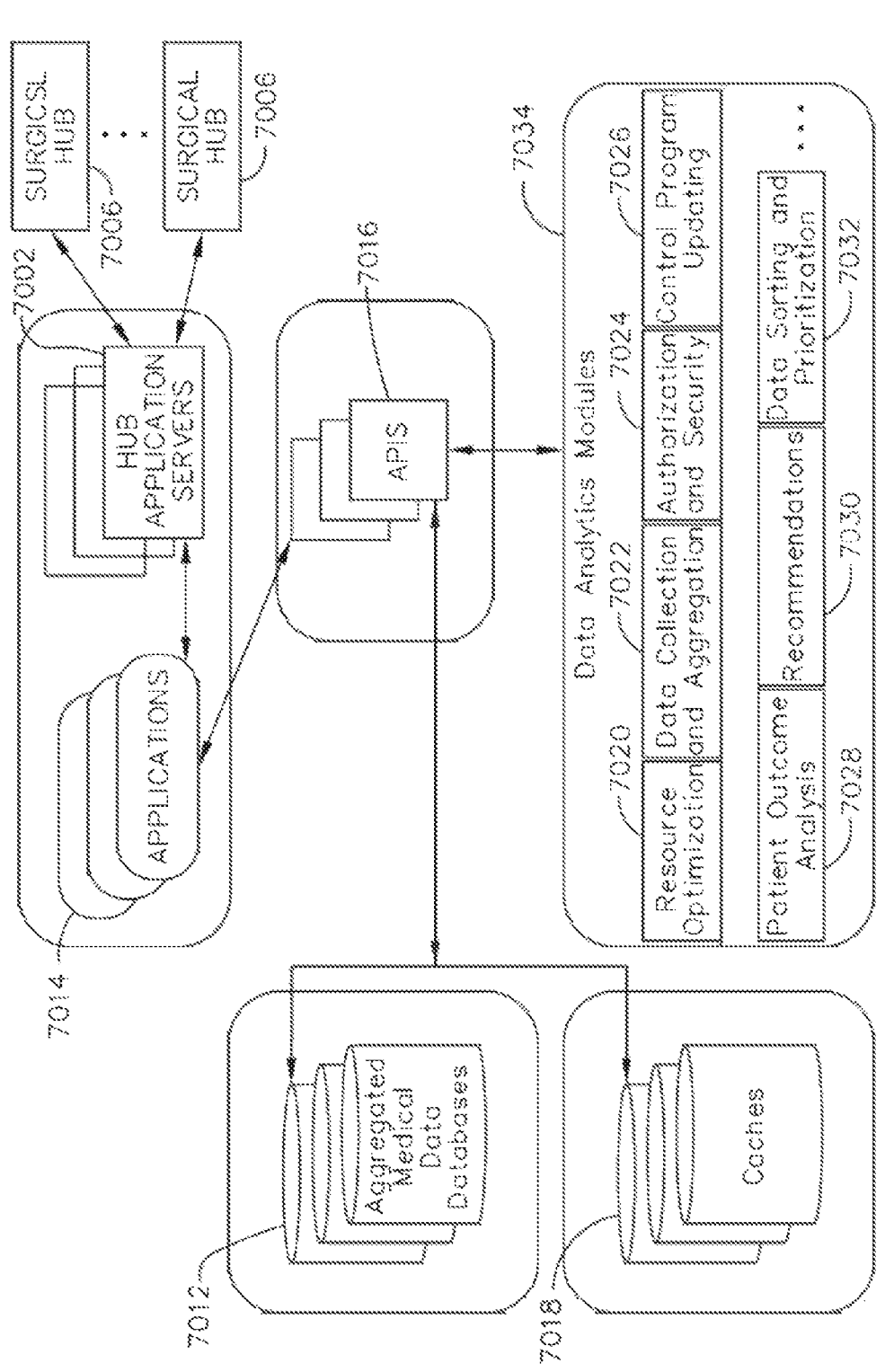
FIG. 12 is a block diagram which illustrates the functional architecture of the computer-implemented interactive surgical system, in accordance with at least one aspect of the present disclosure.

FIG. 12 is a block diagram which illustrates the functional architecture of the computer-implemented interactive surgical system, in accordance with at least one aspect of the present disclosure. The cloud-based analytics system may include a plurality of data analytics modules 7034 that may be executed by the processors 7008 of the cloud 7004 for providing data analytic solutions to problems specifically arising in the medical field. As shown in FIG. 12, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 may define the set of protocols and routines corresponding to the hub applications 7014. Additionally, the APIs 7016 may manage the storing and retrieval of data into and from the aggregated medical databases 7012 for the operations of the applications 7014. The caches 7018 may also store data (e.g., temporarily) and may be coupled to the APIs 7016 for more efficient retrieval of data used by the applications 7014. The data analytics modules 7034 in FIG. 12 may include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules may be used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently. The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that may be transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004. Furthermore, for security purposes, the cloud could maintain a database of hubs 7006, instruments 7012, and other devices that may comprise a "black list" of prohibited devices. In particular, a surgical hubs 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally, or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash-based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described herein to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g., a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional example details for the various functions described are provided in the ensuing descriptions below. Each of the various descriptions may utilize the cloud architecture as described in FIGS. 11 and 12 as one example of hardware and software implementation.

Figure 13:
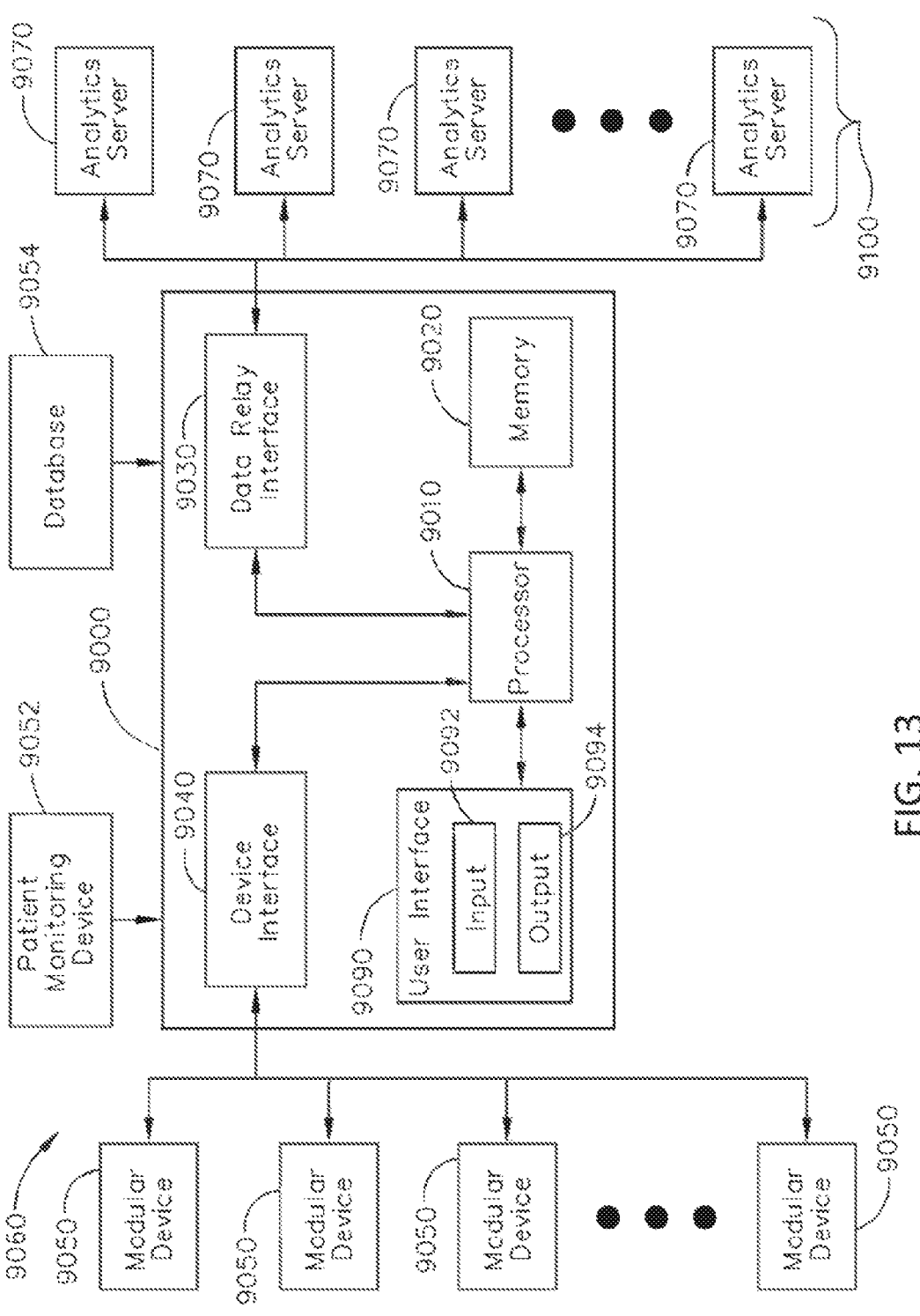
FIG. 13 illustrates a block diagram of a computer-implemented interactive surgical system that is configured to adaptively generate control program updates for modular devices, in accordance with at least one aspect of the present disclosure.

FIG. 13 illustrates a block diagram of a computer-implemented adaptive surgical system 9060 that is configured to adaptively generate control program updates for modular devices 9050, in accordance with at least one aspect of the present disclosure. In some exemplifications, the surgical system may include a surgical hub 9000, multiple modular devices 9050 communicably coupled to the surgical hub 9000, and an analytics system 9100 communicably coupled to the surgical hub 9000. Although a single surgical hub 9000 may be depicted, it should be noted that the surgical system 9060 can include any number of surgical hubs 9000, which can be connected to form a network of surgical hubs 9000 that are communicably coupled to the analytics system 9010. In some exemplifications, the surgical hub 9000 may include a processor 9010 coupled to a memory 9020 for executing instructions stored thereon and a data relay interface 9030 through which data is transmitted to the analytics system 9100. In some exemplifications, the surgical hub 9000 further may include a user interface 9090 having an input device 9092 (e.g., a capacitive touchscreen or a keyboard) for receiving inputs from a user and an output device 9094 (e.g., a display screen) for providing outputs to a user. Outputs can include data from a query input by the user, suggestions for products or mixes of products to use in a given procedure, and/or instructions for actions to be carried out before, during, or after surgical procedures. The surgical hub 9000 further may include an interface 9040 for communicably coupling the modular devices 9050 to the surgical hub 9000. In one aspect, the interface 9040 may include a transceiver that is communicably connectable to the modular device 9050 via a wireless communication protocol. The modular devices 9050 can include, for example, surgical stapling and cutting instruments, electrosurgical instruments, ultrasonic instruments, insufflators, respirators, and display screens. In some exemplifications, the surgical hub 9000 can further be communicably coupled to one or more patient monitoring devices 9052, such as EKG monitors or BP monitors. In some exemplifications, the surgical hub 9000 can further be communicably coupled to one or more databases 9054 or external computer systems, such as an EMR database of the medical facility at which the surgical hub 9000 is located.

When the modular devices 9050 are connected to the surgical hub 9000, the surgical hub 9000 can sense or receive perioperative data from the modular devices 9050 and then associate the received perioperative data with surgical procedural outcome data. The perioperative data may indicate how the modular devices 9050 were controlled during the course of a surgical procedure. The procedural outcome data includes data associated with a result from the surgical procedure (or a step thereof), which can include whether the surgical procedure (or a step thereof) had a positive or negative outcome. For example, the outcome data could include whether a patient suffered from postoperative complications from a particular procedure or whether there was leakage (e.g., bleeding or air leakage) at a particular staple or incision line. The surgical hub 9000 can obtain the surgical procedural outcome data by receiving the data from an external source (e.g., from an EMR database 9054), by directly detecting the outcome (e.g., via one of the connected modular devices 9050), or inferring the occurrence of the outcomes through a situational awareness system. For example, data regarding postoperative complications could be retrieved from an EMR database 9054 and data regarding staple or incision line leakages could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. In some exemplifications, the analytics system 9100 may include a network of analytics servers 9070 that are configured to receive data from the surgical hubs 9000. Each of the analytics servers 9070 can include a memory and a processor coupled to the memory that is executing instructions stored thereon to analyze the received data. In some exemplifications, the analytics servers 9070 may be connected in a distributed computing architecture and/or utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to the modular devices' 9050 control programs.

Additional detail regarding the computer-implemented interactive surgical system 9060, including the surgical hub 9000 and various modular devices 9050 connectable thereto, are described in connection with FIGS. 5-6.

Figure 14:
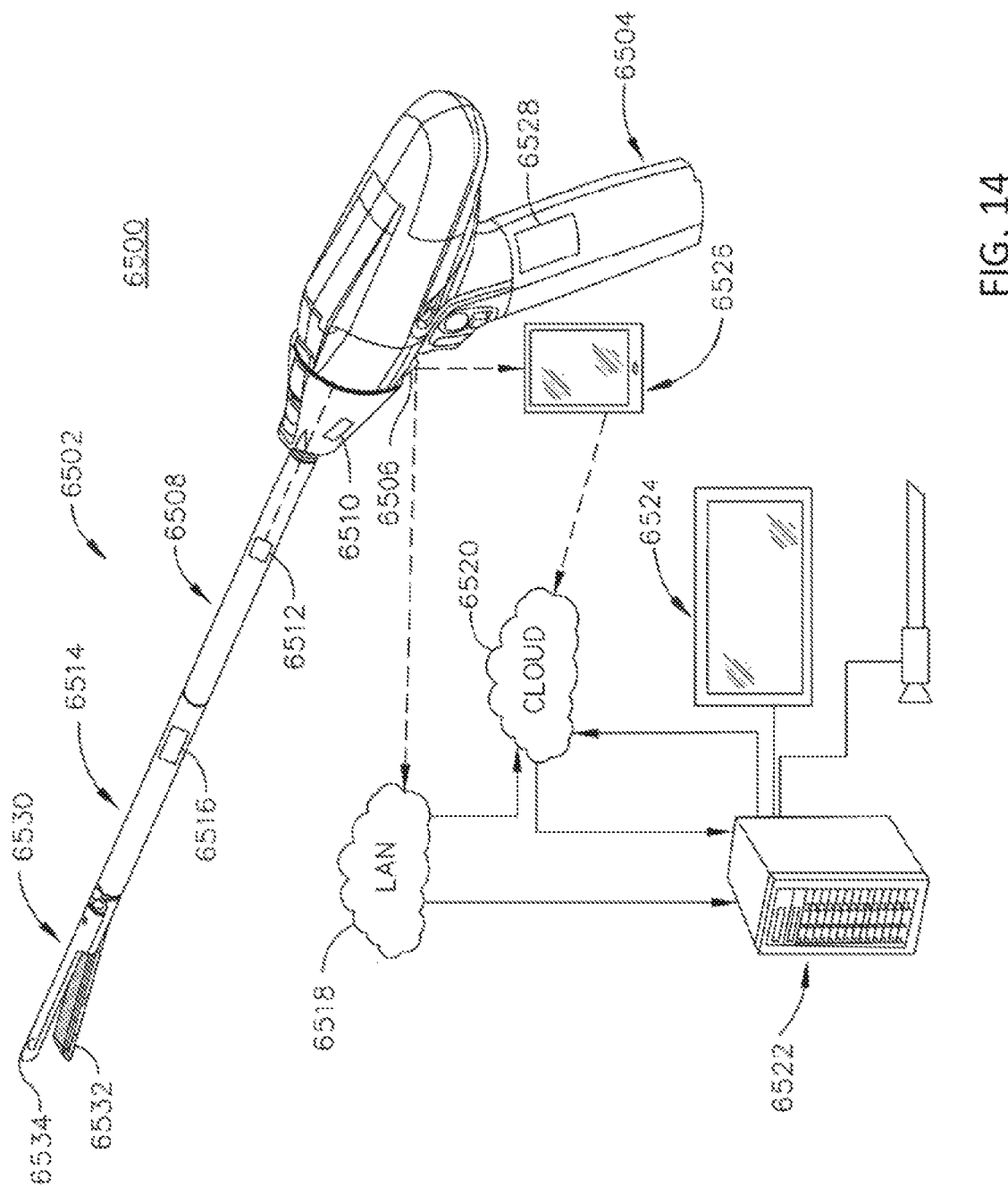
FIG. 14 illustrates a surgical system that includes a handle having a controller and a motor, an adapter releasably coupled to the handle, and a loading unit releasably coupled to the adapter, in accordance with at least one aspect of the present disclosure.

FIG. 14 provides a surgical system 6500 in accordance with the present disclosure and may include a surgical instrument 6502 that can be in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 may include a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 may include an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 may be configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more than one time prior to being replaced. The second jaw 6534 may include an anvil that deforms or otherwise secures the fasteners about tissue as the fasteners are ejected from the multi-fire fastener cartridge.

The handle 6504 may include a motor that is coupled to the drive shaft to affect rotation of the drive shaft. The handle 6504 may include a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 may be in communication with a controller 6528 of the handle 6504 to selectively activate the motor to affect rotation of the drive shafts. The controller 6528 may be disposed within the handle 6504 and is configured to receive input from the control interface and adapter data from the adapter 6508 or loading unit data from the loading unit 6514. The controller 6528 may analyze the input from the control interface and the data received from the adapter 6508 and/or loading unit 6514 to selectively activate the motor. The handle 6504 may also include a display that is viewable by a clinician during use of the handle 6504. The display may be configured to display portions of the adapter or loading unit data before, during, or after firing of the instrument 6502.

The adapter 6508 may include an adapter identification device 6510 disposed therein and the loading unit 6514 includes a loading unit identification device 6516 disposed therein. The adapter identification device 6510 may be in communication with the controller 6528, and the loading unit identification device 6516 may be in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 may provide an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 can be configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 may include a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Figures 15A, 15B:
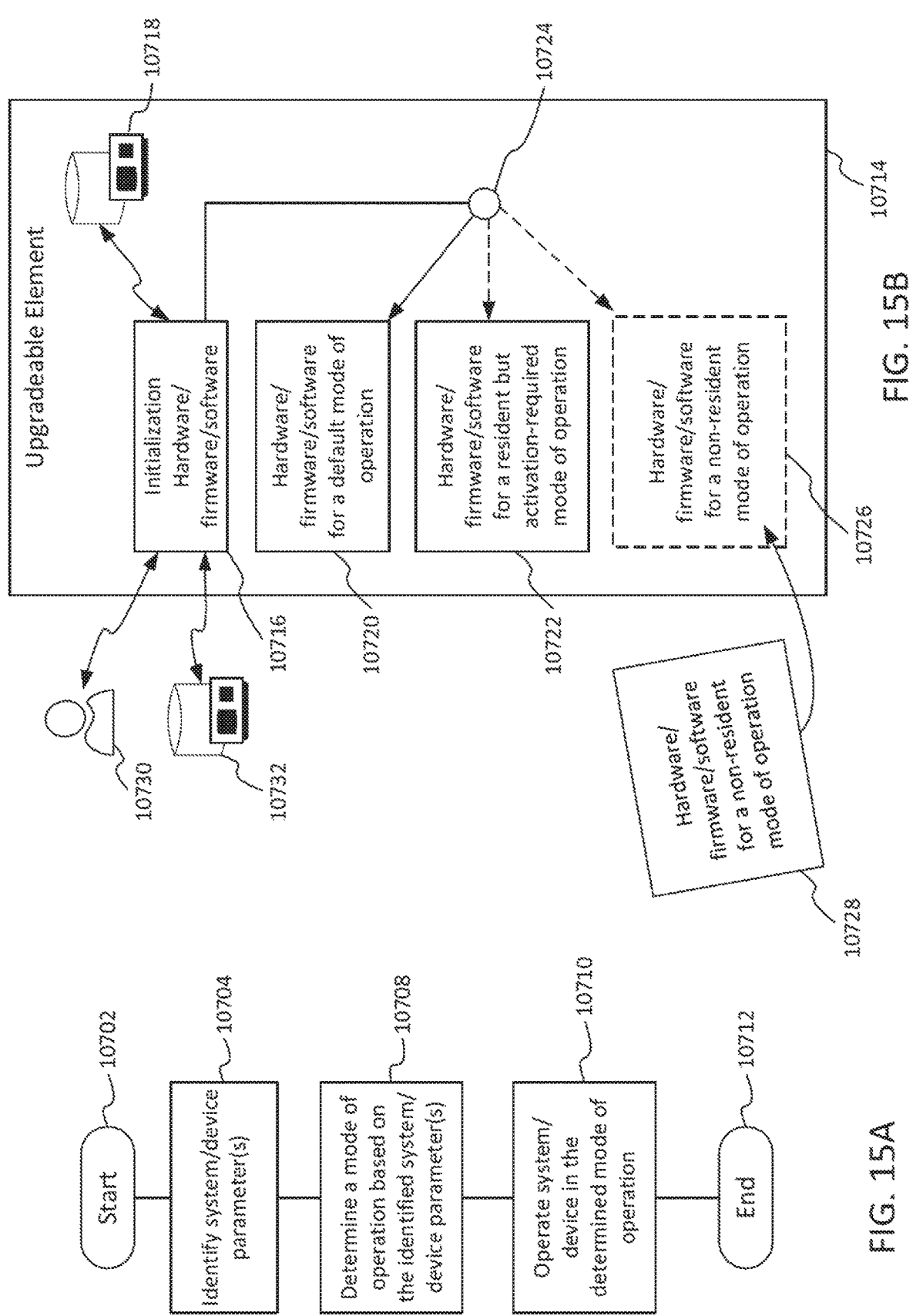
FIG. 15A illustrates an example flow for determining a mode of operation and operating in the determined mode, in accordance with at least one aspect of the present disclosure.
FIG. 15B illustrates an example flow for changing a mode of operation, in accordance with at least one aspect of the present disclosure.

FIG. 15A illustrates an example flow for determining a mode of operation and operating in the determined mode. The computer-implemented interactive surgical system and/ or components and/or subsystems of the computer-implemented interactive surgical system may be configured to be updated. Such updates may include the inclusions of features and benefits that were not available to the user before the update. These updates may be established by any method of hardware, firmware, and software updates suitable for introducing the feature to the user. For example, replaceable/swappable (e.g., hot swappable) hardware components, flashable firmware devices, and updatable software systems may be used to update computer-implemented interactive surgical system and/or components and/or subsystems of the computer-implemented interactive surgical system.

The updates may be conditioned on any suitable criterion or set of criteria. For example, an update may be conditioned on one or more hardware capabilities of the system, such as processing capability, bandwidth, resolution, and the like. For example, the update may be conditioned on one or more software aspects, such as a purchase of certain software code. For example, the update may be conditioned on a purchased service tier. The service tier may represent a feature and/or a set of features the user is entitled to use in connection with the computer-implemented interactive surgical system. The service tier may be determined by a license code, an e-commerce server authentication interaction, a hardware key, a username/password combination, a biometric authentication interaction, a public/private key exchange interaction, or the like.

At 10704, a system/device parameter may be identified. The system/device parameter may be any element or set of elements on which an update in conditioned. For example, the computer-implemented interactive surgical system may detect a certain bandwidth of communication between a modular device and a surgical hub. For example, the computer-implemented interactive surgical system may detect an indication of the purchase of certain service tier.

At 10708, a mode of operation may be determined based on the identified system/device parameter. This determination may be made by a process that maps system/device parameters to modes of operation. The process may be a manual and/or an automated process. The process may be the result of local computation and/or remote computation. For example, a client/server interaction may be used to determine the mode of operation based on the on the identified system/device parameter. For example, local software and/or locally embedded firmware may be used to determine the mode of operation based on the identified system/device parameter. For example, a hardware key, such as a secure microprocessor for example, may be used to determine the mode of operation based on the identified system/device parameter.

At 10710, operation may proceed in accordance with the determined mode of operation. For example, a system or device may proceed to operate in a default mode of operation. For example, a system or device may proceed to operate in an alternate mode of operation. The mode of operation may be directed by control hardware, firmware, and/or software already resident in the system or device. The mode of operation may be directed by control hardware, firmware, and/or software newly installed/updated.

FIG. 15B illustrates an example functional block diagram for changing a mode of operation. An upgradeable element 10714 may include an initialization component 10716. The initialization component 10716 may include any hardware, firmware, and/or software suitable determining a mode of operation. For example, the initialization component 10716 may be portion of a system or device start-up procedure. The initialization component 10716 may engage in an interaction to determine a mode of operation for the upgradeable element 10714. For example, the initialization component 10716 may interact with a user 10730, an external resource 10732, and/or a local resource 10718 for example. For example, the initialization component 10716 may receive a licensing key from the user 10730 to determine a mode of operation. The initialization component 10716 may query an external resource 10732, such as a server for example, with a serial number of the upgradable device 10714 to determine a mode of operation. For example, the initialization component 10716 may query a local resource 10718, such as a local query to determine an amount of available bandwidth and/or a local query of a hardware key for example, to determine a mode of operation.

The upgradeable element 10714 may include one or more operation components 10720, 10722, 10726, 10728 and an operational pointer 10724. The initialization component 10716 may direct the operational pointer 10724 to direct the operation of the upgradable element 10741 to the operation component 10720, 10722, 10726, 10728 that corresponds with the determined mode of operation. The initialization component 10716 may direct the operational pointer 10724 to direct the operation of the upgradable element to a default operation component 10720. For example, the default operation component 10720 may be selected on the condition of no other alternate mode of operation being determined. For example, the default operation component 10720 may be selected on the condition of a failure of the initialization component and/or interaction failure. The initialization component 10716 may direct the operational pointer 10724 to direct the operation of the upgradable element 10714 to a resident operation component 10722. For example, certain features may be resident in the upgradable component 10714 but require activation to be put into operation. The initialization component 10716 may direct the operational pointer 10724 to direct the operation of the upgradable element 10714 to install a new operation component 10728 and/or a new installed operation component 10726. For example, new software and/or firmware may be downloaded. The new software and or firmware may contain code to enable the features represented by the selected mode of operation. For example, a new hardware component may be installed to enable the selected mode of operation.

Figure 16:
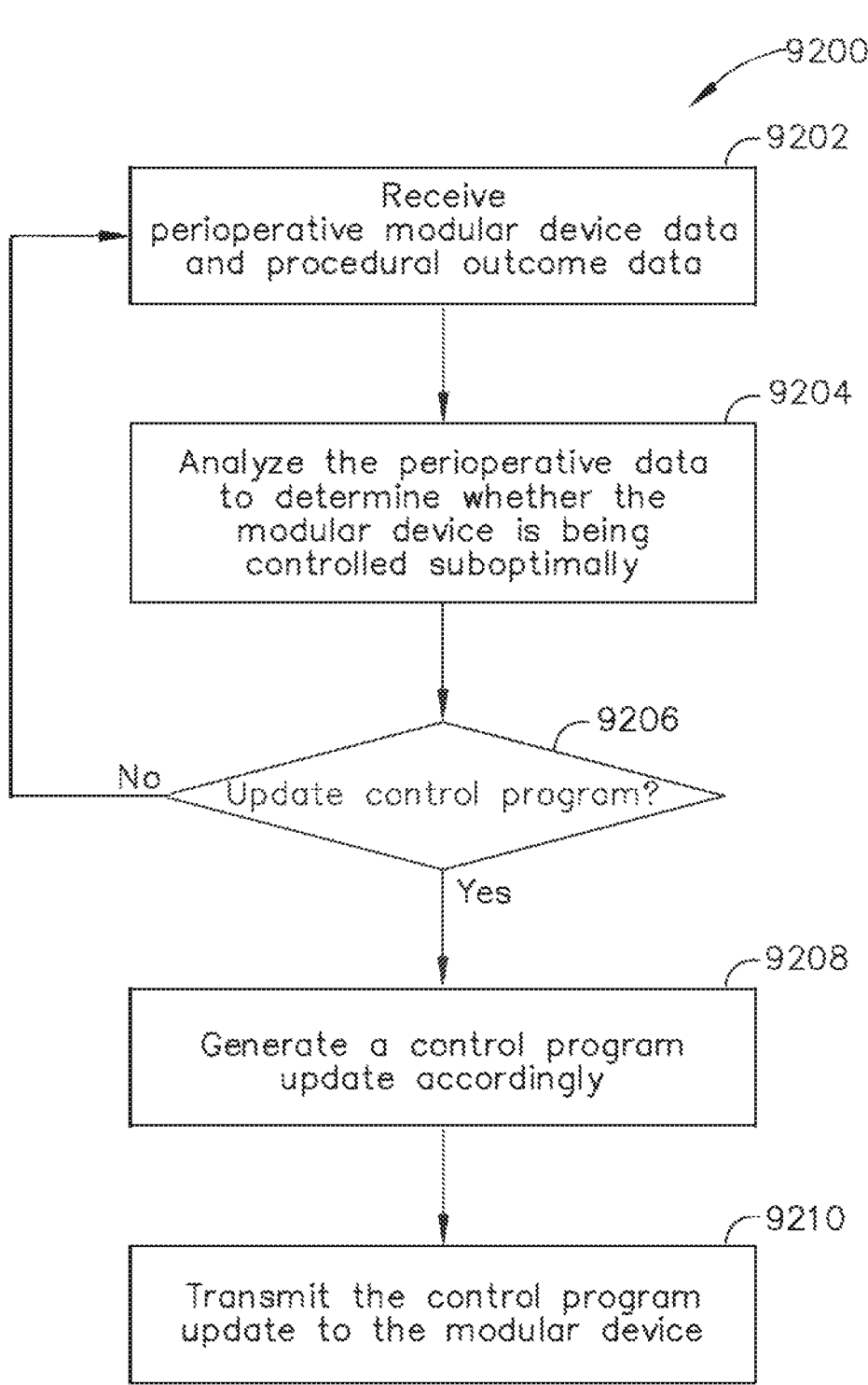
FIG. 16 illustrates a logic flow diagram of a process for updating the control program of a modular device, in accordance with at least one aspect of the present disclosure.

FIG. 16 illustrates a logic flow diagram of a process 9200 for updating the control program of a modular device 9050, in accordance with at least one aspect of the present disclosure. The process 9200 can be executed by, for example, one or more processors of the analytics servers 9070 of the analytics system 9100. In one exemplification, the analytics system 9100 can be a cloud computing system. For economy, the following description of the process 9200 will be described as being executed by the analytics system 9100; however, it should be understood that the analytics system 9100 includes processor(s) and/or control circuit(s) that are executing the describe steps of the process 9200.

The analytics system 9100 receives 9202 modular device 9050 perioperative data and surgical procedural outcome data from one or more of the surgical hubs 9000 that are communicably connected to the analytics system 9100. The perioperative data includes preoperative data, intraoperative data, and/or postoperative data detected by a modular device 9050 in association with a given surgical procedure. For modular devices 9050 or particular functions of modular devices 9050 that are manually controlled, the perioperative data indicates the manner in which a surgical staff member operated the modular devices 9050. For modular devices 9050 or particular functions of modular devices 9050 that are controlled by the modular devices' control programs, the perioperative data indicates the manner in which the control programs operated the modular devices 9050. The manner in which the modular devices 9050 function under particular sets of conditions (either due to manual control or control by the modular devices' 9050 control programs) can be referred to as the "operational behavior" exhibited by the modular device 9050. The modular device 9050 perioperative data includes data regarding the state of the modular device 9050 (e.g., the force to fire or force to close for a surgical stapling and cutting instrument or the power output for an electro surgical or ultrasonic instrument), tissue data measured by the modular device 9050 (e.g., impedance, thickness, or stiffness), and other data that can be detected by a modular device 9050. The perioperative data indicates the manner in which the modular devices 9050 were programmed to operate or were manually controlled during the course of a surgical procedure because it indicates how the modular devices 9050 functioned in response to various detected conditions.

The surgical procedural outcome data includes data pertaining to an overall outcome of a surgical procedure (e.g., whether there was a complication during the surgical procedure) or data pertaining to an outcome of a specific step within a surgical procedure (e.g., whether a particular staple line bled or leaked). The procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. Patent Publication No. 2019/0201140 A1, or retrieved from a database 9054 (e.g., an EMR database) by the surgical hub 9000 or the analytics system 9100. The procedural outcome data can include whether each outcome represented by the data was a positive or negative result. Whether each out-come was positive or negative can be determined by the modular devices 9050 themselves and included in the perioperative data transmitted to the surgical hubs 9000 or determined or inferred by the surgical hubs 9000 from the received perioperative data. For example, the procedural outcome data for a staple line that bled could include that the bleeding represented a negative outcome. Similarly, the procedural outcome data for a staple line that did not bleed could include that the lack of bleeding represented a positive outcome. In another exemplification, the analytics system 9100 can be configured to determine whether a procedural outcome is a positive or negative outcome based upon the received procedural outcome data. In some exemplifications, correlating the modular device 9050 data to positive or negative procedural outcomes allows the analytics system 9100 to determine whether a control program update should be generated 9208.

Upon the analytics system 9100 receiving 9202 the data, the analytics system 9100 analyzes the modular device 9050 and procedural outcome data to determine 9204 whether the modular devices 9050 are being utilized suboptimally in connection with the particular procedure or the particular step of the procedure. A modular device 9050 can be controlled suboptimally if the particular manner in which the modular device 9050 is being controlled is repeatedly causing an error or if an alternative manner of controlling the modular device 9050 is superior under the same conditions. The analytics system 9100 can thus determine whether a modular device 9050 is being controlled suboptimally (either manually or by its control program) by comparing the rate of positive and/or negative outcomes produced by the modular device 9050 relative to set thresholds or the performance of other modular devices 9050 of the same type.

For example, the analytics system 9100 can determine whether a type of modular device 9050 is being operated suboptimally if the rate of negative procedural outcomes produced by the modular device 9050 under a particular set of conditions in association with a particular operational behavior exceeds an average or threshold level. As a specific example, the analytics system 9100 can analyze 9204 whether a control program for a surgical stapling instrument that dictates a particular force to fire (or ranges of forces to fire) is suboptimal for a particular tissue thickness and tissue type. If the analytics system 9100 determines that the instrument generates an abnormally high rate of leaky staple lines when fired at the particular force (e.g., causing the staples to be malformed, not fully penetrate the tissue, or tear the tissue) relative to an average or threshold staple line leakage rate, then the analytics system 9100 can determine that the control program for the surgical stapling instrument is performing suboptimally given the tissue conditions.

As another example, the analytics system 9100 can determine whether a type of modular device 9050 is being operated suboptimally if the rate of positive outcomes produced by an alternative manner of control under a particular set of conditions in association with a particular operational behavior exceeds the rate of positive outcomes generated by the analyzed manner of control under the same conditions. In other words, if one subpopulation of the type of modular device 9050 exhibits a first operational behavior under a certain set of conditions and a second subpopulation of the same type of modular device 9050 exhibits a second operational behavior under the same set of conditions, then the analytics system 9100 can determine whether to update the control programs of the modular devices 9050 according to whether the first or second operational behavior is more highly correlated to a positive procedural outcome. As a specific example, the analytics system 9100 can analyze 9204 whether a control program for an RF electrosurgical or ultrasonic instrument that dictates a particular energy level is suboptimal for a particular tissue type and environmental conditions. If the analytics system 9100 determines that a first energy level given a set of tissue conditions and environmental conditions (e.g., the instrument being located in a liquid-filled environment, as in an arthroscopic procedure) produces a lower rate of hemostasis than a second energy level, then the analytics system 9100 can determine that the control program for the electrosurgical or ultrasonic instrument dictating the first energy level is performing suboptimally for the given tissue and environmental conditions.

After analyzing 9204 the data, the analytics system 9100 determines 9206 whether to update the control program. If the analytics system 9100 determines that the modular device 9050 is not being controlled suboptimally, then the process 9200 continues along the NO branch and the analytics system 9100 continues analyzing 9204 received 9202 data, as described above. If the analytics system 9100 determines that the modular device 9050 is being controlling suboptimally, then the process 9200 continues along the YES branch and the analytics system 9100 generates 9208 a control program update. The generated 9208 control program update includes, for example, a new version of the control program for the particular type of modular device 9050 to overwrite the prior version or a patch that partially overwrites or supplements the prior version.

The type of control program update that is generated 9208 by the analytics system 9100 depends upon the particular suboptimal behavior exhibited by the modular device 9050 that is identified by the analytics system 9100. For example, if the analytics system 9100 determines that a particular force to fire a surgical stapling instrument results in an increased rate of leaking staple lines, then the analytics system 9100 can generate 9208 a control program update that adjusts the force to fire from a first value to a second value that corresponds to a higher rate of non-leaking staple lines or a lower rate of leaking staple lines. As another example, if the analytics system 9100 determines that a particular energy level for an electrosurgical or ultrasonic instrument produces a low rate of hemostasis when the instrument is used in a liquid-filled environment (e.g., due to the energy dissipating effects of the liquid), then the analytics system 9100 can generated 9208 a control program update that adjusts the energy level of the instrument when it is utilized in surgical procedures where the instrument will be immersed in liquid.

The type of control program update that is generated 9208 by the analytics system 9100 also depends upon whether the suboptimal behavior exhibited by the modular device 9050 is caused by manual control or control by the control program of the modular device 9050. If the subop-timal behavior is caused by manual control, the control program update can be configured to provide warnings, recommendations, or feedback to the users based upon the manner in which they are operating the modular devices 9050. Alternatively, the control program update can change the manually controlled operation of the modular device 9050 to an operation that is controlled by the control program of the modular device 9050. The control program update may or may not permit the user to override the control program's control of the particular function. In one exemplification, if the analytics system 9100 determines 9204 that surgeons are manually setting an RF electrosurgical instrument to a suboptimal energy level for a particular tissue type or procedure type, then the analytics system 9100 can generate 9208 a control program update that provides an alert (e.g., on the surgical hub 9000 or the RF electro surgical instrument itself) recommending that the energy level be changed. In another exemplification, the generated 9208 control program update can automatically set the energy level to a default or recommended level given the particular detected circumstances, which could then be changed as desired by the medical facility staff. In yet another exem-plification, the generated 9208 control program update can automatically set the energy level to a set level determined by the analytics system 9100 and not permit the medical facility staff to change the energy level. If the suboptimal behavior is caused by the control program of the modular device 9050, then the control program update can alter how the control program functions under the particular set of circumstances that the control program is performing suboptimally under.

Once the control program update has been generated 9208 by the analytics system 9100, the analytics system 9100 then transmits 9210 or pushes the control program update to all of the modular devices 9050 of the relevant type that are connected to the analytics system 9100. The modular devices 9050 can be connected to the analytics system 9100 through the surgical hubs 900, for example. In one exemplification, the surgical hubs 9000 are configured to download the control program updates for the various types of modular devices 9050 from the analytics system 9100 each time an update is generated 9208 thereby. When the modular devices 9050 subsequently connect to or pair with a surgical hub 9000, the modular devices 9050 then automatically download any control program updates therefrom. In one exemplification, the analytics system 9100 can thereafter continue receiving 9202 and analyzing 9204 data from the modular devices 9050, as described above.

Figure 17:
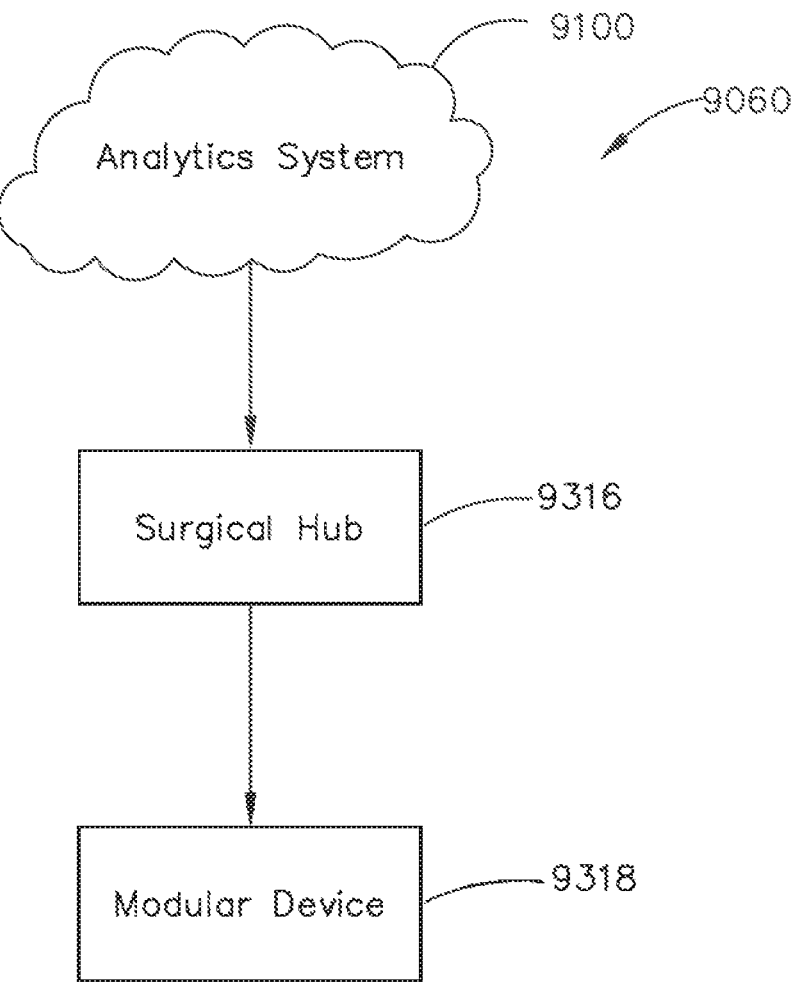
FIG. 17 illustrates a diagram of an analytics system pushing an update to a modular device through a surgical hub, in accordance with at least one aspect of the present disclosure.

In one aspect, the surgical system 9060 is configured to push down verification of software parameters and updates if modular devices 9050 are detected to be out of date in the surgical hub 9000 data stream. FIG. 17 illustrates a diagram of an analytics system 9100 pushing an update to a modular device 9050 through a surgical hub 9000, in accordance with at least one aspect of the present disclosure. In one exemplification, the analytics system 9000 is configured to transmit a generated control program update for a particular type of modular device 9050 to a surgical hub 9000. In one aspect, each time a modular device 9050 connects to a surgical hub 9000, the modular device 9050 determines whether there is an updated version of its control program on or otherwise accessible via the surgical hub 9000. If the surgical hub 9000 does have an updated control program (or the updated control program is otherwise avail-able from the analytics system 9100) for the particular type of modular device 9050, then the modular device 9050 downloads the control program update therefrom.

In one exemplification, any data set being transmitted to the analytics systems 9100 includes a unique ID for the surgical hub 9000 and the current version of its control program or operating system. In one exemplification, any data set being sent to the analytics systems 9100 includes a unique ID for the modular device 9050 and the current version of its control program or operating system. The unique ID of the surgical hub 9000 and/or modular device 9050 being associated with the uploaded data allows the analytics system 9100 to determine whether the data corresponds to the most recent version of the control program. The analytics system 9100 could, for example, elect to discount (or ignore) data generated by a modular device 9050 or surgical hub 9000 being controlled by an out of date control program and/or cause the updated version of the control program to be pushed to the modular device 9050 or surgical hub 9000.

In one exemplification, the operating versions of all modular devices 9050 the surgical hub 9000 has updated control software for could also be included in a surgical hub 9000 status data block that is transmitted to the analytics system 9100 on a periodic basis. If the analytics system 9100 identifies that the operating versions of the control programs of the surgical hub 9100 and/or any of the connectable modular devices 9050 are out of date, the analytics system 9100 could push the most recent revision of the relevant control program to the surgical hub 9000.

In one exemplification, the surgical hub 9000 and/or modular devices 9050 can be configured to automatically download any software updates. In another exemplification, the surgical hub 9000 and/or modular devices 9050 can be configured to provide a prompt for the user to ask at the next setup step (e.g., between surgical procedures) if the user wants to update the out of date control program(s). In another exemplification, the surgical hub 9000 could be programmable by the user to never allow updates or only allow updates of the modular devices 9050 and not the surgical hub 9000 itself.

Figure 18:
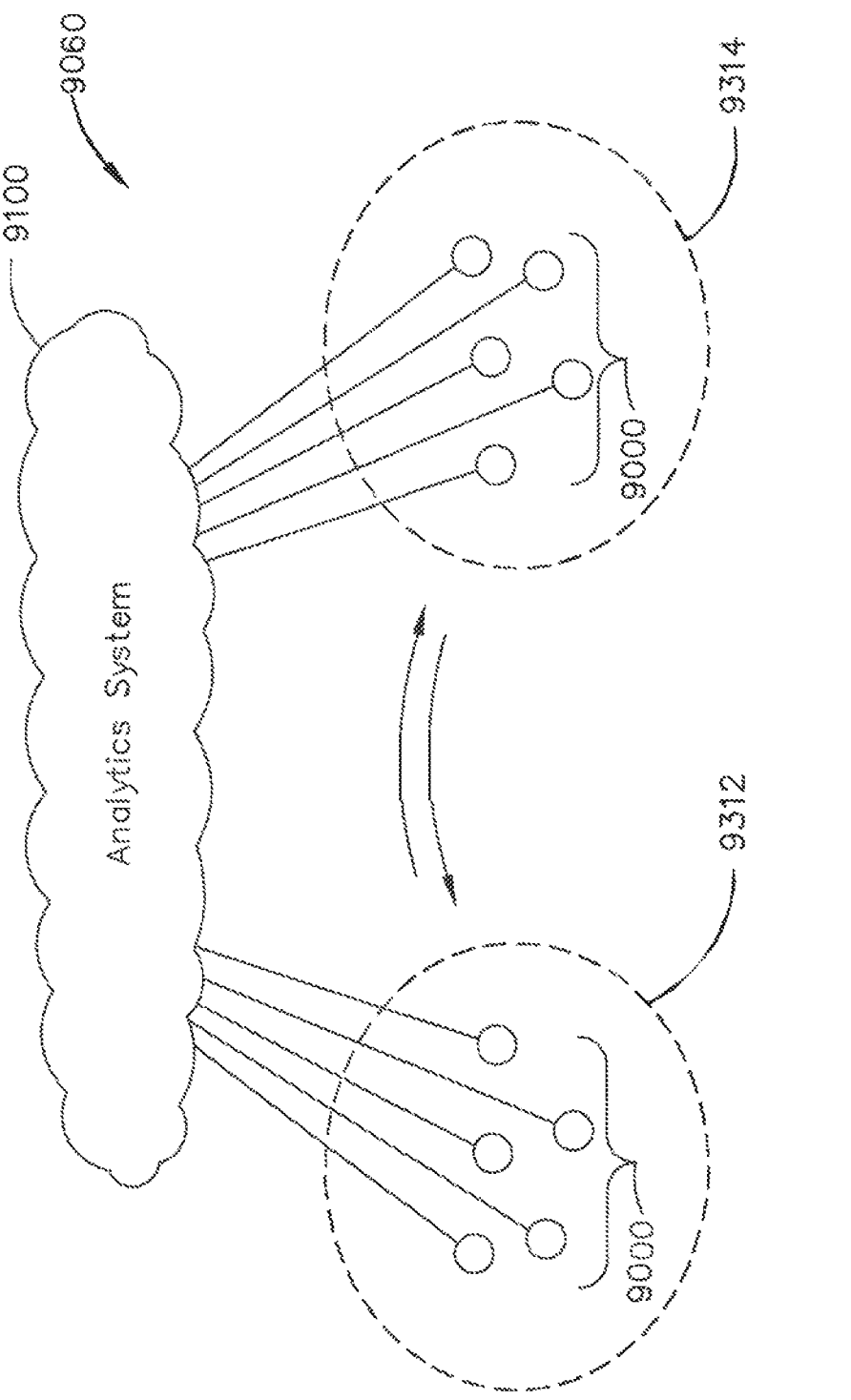
FIG. 18 illustrates a diagram of a computer-implemented interactive surgical system that is configured to adaptively generate control program updates for surgical hubs, in accordance with at least one aspect of the present disclosure.

FIG. 18 illustrates a diagram of a computer-imple-mented adaptive surgical system 9060 that is configured to adap-tively generate control program updates for surgical hubs 9000, in accordance with at least one aspect of the present disclosure. The surgical system 9060 includes several surgical hubs 9000 that are communicably coupled to the analytics system 9100. Subpopulations of surgical hubs 9000 (each of which can include individual surgical hubs 9000 or groups of surgical hubs 9000) within the overall population connected to the analytics system 9100 can exhibit different operational behaviors during the course of a surgical procedure. The differences in operational behavior between groups of surgical hubs 9000 within the population can result from the surgical hubs 9000 running different versions of their control program, by the surgical hubs' 9000 control programs being customized or programmed differently by local surgical staff, or by the local surgical staff manually controlling the surgical hubs 9000 differently. In the depicted example, the population of surgical hubs 9000 includes a first subpopulation 9312 that is exhibiting a first operational behavior and a second subpopulation 9314 that is exhibiting a second operational behavior for a particular task. Although the surgical hubs 9000 are divided into a pair of subpopulations 9312, 9314 in this particular example, there is no practical limit to the number of different behaviors exhibited within the population of surgical hubs 9000. The tasks that the surgical hubs 9000 can be executing include, for example, controlling a surgical instrument or analyzing a dataset in a particular manner.

The surgical hubs 9000 can be configured to transmit perioperative data pertaining to the operational behavior of the surgical hubs 9000 to the analytics system 9100. The perioperative data can include preoperative data, intraoperative data, and postoperative data. The preoperative data can include, for example, patient-specific information, such as demographics, health history, preexisting conditions, preoperative workup, medication history (i.e., medications currently and previously taken), genetic data (e.g., SNPs or gene expression data), EMR data, advanced imaging data (e.g., MRI, CT, or PET), metabolomics, and microbiome. Various additional types of patient-specific information that can be utilized by the analytics system 9100 are described by U.S. Pat. No. 9,250,172, U.S. patent application Ser. No. 13/631,095, U.S. patent application Ser. No. 13/828,809, and U.S. Pat. No. 8,476,227, each of which is incorporated by reference herein to the extent that they describe patient specific information. The preoperative data can also include, for example, operating theater specific information, such as geographic information, hospital location, operating theater location, operative staff performing the surgical procedure, the responsible surgeon, the number and type of modular devices 9050 and/or other surgical equipment that could potentially be used in the particular surgical procedure, the number and type of modular devices 9050 and/or other surgical equipment that are anticipated to be used in the particular surgical procedure, patient identification information, and the type of procedure being performed.

The intraoperative data can include, for example, modular device 9050 utilization (e.g., the number of firings by a surgical stapling instrument, the number of firings by an RF electrosurgical instrument or an ultrasonic instrument, or the number and types of stapler cartridges utilized), operating parameter data of the modular devices 9050 (e.g., the FTF curve for a surgical stapling instrument, a FTC curve for a surgical stapling instrument, the energy output of a generator, the internal pressure or pressure differential of a smoke evacuator), unexpected modular device 9050 utilization (i.e., the detection of the utilization of a modular device that is nonstandard for the procedure type), adjunctive therapies administered to the patient, and utilization of equipment other than the modular devices 9050 (e.g., sealants to address leaks). The intraoperative data can also include, for example, detectable misuse of a modular device 9050 and detectable off-label use of a modular device 9050.

The postoperative data can include, for example, a flag if the patient does not leave the operating theater and/or is sent for nonstandard postoperative care (e.g., a patient undergoing a routine bariatric procedure is sent to the ICU after the procedure), a postoperative patient evaluation relating to the surgical procedure (e.g., data relating to a spirometric performance after a thoracic surgery or data relating to a staple line leakage after bowel or bariatric procedures), data related to postoperative complications (e.g., transfusions or air leaks), or the patient's length of stay in the medical facility after the procedure. Because hospitals are increasingly being graded on readmission rates, complication rates, average length of stay, and other such surgical quality metrics, the postoperative data sources can be monitored by the analytics system 9100 either alone or in combination with surgical procedural outcome data (discussed below) to assess and institute updates to the controls programs of the surgical hubs 9000 and/or modular devices 9050.

In some exemplifications, the intraoperative and/or postoperative data can further include data pertaining to the outcome of each surgical procedure or a step of the surgical procedure. The surgical procedural outcome data can include whether a particular procedure or a particular step of a procedure had a positive or negative outcome. In some exemplifications, the surgical procedural outcome data can include procedure step and/or time stamped images of modular device 9050 performance, a flag indicating whether a modular device 9050 functioned properly, notes from the medical facility staff, or a flag for poor, suboptimal, or unacceptable modular device 9050 performance. The surgical procedural outcome data can, for example, be directly detected by the modular devices 9050 and/or surgical hub 9000 (e.g., a medical imaging device can visualize or detect bleeding), determined or inferred by a situational awareness system of the surgical hub 9000 as described in U.S. Patent Publication No. 2019/0201140 A1 by the surgical hub 9000 or the analytics system 9100. In some exemplifications, perioperative data including a flag indicating that a modular device 9050 failed or otherwise performed poorly during the course of a surgical procedure can be prioritized for communication to and/or analysis by the analytics system 9100.

In one exemplification, the perioperative data can be assembled on a procedure-by-procedure basis and uploaded by the surgical hubs 9000 to the analytics system 9100 for analysis thereby. The perioperative data indicates the manner in which the surgical hubs 9000 were programmed to operate or were manually controlled in association with a surgical procedure (i.e., the operational behavior of the surgical hubs 9000) because it indicates what actions the surgical hub 9000 took in response to various detected conditions, how the surgical hubs 9000 controlled the modular devices 9050, and what inferences the situationally aware surgical hubs 9000 derived from the received data. The analytics system 9100 can be configured to analyze the various types and combinations of preoperative, intraoperative, and post-operative data to determine whether a control program update should be generated and then push the update to the overall population or one or more sub-populations of surgical hubs 9000, as necessary.

Figure 19:
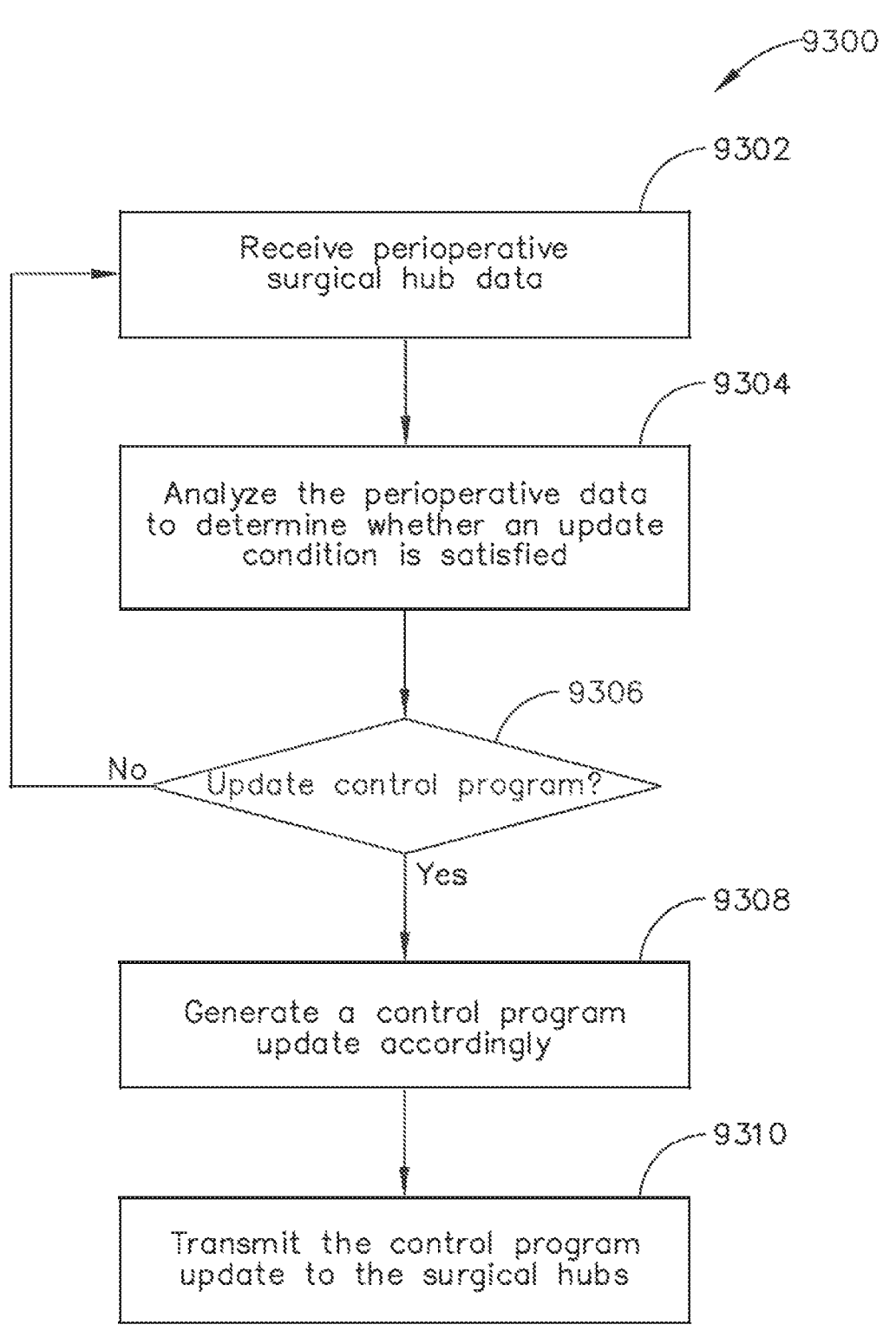
FIG. 19 illustrates a logic flow diagram of a process for updating the control program of a surgical hub, in accordance with at least one aspect of the present disclosure.

FIG. 19 illustrates a logic flow diagram of a process 9300 for updating the control program of a surgical hub 9000, in accordance with at least one aspect of the present disclosure. The process 9200 can be executed by, for example, one or more processors of the analytics servers 9070 of the analytics system 9100. In one exemplification, the analytics system 9100 can be a cloud computing system. For economy, the following description of the process 9300 will be described as being executed by the analytics system 9100; however, it should be understood that the analytics system 9100 includes processor(s) and/or control circuit(s) that are executing the describe steps of the process 9300.

The analytics system 9100 executing the process 9300 receives 9302 perioperative data from the surgical hubs 9000 that are communicably connected to the analytics system 9100. The perioperative data indicates the manner in which the surgical hubs 9000 are programmed to operate by their control programs or are controlled by the surgical staff during a surgical procedure. In some aspects, the perioperative data can include or being transmitted to the analytics system 9100 in association with surgical procedural outcome data. The surgical procedural outcome data can include data pertaining to an overall outcome of a surgical procedure (e.g., whether there was a complication during the surgical procedure) or data pertaining to a specific step within a surgical procedure (e.g., whether a particular staple line bled or leaked).

After an analytics system 9100 executing the process 9300 has received 9302 the perioperative data, the analytics system 9100 then analyzes 9304 the data to determine whether an update condition has been satisfied. In one exemplification, the update condition includes whether a threshold number or percentage of surgical hubs 9000 within the population exhibit a particular operational behavior. For example, the analytics system 9100 can determine that a control program update should be generated to automatically active an energy generator at a particular step in a type of surgical procedure when a majority of the surgical hubs 9000 are utilized to active the energy generator at that procedural step. In another exemplification, the update condition includes whether the rate of positive procedural outcomes (or lack of negative procedural outcomes) correlated to a particular operational behavior exceeds a threshold value (e.g., an average rate of positive procedural outcomes for a procedure step). For example, the analytics system 9100 can determine that a control program update should be generated to recommend that the energy generator be set at a particular energy level when the associated rate of hemostasis (i.e., lack of bleeding) at that energy level for the particular tissue type exceeds a threshold rate. In another exemplification, the update condition includes whether the rate of positive procedural outcomes (or lack of negative procedural outcomes) for a particular operational behavior is higher than the rate of positive procedural outcomes (or a lack of negative procedural outcomes) for related operational behaviors. In other words, if one subpopulation of surgical hubs 9000 exhibits a first operational behavior under a certain set of conditions and a second subpopulation of surgical hubs 9000 exhibits a second operational behavior under the same set of conditions, then the analytics system 9100 can determine whether to update the control programs of the surgical hubs 9000 according to whether the first or second operational behavior is more highly correlated to a positive procedural outcome. In another exemplification, the analytics system 9100 analyzes 9304 the data to determine whether multiple update conditions have been satisfied.

If an update condition has not been satisfied, the process 9300 continues along the NO branch and the analytics system 9100 continues receiving 9302 and analyzing 9304 perioperative data from the surgical hubs 9000 to monitor for the occurrence of an update condition. If an update condition has been satisfied, the process 9300 continues along the YES branch and the analytics system 9100 proceeds to generate 9308 a control program update. The nature of the generated 9308 control program update corresponds to the particular operational behavior of the surgical hub 9000 that is identified by the analytics system 9100 as triggering the update condition. In other words, the control program update adds, removes, or otherwise alters functions performed by the surgical hub 9000 so that the surgical hub US 2019/0206003 A1.

The surgical hub 9000 operates differently under the conditions that gave rise to the identified operational behavior. Furthermore, the type of control program update also depends upon whether the identified operational behavior results from manual control or control by the control program of the surgical hub 9000. If the identified operational behavior results from manual control, the control program update can be configured to provide warnings, recommendations, or feedback to the users based upon the manner in which they are operating the surgical hub 9000. For example, if the analytics system 9100 determines that taking a particular action or utilizing a particular instrument for a step in a surgical procedure improves outcomes, then the analytics system 9100 can generate 9308 a control program update that provides a prompt or warning to the surgical staff when the surgical hub 9000 determines that the designated step of the surgical procedure is occurring or will subsequently occur. Alternatively, the control program update can change one or more functions of the surgical hub 9000 from being manually controllable to being controlled by the control program of the surgical hub 9000. For example, if the analytics system 9100 determines that a display of the visualization system is set to a particular view by the surgical staff in a predominant number of surgical procedures at a particular step, the analytics system 9100 can generate a control program update that causes the surgical hub 9000 to automatically change the display to that view under those conditions. If the identified operational behavior results from the control program of the surgical hub 9000, then the control program update can alter how the control program functions under the set of circumstances that cause the identified operational behavior. For example, if the analytics system 9100 determines that a particular energy level for an RF electrosurgical or ultrasonic instrument correlates to poor or negative outcomes under a certain set of conditions, then the analytics system 9100 can generate 9308 a control program update that causes the surgical hub 9000 to adjust the energy level of the connected instrument to a different value when the set of conditions is detected (e.g., when the surgical hub 9000 determines that an arthroscopic procedure is being performed).

The analytics system 9100 then transmits 9310 the control program update to the overall population of surgical hubs 9000 or the subpopulation(s) of surgical hubs 9000 that are performing the operational behavior that is identified by the analytics system 9100 as triggering the update condition. In one exemplification, the surgical hubs 9000 are configured to download the control program updates from the analytics system 9100 each time an update is generated 9308 thereby. In one exemplification, the analytics system 9100 can thereafter continue the process 9300 of analyzing 9304 the data received 9302 from the surgical hubs 9000, as described above.

Figure 20:
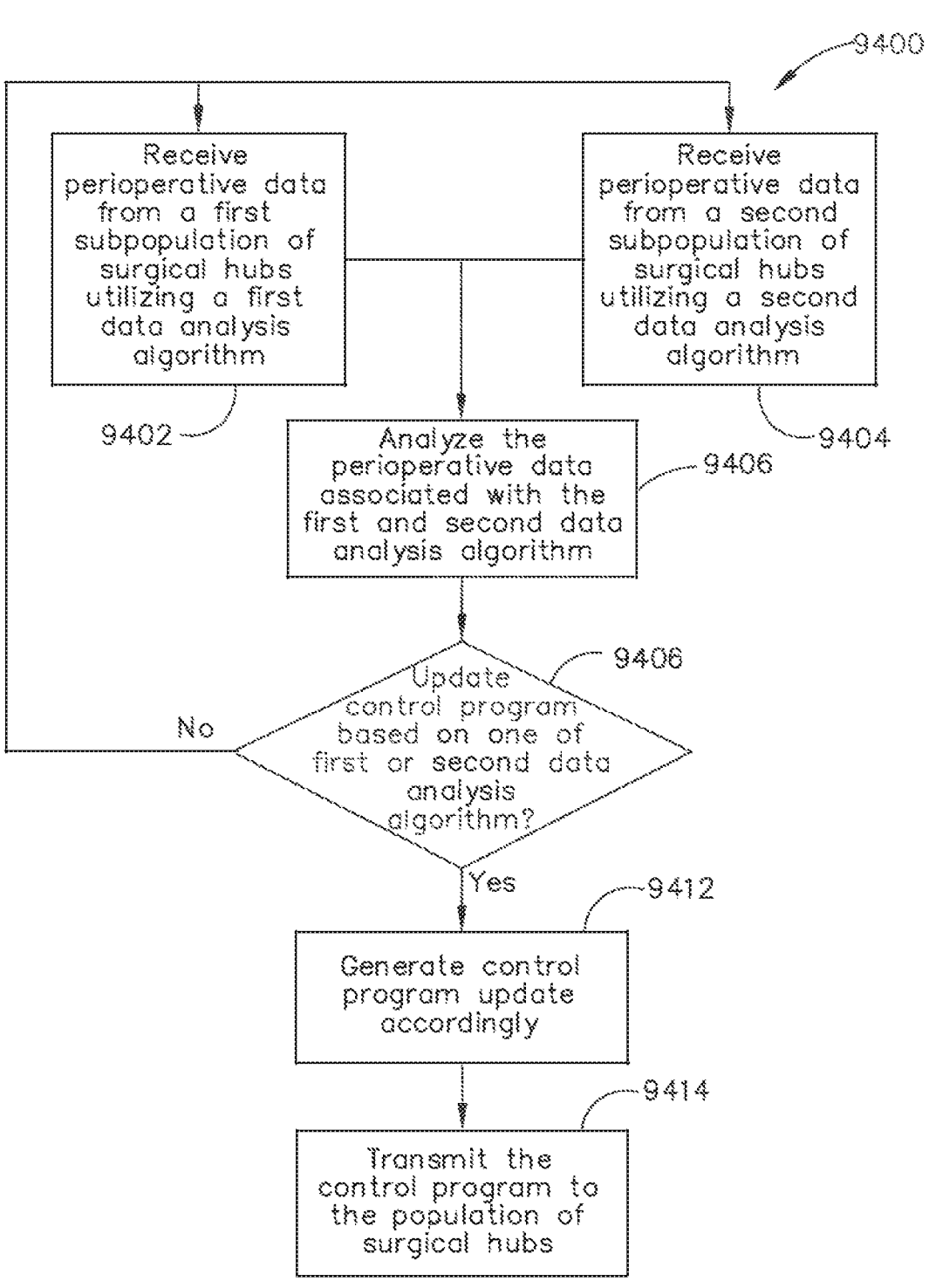
FIG. 20 illustrates a logic flow diagram of a process for updating the data analysis algorithm of a control program of a surgical hub, in accordance with at least one aspect of the present disclosure.

FIG. 20 illustrates a representative implementation of the process 9300 depicted in FIG. 19. FIG. 20 illustrates a logic flow diagram of a process 9400 for updating the data analysis algorithm of a control program of a surgical hub 9000, in accordance with at least one aspect of the present disclosure. As with the process 9300 depicted in FIG. 19, the process 9400 illustrated in FIG. 20 can, in one exemplification, be executed by the analytics system 9100. In one exemplification of the adaptive surgical system 9060 depicted in FIG. 18, the first surgical hub subpopulation 9312 is utilizing a first data analysis algorithm and the second surgical hub subpopulation 9314 is utilizing a second data analysis algorithm. For example, the first surgical hub subpopulation 9312 can be utilizing a normal continuous probability distribution to analyze a particular dataset, whereas the second surgical hub subpopulation 9314 can be utilizing a bimodal distribution for analyzing the particular dataset. In this exemplification, the analytics system 9100 receives 9402, 9404 the perioperative data from the first and second surgical hub subpopulations 9312, 9314 corresponding to the respective data analysis algorithms. The analytics system 9100 then analyzes 9406 the perioperative datasets to determine whether one of the perioperative datasets satisfies one or more update conditions. The update conditions can include, for example, a particular analysis method being utilized by a threshold percentage (e.g., 75%) of the surgical hubs 9000 in the overall population and a particular analysis method being correlated to positive surgical procedural outcomes in a threshold percentage (e.g., 50%) of cases.

In this exemplification, the analytics system 9100 determines 9408 whether one of the data analysis algorithms utilized by the first and second surgical hub subpopulations 9312, 9314 satisfies both of the update conditions. If the update conditions are not satisfied, then the process 9400 proceeds along the NO branch and the analytics system 9100 continues receiving 9402, 9404 and analyzing 9406 perioperative data from the first and second surgical hub subpopulations 9312, 9314. If the update conditions are satisfied, the process 9400 proceeds along the YES branch and the analytics system 9100 generates 9412 a control program update according to which of the data analysis algorithms the analysis 9406 determined satisfied the update conditions. In this exemplification, the control program update would include causing the surgical hub 9000 to utilize the data analysis algorithm that satisfied the update conditions when performing the corresponding analysis type. The analytics system 9100 then transmits 9414 the generated 9412 control program update to the population of surgical hubs 9000. In one exemplification, the control program update is transmitted 9414 to the entire population of surgical hubs 9000. In another exemplification, the control program update is transmitted 9414 to the subpopulation of surgical hubs 9000 that did not utilize the data analysis algorithm that satisfied the update conditions. In other words, if the analytics system 9100 analyzes 9406 the perioperative data and determines 9408 that the second (bimodal) data analysis method satisfies the update conditions, then the generated 9412 control program update is transmitted 9414 to the first subpopulation of surgical hubs 9000 in this exemplification. Furthermore, the control program update can either force the updated surgical hubs 9000 to utilize the second (bimodal) data analysis algorithm when analyzing the particular data set or cause the updated surgical hubs 9000 to provide a warning or recommend to the user that the second (bimodal) data analysis algorithm be used under the given conditions (allowing the user to choose whether to follow the recommendation).

This technique improves the performance of the surgical hubs 9000 by updating their control programs generated from data aggregated across the entire network of surgical hubs 9000. In effect, each surgical hub 9000 can be adjusted according to shared or learned knowledge across the surgical hub 9000 network. This technique also allows the analytics system 9100 to determine when unexpected devices (e.g., modular devices 9050) are utilized during the course of a surgical procedure by providing the analytics system 9100 with knowledge of the devices being utilized in each type of surgical procedure across the entire surgical hub 9000 network.

Figure 21:
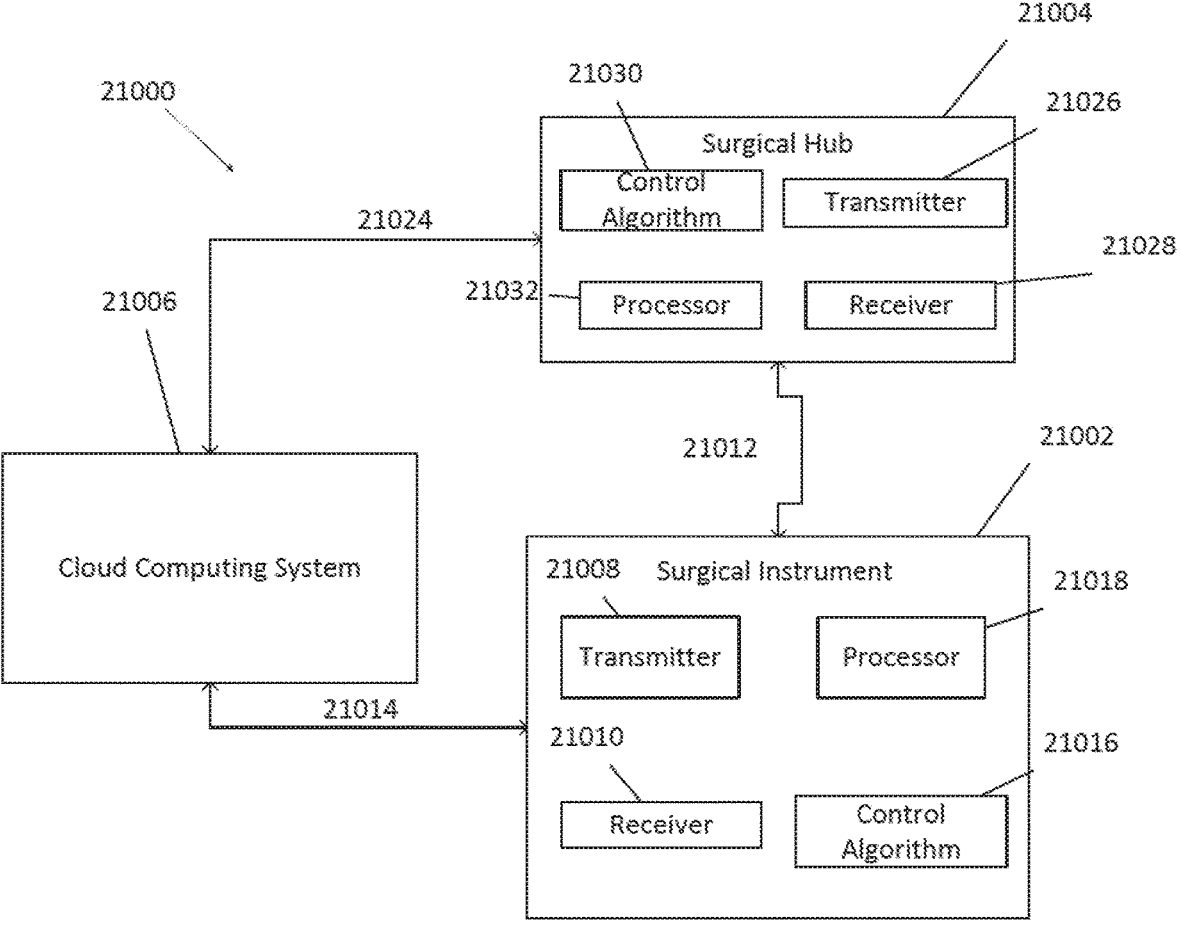
FIG. 21 illustrates a system for communication between a surgical instrument, a surgical hub, and a cloud computing system, in accordance with at least one aspect of the present disclosure.

FIG. 21 illustrates a system 21000 for communication between a surgical instrument 21002, a surgical hub 21004, and a cloud computing system 21006, in accordance with at least one aspect of the present disclosure. The surgical instrument 21002 may include a transmitter 21008 and a receiver 21010. The transmitter 21008 and a receiver 21010 may be configured to establish communication pathways 21012 and 21014 between at least one external device. For example, the communication pathway 21012 may be between the surgical instrument 21002 and the surgical hub 21004. The communication pathway 21014 may be between the surgical instrument 21002 and the cloud-computing system 21006. The surgical instrument 21002 may include a control algorithm 21016. The control algorithm 21016 may be updated based on new data received. The surgical instrument 21002 may include a processor 21018. The processor 21018 may update the control algorithm 21016. The control algorithm 21016 may perform a set of operations based on control parameters in the form of input data. The control algorithm 21016 may transmit the input data into output signals. The input data may be aggregated by the cloud computing system 21006, as described above. For example, the input data may be related to setup, EMR information, procedure information, and/or product mix usage. In some examples, the aggregated data may be related to compiled steps-of-use and/or procedure planning. In some examples, the aggregated data may be used to determine trends in outcomes, usage, and/or products. In some examples, the aggregated data is used as an education and process improvement system. Although FIG. 21 shows the surgical instrument 21002, it may also include the surgical instrument 112 (FIG. 1), the surgical instrument 600 (FIG. 8), the surgical instrument 7012 (FIG. 11), and/or the surgical instrument 6502 (FIG. 14).

The surgical hub 21004 may include a transmitter 21026 and a receiver 21028 that may be configured to establish the communication pathways between the surgical hub 21004 and at least one external device. For example, the communication pathway 21012 may be between the surgical hub 21004 and the surgical instrument 21002 and a communication pathway 21024 may be between the surgical hub 21004 and the cloud-computing system 21006. The surgical hub 21004 may include a control algorithm 21030 that may be updated based on new data received. The surgical hub 21004 may include a processor 21032 that may update the control algorithm 21030. Although FIG. 21 shows the surgical hub 21004, it may also include the surgical hub 205 (FIG. 5), the surgical hub 206 (FIG. 6), the surgical hub 5104 (FIG. 9), the surgical hub 7006 (FIG. 11), and/or the surgical hub 9000 (FIG. 13).

The cloud computing system 21006 may constitute a cloud-based analytics system and may including one or more networked computing resources. The cloud computing system 21006 may be communicatively coupled to the surgical hub 21004 via the communication pathway 21024 and to the surgical instrument 21002 via the communication pathway 21014. The cloud computing system 21006 may quickly and efficiently identify data based on specific criteria. In some situations, the cloud computing system 21006 may aggregate data determined from multiple surgical sites. The cloud computing system 21006 may handle the aggregated data by data sorting, prioritizing, and other types of data handling based on specific criteria or thresholds.

Although FIG. 21 shows the cloud computing system 21006, it may also include the analytics system 9100 described in FIG. 16.

Figure 22:
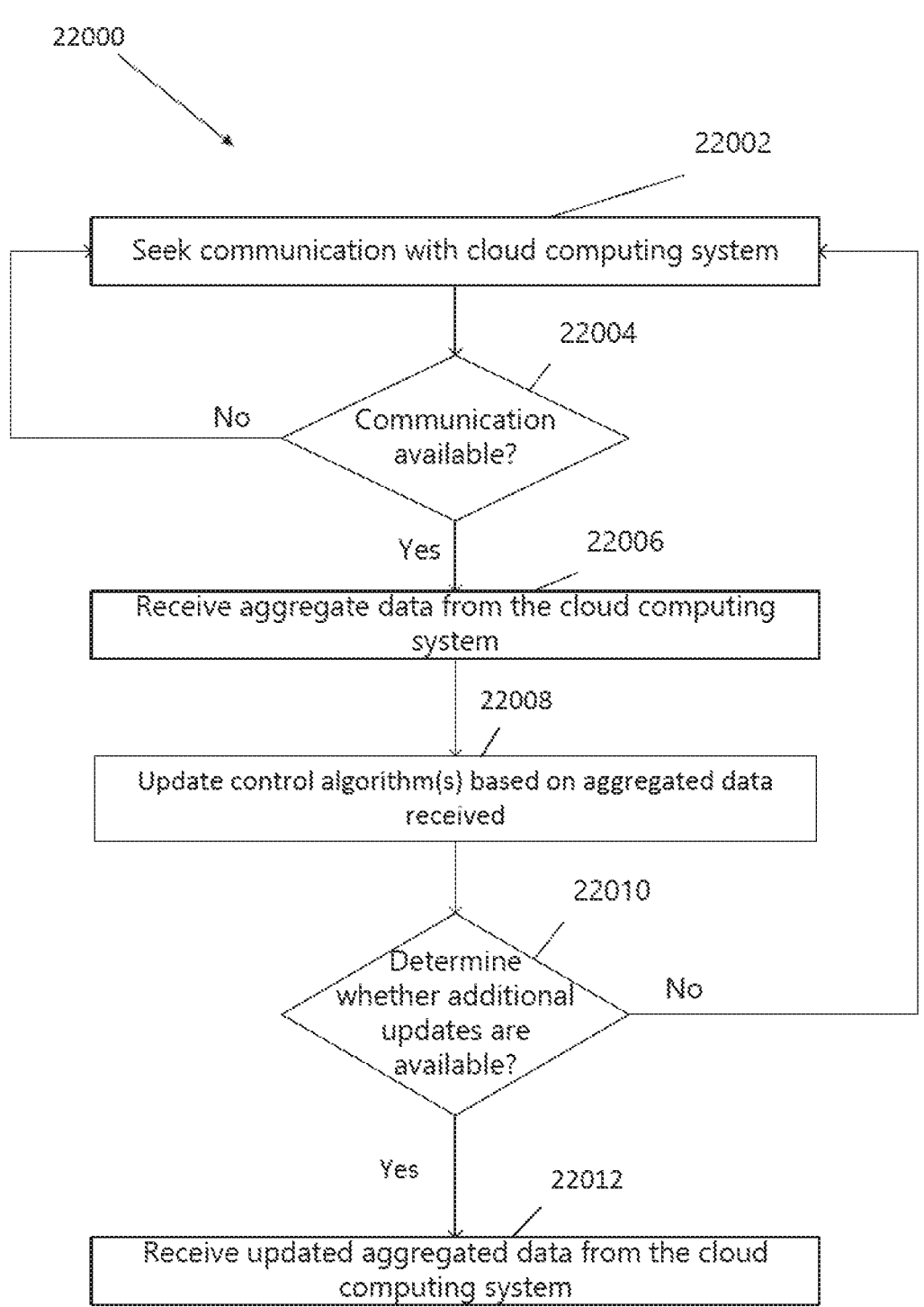
FIG. 22 illustrates a logic flow diagram of a process for updating the control algorithm of a surgical hub, in accordance with at least one aspect of the present disclosure.

FIG. 22 illustrates a logic flow diagram of a process 22000 for updating the control algorithm of the surgical hub 21004, in accordance with at least one aspect of the present disclosure. At 22002, the process 22000 may configure the surgical hub 21004 to seek communication with the cloud computing system 21006. The transmitter 21026 and the receiver 21028 may be configured to establish the communication pathway 21024 between the surgical hub 21004 and a cloud computing system 21006. For example, the transmitter 21026 of the surgical hub 21004 may send a communication request to the cloud computing system 21006. At 22004, the surgical hub 21004 may determine whether communication is available with the cloud computing system 21006. For example, the determination whether communication is available with the cloud computing system 21006 may be determined by system generation, software revision, system capabilities, types of interconnected devices, level of networking, data capacity, and/or power capacity. The cloud computing system 21006 may be configured to aggregate data from multiple surgical devices. If communication is not available, the surgical hub 21004 may be configured to operate in a default mode of operation if no communication is available with the cloud computing system and may seek communication with the cloud computing system 21006 at 22002 at a later time. If communication is available, at 22006, the surgical hub 21004 may receive the aggregate data from the cloud computing system 21006 via the receiver 21028. In some examples, the aggregated data may be related to setup, EMR information, procedure information, and/or product mix usage. In some examples, the aggregated data may be related to compiled steps-of-use and/or procedure planning. In some examples, the aggregated data may be used to determine trends in outcomes, usage, and/or products. In some examples, the aggregated data is used as an education and process improvement system. At 22008, the surgical hub 21004 may update one or more control algorithms based on the aggregated data received. At 22010, the surgical hub 21004 may determine whether additional updates are available from the cloud computing system 21006. If no additional updates are available, the surgical hub 21004 may seek communication with the cloud computing system 21006 at 22002, for example, at a later time. If additional updates are available, the surgical hub 21004, at 22012 may continue to communicate with the cloud computing system 21006 to receive additional updates, wherein the additional updates relate to updated aggregate data determined by the cloud computing system 21006. In some examples, the surgical hub 21004 can include the upgradeable element 3014 described above in FIG. 15B. The upgradeable element 3014 may act update the operational mode of the one or more control algorithms of the surgical hub 21004 based on the aggregated data received.

Figure 23:
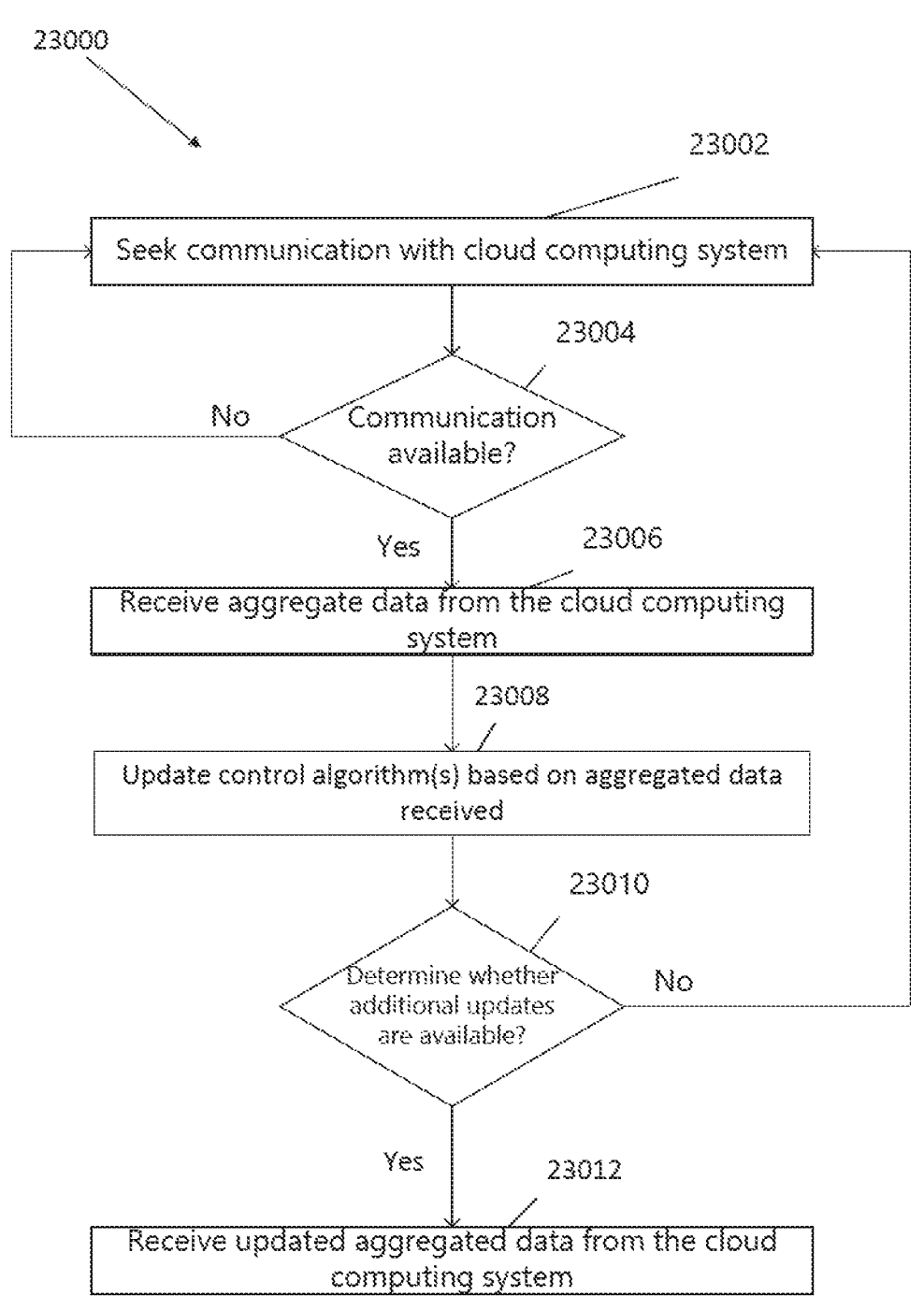
FIG. 23 illustrates a logic flow diagram of a process for updating the algorithm of a surgical instrument, in accordance with at least one aspect of the present disclosure.

FIG. 23 illustrates a logic flow diagram of a process 23000 for updating the algorithm of the surgical instrument 21002, in accordance with at least one aspect of the present disclosure. At 23002, the process 23000 may configure the surgical instrument 21002 to seek communication with the cloud computing system 21006. The transmitter 21008 and the receiver 21010 may be configured to establish a communication pathway between the surgical instrument 21002 and a cloud computing system 21006. For example, the transmitter 21008 of the surgical instrument 21002 may send a communication request to the cloud computing system 21006. At 23004, the surgical instrument 21002 may determine whether communication is available with the cloud computing system 21006. For example, the determination whether communication is available with the cloud computing system 21006 may be determined by system generation, software revision, system capabilities, types of interconnected devices, level of networking, data capacity, and/or power capacity. The cloud computing system 21006 may be configured to aggregate data from multiple surgical devices. If communication is not available, the surgical instrument 21002 may be configured to operate in a default mode of operation if no communication is available with the cloud computing system and may seek communication with the cloud computing system 21006 at 23002, for example, at a later time. If communication is available, at 23006, the surgical instrument 21002 may receive the aggregate data from the cloud computing system 21006 via the receiver 21010. In some examples, the aggregated data may be related to setup, EMR information, procedure information, and/or product mix usage. In some examples, the aggregated data may be related to compiled steps-of-use and procedure planning. In some examples, the aggregated data may be used to determine trends in outcomes, usage, and/or products. In some examples, the aggregated data is used as an education and process improvement system. At 23008, the surgical instrument 21002 may update one or more control algorithms based on the aggregated data received. At 23010, the surgical instrument 21002 may determine whether additional updates are available from the cloud computing system 21006. If no additional updates are available, the surgical instrument 21002 may seek communication with the cloud computing system 21006 at 23002, for example, at a later time. If additional updates are available, the surgical instrument 21002, at 23012 may continue to communicate with the cloud computing system 21006 to receive additional updates, wherein the additional updates relate to updated aggregate data determined by the cloud computing system 21006. In some examples, the surgical instrument 21004 can include the upgradeable element 3014 described above in FIG. 15B. The upgradeable element 3014 may act update the operational mode of the one or more control algorithms of the surgical instrument 21002 based on the aggregated data received.

Figure 24:
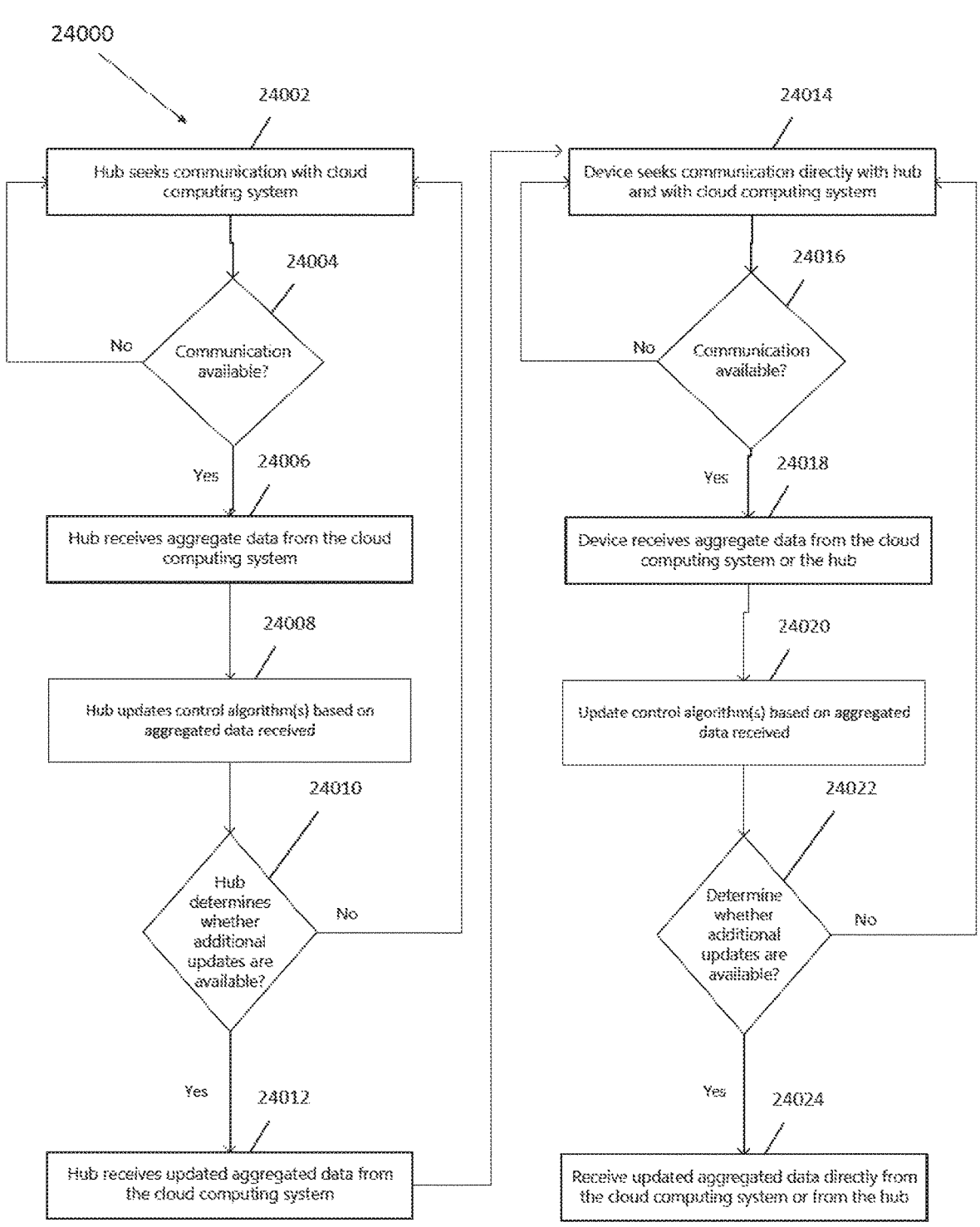
FIG. 24 illustrates a logic flow diagram of a process for updating a surgical system, in accordance with at least one aspect of the present disclosure.

FIG. 24 illustrates a logic flow diagram of a process 24000 for updating a surgical system, in accordance with at least one aspect of the present disclosure. At 24002, the process 22000 may configure the surgical hub 21004 to seek communication with the cloud computing system 21006. The transmitter 21026 and the receiver 21028 may be configured to establish a communication pathway between the surgical hub 21004 and a cloud computing system 21006. For example, the transmitter 21026 of the surgical hub 21004 may send a communication request to the cloud computing system 21006. At 24004, the surgical hub 21004 may determine whether communication is available with the cloud computing system 21006. For example, the determination whether communication is available with the cloud computing system 21006 may be determined by system generation, software revision, system capabilities, types of interconnected devices, level of networking, data capacity, and/or power capacity. The cloud computing system 21006 may be configured to aggregate data from multiple surgical devices. If communication is not available, the surgical hub 21004 may be configured to operate in a default mode of operation if no communication is available with the cloud computing system and may seek communication with the cloud computing system 21006 at 24002, for example, at a later time. If communication is available, at 24006, the surgical hub 21004 may receive the aggregate data from the cloud computing system 21006 via the receiver 21028. In some examples, the aggregated data may be related to setup, EMR information, procedure information, and/or product mix usage. In some examples, the aggregated data may be related to compiled steps-of-use and procedure planning. In some examples, the aggregated data may be used to determine trends in outcomes, usage, and/or products. In some examples, the aggregated data is used as an education and process improvement system. At 24008, the surgical hub 21004 may update one or more control algorithms based on the aggregated data received. At 24010, the surgical hub 21004 may determine whether additional updates are available from the cloud computing system 21006. If no additional updates are available, the surgical hub 21004 may seek communication with the cloud computing system 21006 at 24002, for example, at a later time. If additional updates are available, the surgical hub 21004, at 24012 may continue to communicate with the cloud computing system 21006 to receive additional updates, wherein the additional updates relate to updated aggregate data determined by the cloud computing system 21006. In some examples, the surgical system can include the upgradeable element 3014 described above in FIG. 15B. The upgradeable element 3014 may act update the operational mode of the one or more control algorithms of the surgical hub 21004 and/or the surgical instrument 21002 based on the aggregated data received.

After the surgical 21004 receives additional updates, at 24014, the process 24000 may configure the surgical instrument 21002 to seek communication with the surgical hub 21004 and/or directly with the cloud computing system 21006. The transmitter 21008 and the receiver 21010 may be configured to establish communication pathway between the surgical instrument 21002 and the surgical hub 21004 and a communication pathway between the surgical instrument 21002 and the cloud computing system 21006. For example, the transmitter 21008 of the surgical instrument 21002 may send a communication request to the surgical hub 21004 and/or to the cloud computing system 21006. At 24016, the surgical instrument 21002 may determine whether communication is available with the surgical hub 21004 and/or with the cloud computing system 21006. For example, the determination whether communication is available with the surgical hub 21004 and/or with the cloud computing system 21006 may be determined by system generation, software revision, system capabilities, types of interconnected devices, level of networking, data capacity, and/or power capacity. The surgical hub 21004 may be configured to store aggregated data received from the cloud computing system 21006. The cloud computing system 21006 may be configured to aggregate data from multiple surgical devices. If communication is not available, the surgical instrument 21002 may be configured to operate in a default mode of operation if no communication is available with the surgical hub 21004 or with the cloud computing system 21006 and may seek communication with the surgical hub 21004 or with the cloud computing system 21006 at 23002, for example, at a later time. If communication is available, at 24018, the surgical instrument 21002 may receive the aggregate data from the surgical hub 21004 or directly from the cloud computing system 21006 via the receiver 21010. In some examples, the aggregated data may be related to setup, EMR information, procedure information, and/or product mix usage. In some examples, the aggregated data may be related to compiled steps-of-use and procedure planning. In some examples, the aggregated data may be used to determine trends in outcomes, usage, and/or products. In some examples, the aggregated data is used as an education and process improvement system. At 24020, the surgical instrument 21002 may update one or more control algorithms based on the aggregated data received. At 24022, the surgical instrument 21002 may determine whether additional updates are available from the surgical hub 21004 or directly from the cloud computing system 21006. If no additional updates are available, the surgical instrument 21002 may seek communication with the surgical hub 21004 or with the cloud computing system 21006 at 24002, for example, at a later time. If additional updates are available, the surgical instrument 21002, at 24024 may continue to communicate with the surgical hub 21004 and/or the cloud computing system 21006 to receive additional updates, wherein the additional updates relate to updated aggregate data determined by the cloud computing system 21006.

The cloud computing system 21006 may provide data monitoring with monthly/quarterly reports, utilize data collected at unique sites compared to any national/regional/local area. The cloud computing system 21006 may provide recommendations to either reduce risk, improve safety, reducing operating time, and/or improve reduce total product usage. In one aspect, the cloud computing system 21006 may provide inventory control methods. For example, the cloud computing device 21006 may provide guidance based on demographic, utilization, and/or procedure type to optimize inventory. For example, at the end of a surgery, the cloud computing system 21006 may report all devices and cartridges used so individual hospitals can know what has been used and needs ordering. In one aspect, the cloud computing system 21006 can track of all the items disposed in a location to ensure items are placed in their current places.

The cloud computing system 21006 may provide a service that monitors surgery and offers reconfiguration of room layout and resources that can reduce surgical time/room use. For example, the cloud computing system 21006 can be linked to a system/app that give an instant answer, such as a mobile device app, regarding questions on device, procedure, and training. For example, the cloud computing system 21006 can provide access databases and message boards that can allow users to ask questions and see questions asked by others and the responses to those questions. In one aspect, the cloud computing system 21006 may provide a service based on the data that could create specific training programs tailored for best practices, which can be location specific.

The hub connectivity control parameter(s) may include, but not limited to, systems capabilities such as hardware capability, firmware capability and/or software capability. The hub connectivity control parameter(s) may include a consumer-controlled parameter, such as a subscription level. For example, a medical facility may purchase a subscription to hub connectivity capabilities. Some subscription level(s) may provide the hub access to surgical data gathered from external systems, while others may limit the hub connectivity to internal devices.

In an example hub connectivity mode, the surgical hub may receive information from surgical instrument(s) and may send the received information to a remote server (such as a remote processing server and/or a remote database in the cloud).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s). The surgical hub may record various surgical information and send surgical information to a remote server for archiving and/or analysis. The archived surgical information may be aggregated with information received from other surgical hub(s), and/or surgical information associated with other medical facilities. The aggregated information may be accessed to generate instructional information to one or more surgical instrument(s). In an example, the surgical communication hub may aggregate information, such as information received from smart surgical devices, information associated with multiple surgeries, surgical information and corresponding outcome associated with multiple patients. The aggregated information may be stored in a remote database. In an example, the surgical information may be aggregated at a remote server.

A surgical hub may obtain a hub connectivity mode based on a hub connectivity control parameter. For example, the hub connectivity mode may be selected from multiple connectivity modes that may be preconfigured, dynamically updated, semi-dynamically updated, periodically updated, or preset. The hub connectivity modes may control interdevice connectivity within a network associated with a hospital, and/or communication with an external network associated with a different hospital. The surgical hub may determine whether to provide instructional information to at least one smart surgical instrument based on the hub connectivity mode. On a condition that the hub connectivity mode does not support provisioning instructional information to surgical devices, provisioning instructional information to surgical devices may be disabled. On a condition that the hub connectivity mode supports provisioning instructional information to surgical devices, the surgical hub may determine to obtain and provide instructional information to surgical devices.

Figure 26:
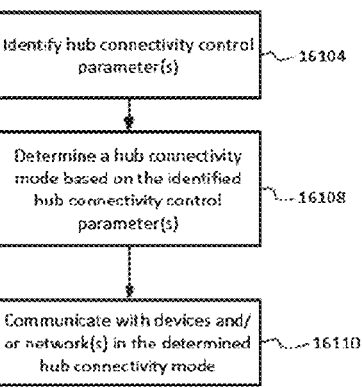
FIG. 26 illustrates an example flow for a hub operating under tiered communication modes.

FIG. 26 shows an example flow for a hub operating under tiered communication modes. At 16104, one or more hub connectivity control parameters may be identified. At 16108, a hub connectivity mode may be determined based on the identified hub connectivity control parameter(s). For example, the surgical hub 7006 shown in FIG. 11 may determine the hub connectivity mode based on a hub connectivity control parameter. The hub connectivity mode may be selected from multiple connectivity modes that may be preconfigured, dynamically updated, semi-dynamically updated, periodically updated, or preset. The hub connectivity modes may control inter-device connectivity within a network associated with a hospital, and/or communication with an external network associated with a different hospital, for example.

The hub connectivity control parameter(s) may include, but not limited to, systems capabilities such as hardware capability, firmware capability and/or software capability. For example, if a surgical instrument lacks the hardware capability to provide indications of instructional information, the surgical hub may switch to a connectivity mode that may disable providing instructional information to the surgical instrument.

The hub connectivity control parameter(s) may include a consumer-controlled parameter, such as a subscription level. For example, a medical facility may purchase a subscription to hub connectivity capabilities. Some subscription level(s) may provide the hub access to surgical data gathered from external systems, while others may limit the hub connectivity to internal devices.

The hub connectivity control parameter(s) may include available data bandwidth, power capacity and usage, processor and memory utilization, and/or internal or attached systems.

Figures 25A, 25B, 25C:
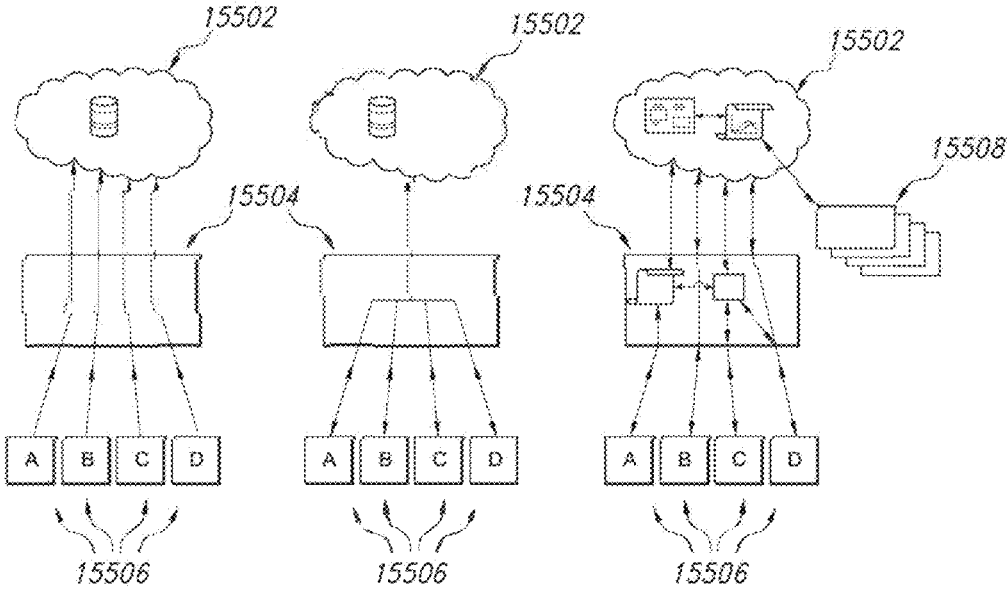
FIGS. 25A-C illustrate example hub connectivity modes.

The hub connectivity control parameter(s) may include an indication from a tiered system. The tiered system may scale the communication between the surgical hub 7006 and the device(s) 7012, the communication between the surgical hub 7006 and external server(s) 7013/7002 and/or the like, based on the available data bandwidth, power capacity and usage, processor and memory utilization, and/or internal or attached systems. The tiered system may determine max communication capabilities the surgical hub may operate under. For example, upon detecting the power capability associated with the operation room, associated with the surgical hub, and/or associated with a medical facility is below a threshold, the tiered system may scale down the surgical hub's connectivity capabilities. For example, upon detecting available data bandwidth is below a threshold, memory utilization is above a certain threshold, power usage is above a certain threshold, and/or other system conditions that may warrant scaling down the surgical hub's connectivity capabilities, the tiered system may limit or disable the communication between the surgical hub and the devices and/or the communication between the surgical hub and external server(s). For example, bi-directional connectivity mode (as shown in FIG. 25B) may be scaled down to flow-through connectivity mode (as shown in FIG. 25A). External communications (as shown in FIG. 25C) may be disabled. In examples, the tiered system may be a module within the surgical hub or may be a system external to the surgical hub.

At 16110, the surgical hub may communicate with devices in the operating room, servers in the internal and/or external network(s) in accordance with the determined hub connectivity mode.

In an example hub connectivity mode, the surgical hub may receive information from surgical instrument(s) and may send the received information to a remote server (such as a remote processing server and/or a remote database in the cloud).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s).

In an example connectivity mode, the surgical hub may receive information from surgical instrument(s) and may send the received information to a remote server (such as a remote processing server and/or a remote database in the cloud). The surgical hub may receive information from surgical instrument(s), obtain instructional information based on the information received from the surgical instrument(s), and may send the instructional information to one or more surgical instrument(s). The surgical hub may record various surgical information and send surgical information to a remote server for archiving and/or analysis. The archived surgical information may be aggregated with information received from other surgical hub(s), and/or surgical information associated with other medical facilities. The aggregated information may be accessed to generate instructional information to one or more surgical instrument(s). In an example, the surgical communication hub may aggregate information, such as information received from smart surgical devices, information associated with multiple surgeries, surgical information and corresponding outcome associated with multiple patients. The aggregated information may be stored in a remote database. In an example, the surgical information may be aggregated at a remote server.

FIGS. 25A-C illustrate example hub connectivity modes that a surgical hub, such as the surgical hub 7006 may operate under. As shown in FIGS. 25A-C, the surgical hub 15504 may communicate with the various devices 15506, remote server(s) in the cloud 15502 and/or devices, servers and databases in external networks 15508 in different connectivity modes.

FIG. 25C shows an example hub connectivity mode that supports data aggregation with external data sets. As shown, the surgical hub 15506 may receive surgical data from surgical device(s) 15506, and may send data, such as instructional information to device(s) 15506. The surgical hub 15504 may facilitate recording and archiving surgical data and may exchange surgical data and/or related analysis with an external network(s) 15508. Data from various hospitals or medical organizations 15508 can be aggregated. Surgical data, outcome, patient information can be compiled to determine instructional information, surgical recommendations, aggregation analysis, and/or the like. As shown, the surgical hub 15504 may retrieve aggregation analysis from remote server(s) or database(s) in the cloud 15502. The aggregation analysis may be used to generate instructional information for sending to surgical devices 15506.

Figure 27:
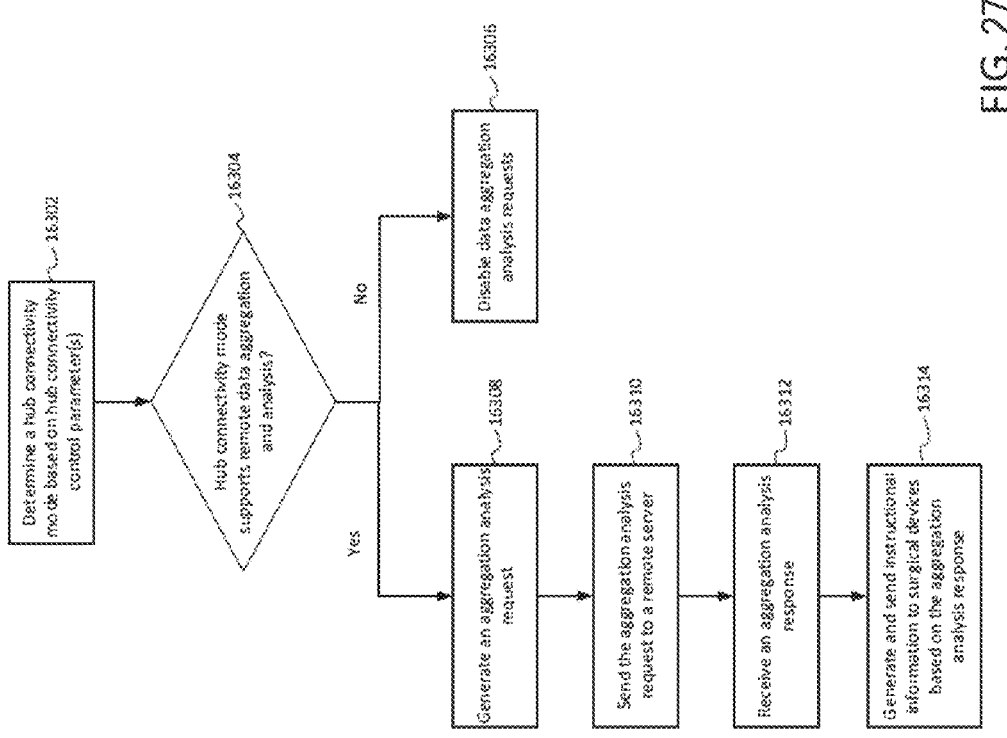
FIG. 27 illustrates an example flow for a hub operating under tiered communication modes.
Figure 28:
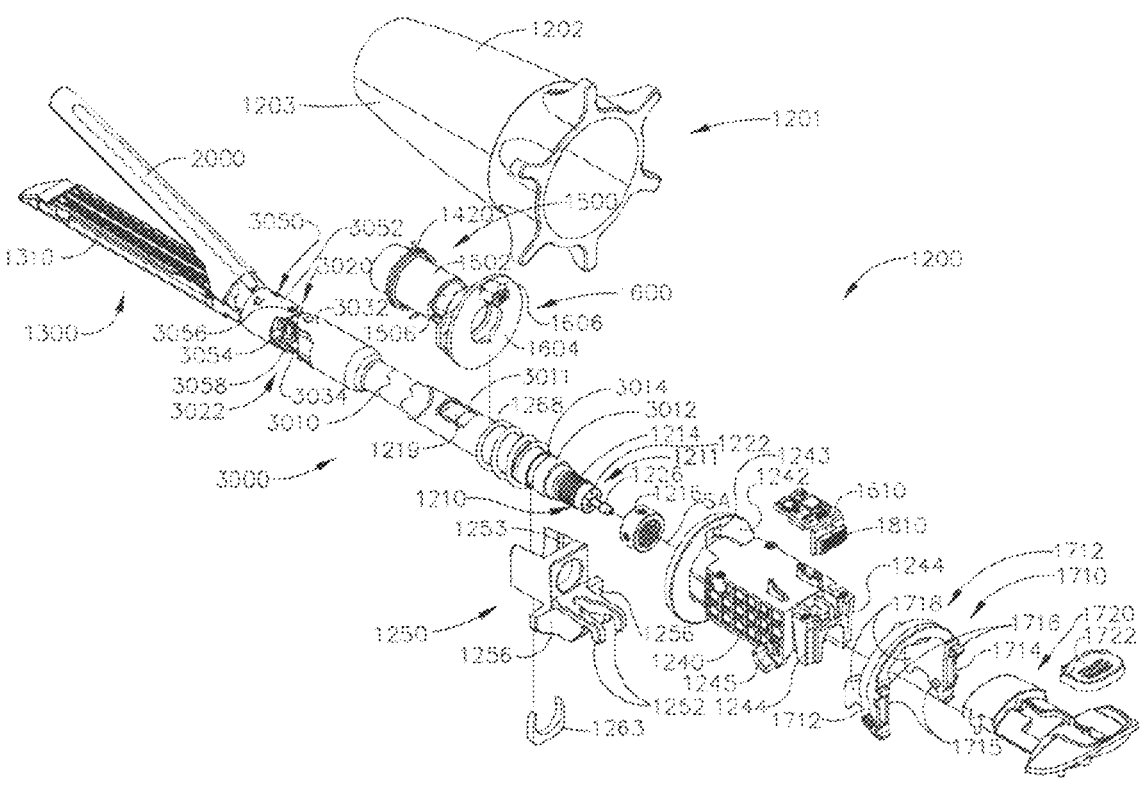
FIG. 28 is an exploded assembly view of an interchangeable surgical shaft assembly.
Figure 29:
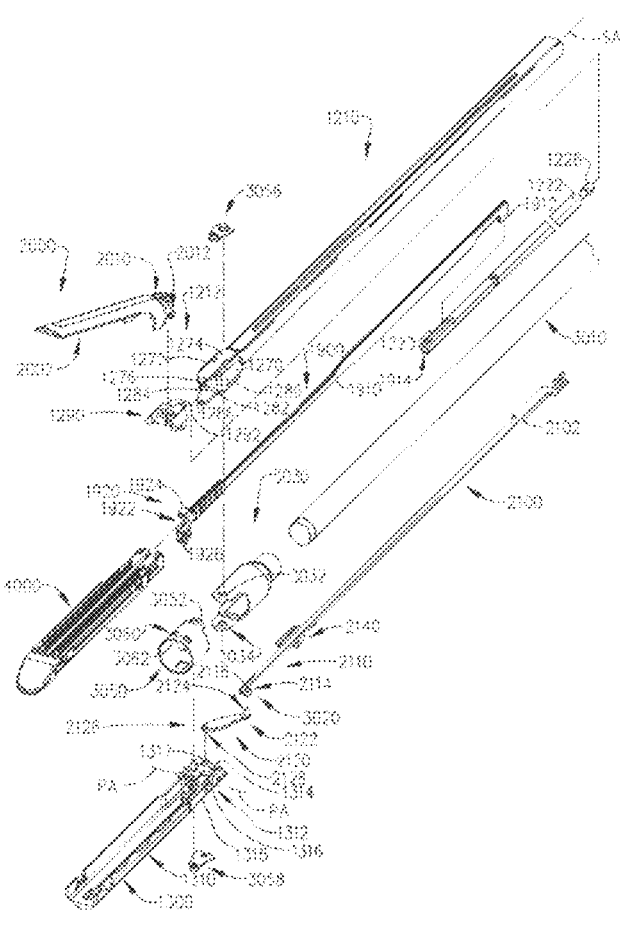
FIG. 29 is another partial exploded assembly view of a portion of the interchangeable surgical shaft assembly.
Figure 30:
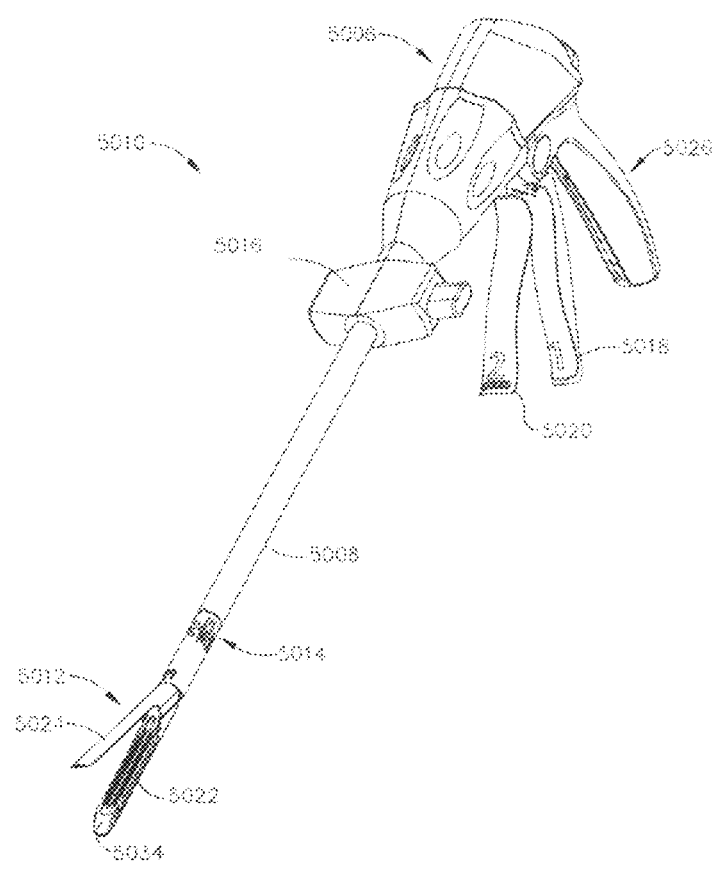
FIG. 30 is a perspective view of a surgical stapling system.
Figure 31:
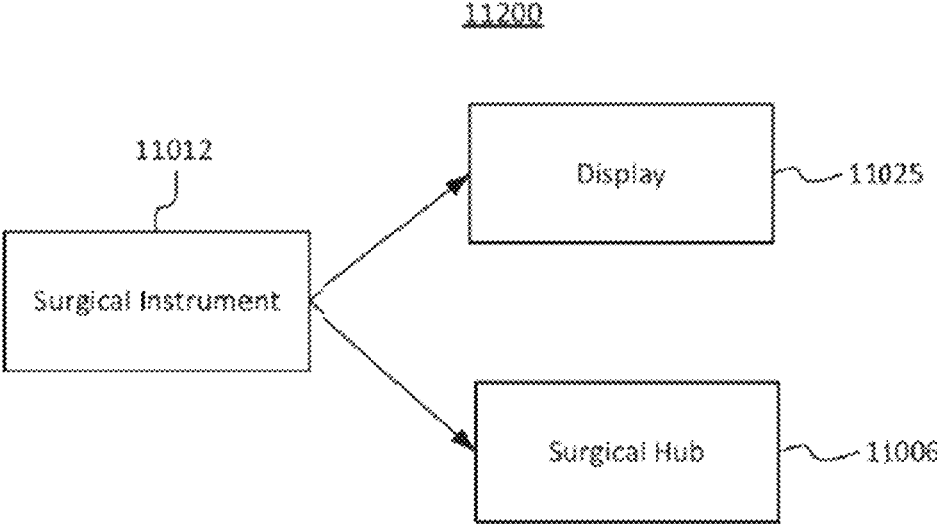
FIG. 31 illustrates an example surgical instruemnt operation mode.
Figure 32:
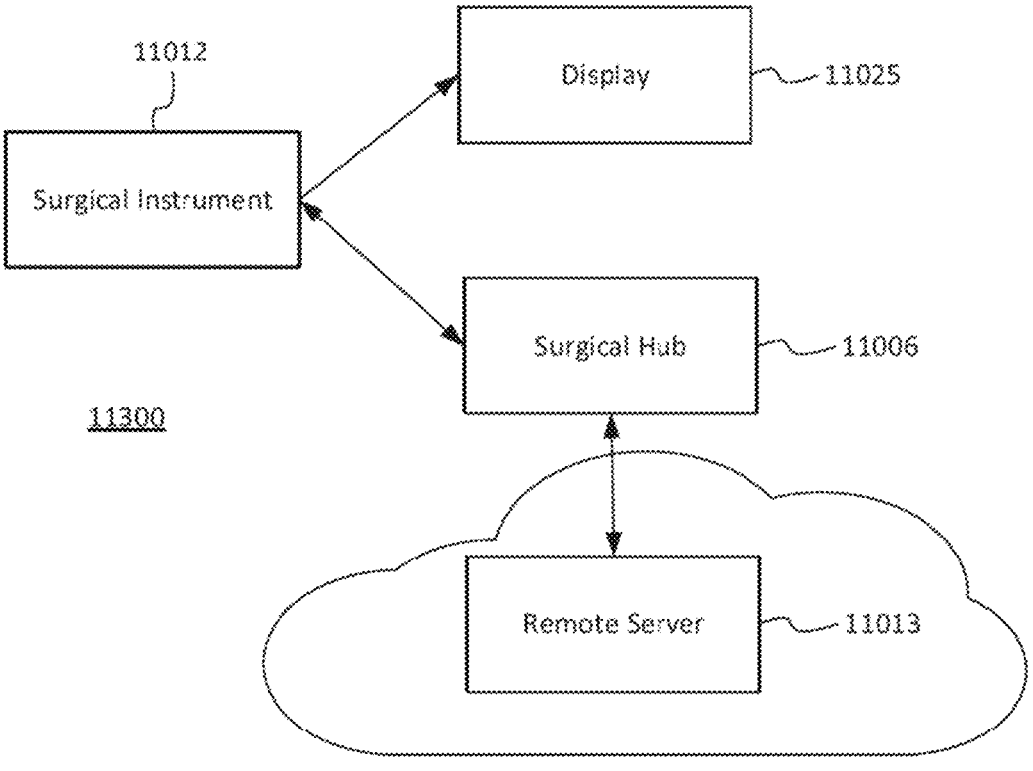
FIG. 32 illustrates an example surgical instruemnt operation mode.
Figure 33:
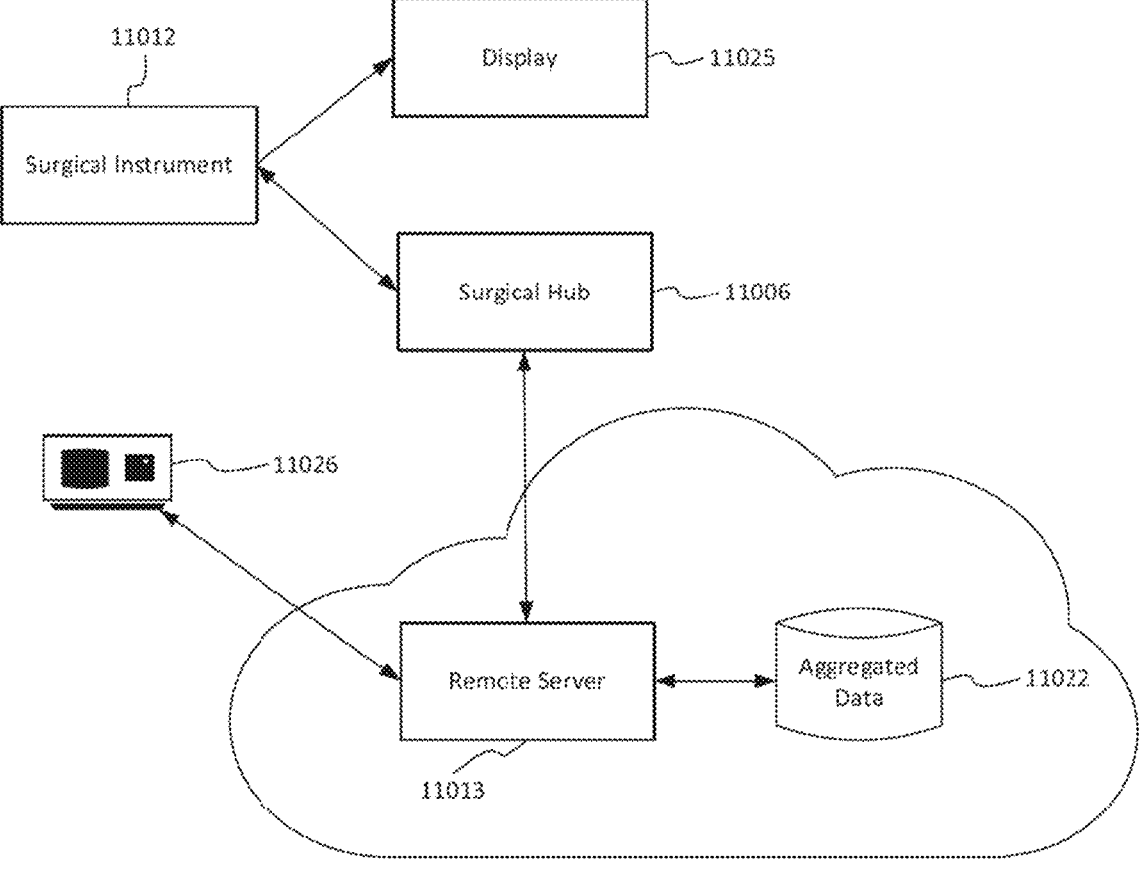
FIG. 33 illustrates an example surgical instruemnt operation mode.
Figure 34:
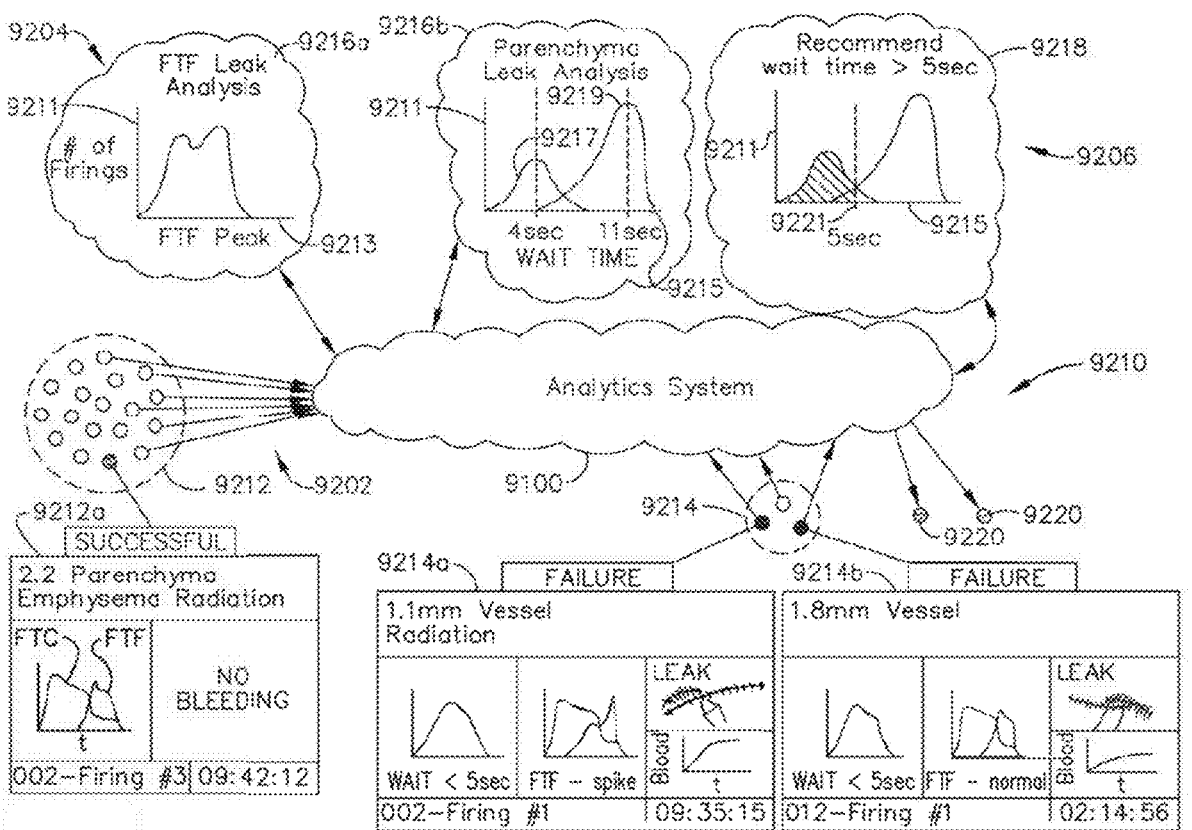
FIG. 34 is a diagram of an illustrative analytics system updating a surgical instrument control program, in accordance with at least one aspect of the present disclosure.
Figure 35:
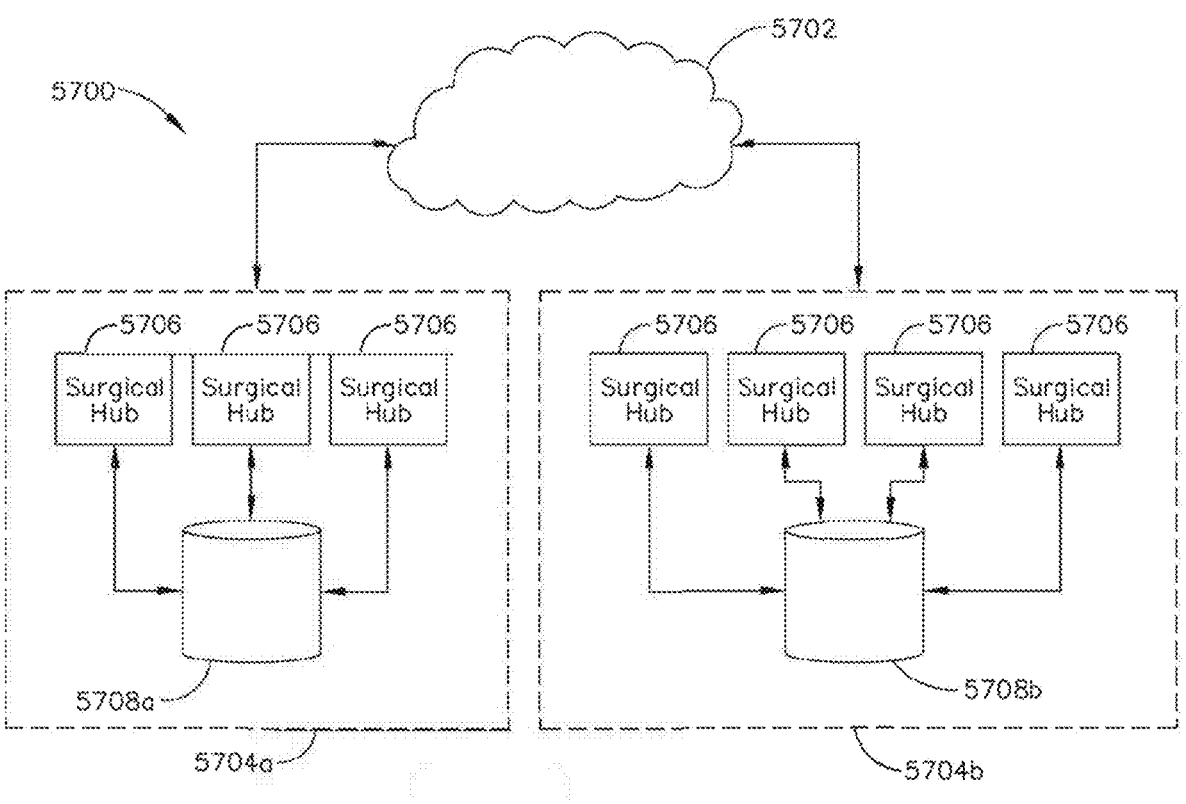
FIG. 35 is a block diagram of a computer-implemented interactive surgical system, in accordance with at least one aspect of the present disclosure.
Figure 36:
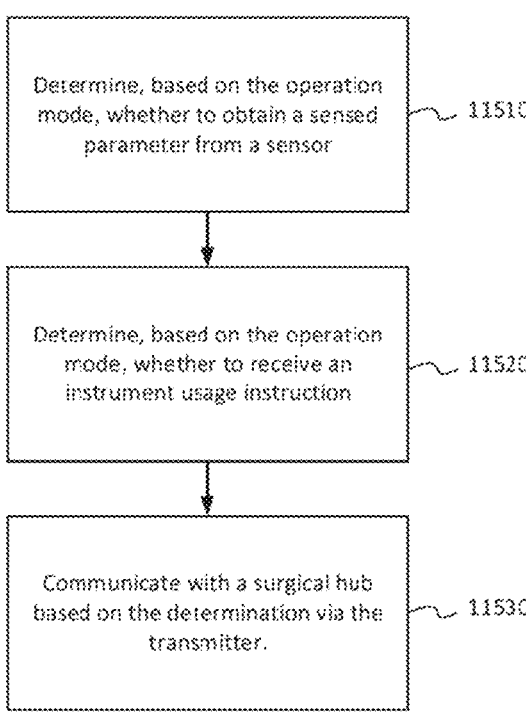
FIG. 36 illustrates an example flow for operating in accordance with surgical instrument operation mode(s).

When operating in a connectivity mode that allows external communication, the surgical hub may request information from a remote server and/or external systems. As shown in FIG. 27, at 16302, a hub connectivity mode may be determined based on the identified hub connectivity control parameter(s) as described herein. At 16304, the hub may determine whether to retrieve aggregation analysis from the remote server based on the hub connectivity mode. Based on a determination that the current hub connectivity mode supports remote data aggregation and analysis, at 16308, the surgical hub may generate an aggregation analysis request. The request may be generated based on the received surgical data and may be sent to a remote server at 16310. For example, the aggregation analysis request may indicate a request for recommendation on generator data associated with a particular step in a surgical procedure. In response, the surgical hub may receive an aggregation analysis response from the remote server at 16312.

For example, the aggregation analysis response may include a recommendation and/or a report. The aggregation analysis response may include one or more of: an energy mode of the generator for a particular surgical procedure, a power output of the generator for a particular surgical procedure, and/or a duration of the power output of the generator for a particular surgical procedure. The aggregation analysis response may include instructional information as described herein. At 16314, the surgical hub may generate and send instructional information to one or more surgical device(s) based on the received aggregation analysis response. As shown in FIG. 27, based on a determination that the current hub connectivity mode supports remote data aggregation analysis, the surgical hub may disable data aggregation analysis requests at 16306.

The powered surgical device may operate under various multi-display control modes such as one-way communication mode, sterile field display-based control mode, and/or remote aggregation analysis mode.

For example, when operating in an example remote aggregation analysis mode, surgical instrument may request aggregation analysis from a remote server (e.g., via the surgical hub). The surgical instrument may determine, based on the current multi-display control mode, whether to request aggregation analysis from a remote server (e.g., via the surgical hub). Based on a determination to request the aggregation analysis, an aggregation analysis request may be generated. An aggregation analysis response may be received and combined with surgical data generated based on the sensed surgical data for displaying on the display inside the surgical sterile field.

The surgical hub may operate under various multi-display control modes such as one-way communication mode, sterile field display-based control mode, and/or remote aggregation analysis mode.

For example, when the current hub connectivity mode is a bi-directional mode, the surgical hub may determine to obtain and provide instructional information. An example bidirectional connectivity mode may enable situational awareness and controlling surgical device(s). The surgical hub may infer progression of the surgical procedure from the surgical data and may obtain instructional information based on the inferred progression of the surgical procedure. The surgical hub may assess a surgical activity performed by an end effector of the modular surgical device at the surgical site from the data extracted from the at least one image frame.

A processor in a surgical instrument may determine whether to allow or restrict bi-directional communication. An initialized mode of communication may be treated differently than an operational mode of communication. For example, a first mode of operation may include unidirectional communication (e.g., from an instrument to a hub), a second mode of operation may include bi-directional communication, and a third mode of operation may include interactive communication (e.g., with a local hub or other remote network portal).

FIGS. 43-45 show examples of three modes (e.g., tiers) of operation of a surgical instrument. Other examples may implement more or fewer tiers/modes with the same or different operational characteristics. Various levels/modes/tiers of instrument operation may vary the availability, access, level of use, level of interaction and/or support for one or more features available through an instrument, such as sensors, communications, displays, storage, analyses, feedback, recommendations or advice, and so on. In examples, an instrument processor may be configured to determine an operation mode, for example, based on an instrument operation control parameter (e.g., one or more of a system capacity parameter, a system condition parameter, a system authorization parameter, a tiered communication mode indication received from a hub, and/or a tiered communication mode indication received from a remote server).

FIG. 43 illustrates an example surgical instrument operation mode. FIG. 43 shows an example of a first mode of operation (e.g., tier I). Surgical instrument 11012 may, in an example of a first mode of operation, engage in unidirectional communication with surgical hub 11006 and provide information for display to display 11025. A processor in surgical instrument 11012, such as a surgical stapler, may obtain cartridge information (e.g., identification and/or authentication information), cartridge authentication information, status information (e.g., firing status information), error information, and so on. Cartridge information may include, for example, cartridge identification information (e.g., color, type, length, serial number, etc.), and/or cartridge authentication information (e.g., verified origin, lot information, etc.). Status information may include an instrument status (e.g., ready, fired, connected, etc.). Error information may include instrument or accessory (e.g., cartridge) errors (e.g., unable to read cartridge parameter, etc.). The surgical instrument 11012, such as a surgical stapler, may send the cartridge identification information, cartridge authentication information, status information, error information, and/or other information, for example, to surgical hub 11006 and/or to display 11025 (e.g., for display to a user). Information may be sent, for example, via a (e.g., wireless) transmitter (e.g., Bluetooth).

In an example, first mode (e.g., tier I) information may indicate a powered endocutter was fired with a cartridge of a particular color, and the cartridge may be associated with a serial number. Such information may be used to annotate a procedure, for example, to describe how the powered endocutter was used. For example, an instrument processor may be configured to obtain staple cartridge information and instrument status information from an end effector (e.g., for removably storing a surgical staple cartridge). The instrument processor may send the cartridge information and the instrument status information to the surgical hub.

FIG. 44 illustrates an example surgical instrument operation mode. FIG. 44 shows an example of a second mode of operation (e.g., tier II). Surgical instrument 11012 may, in an example of a second mode of operation, engage in bidirectional communication with surgical hub 11006 and provide information to display 11025 (e.g., for display to a user). Surgical hub 11006 may communicate with remote server 11013. A second mode of operation may build on (e.g., add capabilities or functionality to) first mode operation.

Examples of bi-directional communication may include, for example, sensed information from the end effector (e.g., sensed parameter(s), such as tissue thickness), sensed information from the handle (e.g., motor function, force to fire/close, etc.), usage information (e.g., time from clamp to fire, characterization of user controlled firing, etc.), prioritization of information to display, location to display information, compiled recommendations from database analysis, etc. Information may be communicated, for example, locally to/from (e.g., within) an operating room (OR) and/or to/from one or more systems outside the OR (e.g., cloud-based storage, etc.).

FIG. 48 illustrates an example flow for operating in accordance with surgical instrument operation mode(s). In an example, a surgical instrument may include a processor, a transmitter and at least one sensor configured to provide a sensor signal (e.g., according to a physiological parameter of a tissue). The processor may be configured to make one or more determinations and/or take one or more actions based on an instrument operation mode.

At 11510, a determination may be made, based on the operation mode, whether to obtain a sensed parameter from a sensor. For example, a processor (e.g., in a surgical instrument) may determine (e.g., based on an instrument operation mode), whether to obtain (e.g., and/or send) a sensed parameter associated with a sensor signal from a sensor.

One or more sensors may sense and provide (e.g., in sensor signals) information, for example, from one or more portions (e.g., components or subcomponents) of a surgical instrument (e.g., a handle, an end effector, a knife, and/or a clamp). For example, a multitude of sensors are shown (e.g., in FIG. 40) and described in a surgical instrument comprising an adaptive control system in U.S. patent application Ser. No. 16/361,793, entitled "SURGICAL INSTRUMENT COMPRISING AN ADAPTIVE CONTROL SYSTEM," filed Mar. 22, 2019, now U.S. Patent Application Publication No. 20190314015, which is hereby incorporated herein by reference in its entirety. Sensed information from the handle may include, for example, a motor function, a force to fire/close, etc.

A sensor may be configured to sense and provide a sensor signal according to a physiological parameter of a tissue. For example, a surgical instrument may have a tissue thickness sensing module with a sensor that generates a sensor signal (e.g., tissue thickness signal) according to a physiological parameter of a tissue (e.g., tissue thickness), e.g., as shown and described with respect to FIGS. 7-15 in U.S. Pat. No. 9,345,481 and U.S. patent application Ser. No. 13/800,067, now U.S. Patent Application Publication No. 2014/0263552. In an example, a surgical instrument (e.g., an endocutter or surgical stapler) may include a tissue thickness sensing module, which may be located, for example, adjacent to the distal end of a staple cartridge. A tissue thickness sensing module may comprise a sensor and a controller. A sensor may be configured to generate a sensor signal, for example, a tissue thickness signal indicative of a thickness of the tissue (e.g., for tissue located between the anvil and the staple cartridge of an end effector portion of a surgical instrument). A controller may be in signal communication with the sensor. The controller may comprise a means for identifying the staple cartridge type of the staple cartridge. The staple cartridge type and the thickness of the tissue may be used, for example, to determine if the thickness of the tissue located between the anvil and the staple cartridge is within the optimal tissue thickness range of the staple cartridge.

In examples, a display or analysis (e.g., at a hub or remote server) may (e.g. interactively) combine sensed information with other information. For example, cartridge data may be interactively combined with instrument actuator or configuration data, e.g., to provide a broader understating of the (e.g., full) instrument status. Cartridge data can correspond to the size or type of staple being fired by the instrument, for example. Different types of staples may be utilized for different types of tissues. Usage information (e.g., time from clamp to fire, characterization of user-controlled firing, etc.) may be displayed and/or processed, for example, in combination with sensed information and/or other information.

At 11520, a determination may be made, based on the operation mode, whether to receive information (e.g., instrument usage instruction, operational information, and/or recommendations). For example, a processor (e.g., in a surgical instrument) may determine (e.g., based on an instrument operation mode), whether to receive information (e.g., from hub 11006 or remote server 11013 via surgical hub 11006).

Information received may include, for example, identification of the tissue to be operated on or that is being operated on (e.g., based on instrument or component position tracking information). See, for example. FIG. 40 and accompanying discussion in U.S. patent application Ser. No. 16/361,793, now U.S. Patent Application Publication No. 2019/0314015, which shows multiple sensors that may be used in a tracking system. A tracking procedure performed by the tracking system may be performed at a hub (e.g., surgical hub 11006). A processor in the instrument may receive position information from a tracking procedure at the hub.

Information received may include, for example, recommended usage information (e.g., time from clamp to fire, characterization of user-controlled firing, etc.). Information received may include, for example, force-to-fire, wait time/ period, speed, time from clamp to fire, etc. Information received may include, for example, information for display and/or information indicating whether to display on one or more displays (e.g., a display on the handle of an instrument, a display associated with a hub or other display system), prioritization of information to display, location (e.g., on one or more display screens) in which to display information, etc. Information received may include instructions determined based on, for example, sensed information, a disease state of the issue, previous firings of a surgical instrument or device (e.g., an endocutter) and associated sensed information, etc. Information received may include, for example, a cartridge selection sequence/order.

Information received may include a recommendation to the surgeon, if another available stapler, another available energy device, and/or another stapler component (e.g., staple cartridge, shaft, etc. available for use with the selected stapler/device) is more optimal or optional. Information received may include a warning that a safety issue exists with the selected cartridge, or stapler/device. Examples of recommendations based on safety systems are described in detail in U.S. patent application Ser. No. 16/024,075, entitled "SAFETY SYSTEMS FOR SMART POWERED SURGICAL STAPLING," filed on Jun. 29, 2018, now U.S. Patent Application Publication No. 2019/0201146, which is hereby incorporated herein by reference in its entirety.

Information received may include, for example, situation awareness information. The recommendation may be indicated with an elevated priority level based on an anticipated surgical act and the input from the situationally-aware surgical hub. For example, organ issue (e.g., stomach, lung, and so on) may be identified based on sensed information. A determination may be made based on sensed information, such as texture and/or compressibility (e.g., stomach tissue is very thick and very incompressible while lung tissue is very thick and very compressible). A clamping operation recommendation (e.g., speed and timing) and a firing operation recommendation (e.g., speed and timing, such as a wait period) may be determined, for example, based on tissue identification.

Examples of recommendations based on situation awareness are presented with respect to FIGS. 9 and 10. FIG. 9 is a diagram of an example situationally aware surgical system. FIG. 10 illustrates an example timeline of an illustrative surgical procedure and the inferences that the surgical hub can make from the data detected at each step in the surgical procedure. Other examples of recommendations based on situation awareness are disclosed in U.S. patent application Ser. No. 16/182,246, entitled "ADJUSTMENTS BASED ON AIRBORNE PARTICLE PROPERTIES," filed on Nov. 6, 2018, now U.S. Patent Application Publication No. 2019/ 0204201, which is hereby incorporated herein by reference in its entirety.

At 11530, communication may occur (e.g., via an instrument transmitter) with a surgical hub based on the determination at 11510 or 11520. Communications involving a surgical instrument (e.g., in second mode/tier operation)

may include sending and/or receiving information (e.g., as shown by example in FIG. 44) using, respectively, a transmitter and/or a receiver. In examples, an instrument processor may be configured to obtain and send a sensed parameter to a surgical hub, for example, based on a determination that the instrument operation mode supports obtaining the sensed parameter. In examples, an instrument processor may be configured to receive an instrument usage instruction from the surgical hub via a receiver, for example, based on a determination that the instrument operation mode supports receiving the instrument usage instruction. The instrument processor may send the received instrument usage instruction to a display. In examples, an instrument processor may be configured to receive cartridge information from an end effector. The instrument processor may determine, based on the instrument operation mode, whether to combine the cartridge information with an instrument usage parameter (e.g., a time from clamp to fire and/or a characterization of a user-controlled firing). The instrument processor may, based on a determination that the instrument operation mode supports this capability, send the instrument usage parameter with the cartridge information to the surgical hub (e.g., via the transmitter).

FIG. 45 illustrates an example surgical instrument operation mode. FIG. 45 shows an example of a third mode of operation (e.g., tier III). Surgical instrument 11012 may, in an example of a third mode of operation, engage in bidirectional communication with surgical hub 11006 and provide information to display 11025 (e.g., for display to a user). Surgical hub 11006 may communicate with remote server 11013. Remote server 11013 may communicate with storage 11022 storing aggregated data. Remote server 11013 may communicate with a user portal 11026.

A third mode of operation may build on (e.g., add capabilities or functionality to) first and second modes of operation described herein. In some examples, a third mode of operation may add cloud storage of instrument usage, user accessibility, data aggregation, analyses and recommendations. For example, an instrument processor may be configured to determine (e.g., based on a mode of operation) whether to send information (e.g., instrument accessory information, such as cartridge data) that may be interactively combined (e.g., by a remote/cloud server) with instrument actuator or configuration data (e.g., for aggregation). Information that may be stored and aggregated (e.g., with instrument usage information) may include, for example, one or more of the following: doctor identification information, type of surgery, patent information, or disease state. An instrument processor may be configured to send information to a hub and/or (e.g., directly) to a remote server.

An instrument processor may be configured to determine (e.g., based on a mode of operation) whether to receive a recommendation (e.g., an instrument usage recommendation and/or an accessory selection recommendation) based on stored information (e.g., aggregated historic/typical instrument usage information). For example, a recommendation may be recommended instrument usage information (e.g., stapler cartridge selection) generated based on aggregated historical instrument usage data. For example, a recommendation may be a stapler cartridge selection recommendation generated based on aggregated cartridge usage data associated with a procedural step (e.g., of using an instrument).

Historical information stored, aggregated, analyzed and used for recommendations may include, for example, information about previous procedures, such as procedure types, tissues, tissue conditions, accessory (e.g., cartridge) types selected and order of use in surgical instrument (e.g., surgical stapler), and so on. In various examples, historical information may include one or more of the following: compiled recommendations from database analysis (e.g., based on aggregated data); surgeon identification information (e.g., Dr. X); procedure information (e.g., bariatric procedure type); surgeon's usage information (e.g., trend, prediction, typical use), cartridge selection sequence/order; and/or display utilization (e.g. on an instrument handle or on a hub display/display system).

A remote server may aggregate data from multiple surgeries and users (e.g., surgeons). A remote server may send aggregated data and/or usage recommendations to a surgical instrument (e.g., directly or via a hub). A remote server may allow a user to review, aggregate, or use stored data to provide insights for future uses of an instrument (e.g., a surgical stapler).

A third mode/tier of instrument operation may provide a user (e.g., a surgeon) access to historical data (e.g., their own data). A surgeon may change a procedure over time (e.g., change cartridge selection of type(s), combination and sequence). A cartridge may be color coded, for example, to indicate staple heights (e.g., gray, white, blue, green, gold, or gold, green and black). Different staple heights may be used to staple tissue, for example, based on one or more variables, such as a type of tissue, a state of tissue, and/or a gap between tissue.

We claim:

1. A surgical hub operating within a surgical system, the surgical hub comprising:

a transmitter and a receiver configured to establish a communication pathway between the surgical hub and a cloud computing system; and a processor configured to:

determine to operate in a connectivity mode of a plurality of connectivity modes based on a connectivity control parameter;

based on a determination to operate in a first connectivity mode of the plurality of connectivity modes, enable uni-directional communication with the cloud computing system and one or more surgical instruments;

based on uni-directional communication with the one or more surgical instruments being enabled, receive surgical information from the one or more surgical instruments;

based on a determination to operate in a second connectivity mode of the plurality of connectivity modes, enable bi-directional communication with the cloud computing system and the one or more surgical instruments;

based on bi-directional communication with the cloud computing system being enabled, send, to the cloud computing system, an aggregation analysis request, wherein the aggregation analysis request includes a request for aggregated data;

receive, in response to the aggregate analysis request via the cloud computing system, the aggregated data determined from multiple surgical sites;

update one or more surgical hub control algorithms based on the aggregated data received;

based on bi-directional communication with the cloud computing system and the one or more surgical instruments being enabled, infer progression of a surgical procedure from the aggregated data;

based on the inferred progression of the surgical procedure, generate instructional information;

send the instructional information to at least one surgical instrument operating within the surgical system;

based on a determination to operate in a third connectivity mode of the plurality of connectivity modes, enable interactive communication with the cloud computing system and the one or more surgical instruments;

based on interactive communication with the cloud computing system being enabled, send, to the cloud computing system, a surgical recommendation request;

receive, in response to the surgical recommendation request via the cloud computing system, a surgical recommendation based on the aggregated data determined from the multiple surgical sites; and continue to communicate with the cloud computing system to receive additional updates, wherein the additional updates relate to updated aggregate data determined by the cloud computing system.

2. The surgical hub of claim 1, wherein the processor is further configured to:

determine trends in at least one of outcomes, usage, or products from the aggregated data, wherein the surgical hub control algorithms are updated based on the trends.

3. The surgical hub of claim 1, wherein the processor is further configured to:

determine information related to at least one of setup, EMR information, procedure information, or product mix usage based on the aggregated data, wherein the surgical hub control algorithms are updated based on the information related to at least one of setup, EMR information, procedure information, or product mix usage.

4. The surgical hub of claim 1, wherein the processor is further configured to:

determine information related to at least one of compiled steps-of-use or procedure planning based on the aggregated data, wherein the surgical hub control algorithms are updated based on the information related to at least one of compiled steps-of-use or procedure planning.

5. The surgical hub of claim 1, wherein the processor is further configured to:

based on the first connectivity mode not supporting communication with the cloud computing system, disable communication with the cloud computing system.

6. The surgical hub of claim 1, wherein the connectivity control parameter includes a purchased subscription level.

7. The surgical hub of claim 1, wherein the connectivity control parameter includes at least one of hardware capability, firmware capability, or software capability.

8. The surgical hub of claim 1, wherein the connectivity control parameter includes available data bandwidth, power capacity and usage, processor and memory utilization, or internal systems.

9. The surgical hub of claim 1, wherein the connectivity control parameter includes an indication from a tiered system.

10. The surgical hub of claim 9, wherein the tiered system scales communication between the surgical hub, the at least one surgical instrument, and the cloud computing system.

11. The surgical hub of claim 9, wherein the tiered system determines maximum communication capabilities the surgical hub operates under.

12. The surgical hub of claim 1, wherein:

the first connectivity mode is associated with a first service tier, the second connectivity mode is associated with a second service tier, and the third connectivity mode is associated with a third service tier, and the second service tier is updated from the first service tier and the third service tier is updated from the second service tier.

13. A surgical instrument operating within a surgical system, the surgical instrument comprising:

a transmitter and a receiver configured to establish a communication pathway between the surgical instrument and a cloud computing system and a communication pathway between the surgical instrument and a surgical hub; and a processor configured to:

determine, via the surgical hub, to operate in a connectivity mode of a plurality of connectivity modes based on a connectivity control parameter;

based on a determination to operate in a first connectivity mode of the plurality of connectivity modes, enable uni-directional communication with the cloud computing system and the surgical hub;

based on uni-directional communication with the surgical hub being enabled, send surgical information to the surgical hub;

based on a determination to operate in a second connectivity mode of the plurality of connectivity modes, enable bi-directional communication with the cloud computing system and the surgical hub;

based on bi-directional communication with the cloud computing system being enabled, send, to the cloud computing system, an aggregation analysis request, wherein the aggregation analysis request includes a request for aggregated data;

receive, in response to the aggregate analysis request via the cloud computing system, the aggregated data determined from multiple surgical sites;

update one or more surgical instrument control algorithms based on the aggregated data received;

based on bi-directional communication with the cloud computing system and the surgical hub being enabled, combine sensed surgical data within the surgical system with the aggregated data to display content on a display within the surgical system;

based on a determination to operate in a third connectivity mode of the plurality of connectivity modes, enable interactive communication with the cloud computing system and the surgical hub;

based on interactive communication with the cloud computing system being enabled, send, to the cloud computing system, a surgical recommendation request;

receive, in response to the surgical recommendation request via the cloud computing system, a surgical recommendation based on the aggregated data determined from the multiple surgical sites; and continue to communicate with the cloud computing system to receive additional updates, wherein the additional updates relate to updated aggregate data determined by the cloud computing system.

14. The surgical instrument of claim 13, wherein the processor is further configured to:

determine trends in at least one of outcomes, usage, or products from the aggregated data, wherein the surgical instrument control algorithms are updated based on the trends.

15. The surgical instrument of claim 13, wherein the processor is further configured to:

determine information related to at least one of setup, EMR information, procedure information, or product mix usage based on the aggregated data, wherein the surgical instrument control algorithms are updated based on the information related to at least one of setup, EMR information, procedure information, or product mix usage.

16. The surgical instrument of claim 13, wherein the processor is further configured to:

determine information related to at least one of compiled steps-of-use or procedure planning based on the aggregated data, wherein the surgical instrument control algorithms are updated based on the information related to at least one of compiled steps-of-use or procedure planning.

17. The surgical instrument of claim 13, wherein the processor is further configured to:

based on the first connectivity mode not supporting communication with the cloud computing system, disable communication with the cloud computing system.

18. The surgical instrument of claim 13, wherein:

the first connectivity mode is associated with a first service tier, the second connectivity mode is associated with a second service tier, and the third connectivity mode is associated with a third service tier, and the second service tier is updated from the first service tier and the third service tier is updated from the second service tier.

19. A surgical system, comprising:

a cloud computing system configured to aggregate data from multiple surgical devices;

a surgical hub, comprising:

a transmitter and a receiver configured to establish a communication pathway between the surgical hub and the cloud computing system;

a processor configured to:

determine to operate in a connectivity mode of a plurality of connectivity modes based on a connectivity control parameter;

based on a determination to operate in a first connectivity mode of the plurality of connectivity modes, enable uni-directional communication with the cloud computing system and one or more surgical instruments;

based on uni-directional communication with the one or more surgical instruments being enabled, receive surgical information from the one or more surgical instruments;

based on a determination to operate in a second connectivity mode of the plurality of connectivity modes, enable bi-directional communication with the cloud computing system and the one or more surgical instruments;

based on bi-directional communication with the cloud computing system being enabled, send, to the cloud computing system, an aggregation analysis request, wherein the aggregation analysis request includes a request for aggregated data;

receive, in response to the aggregate analysis request via the cloud computing system, the aggregated data determined from the multiple surgical sites;

update one or more surgical hub control algorithms based on the aggregated data received;

based on bi-directional communication with the cloud computing system and the one or more surgical instruments being enabled, infer progression of a surgical procedure from the aggregated data;

based on the inferred progression of the surgical procedure, generate instructional information;

send the instructional information to at least one surgical instrument operating within the surgical system;

based on a determination to operate in a third connectivity mode of the plurality of connectivity modes, enable interactive communication with the cloud computing system and the one or more surgical instruments;

based on interactive communication with the cloud computing system being enabled, send, to the cloud computing system, a surgical recommendation request;

receive, in response to the surgical recommendation request via the cloud computing system, a surgical recommendation based on the aggregated data determined from the multiple surgical sites; and continue to communicate with the cloud computing system to receive additional updates, wherein the additional updates relate to updated aggregate data determined by the cloud computing system; and a surgical instrument, comprising:

a transmitter and a receiver configured to establish a communication pathway between the surgical instrument and the surgical hub;

a processor configured to:

receive, via the surgical hub, the instructional information; and based on bi-directional communication with the cloud computing system and the surgical hub being enabled, combine sensed surgical data within the surgical system with the aggregated data to display content on a display within the surgical system.

20. The surgical system of claim 19, wherein:

the first connectivity mode is associated with a first service tier, the second connectivity mode is associated with a second service tier, and the third connectivity mode is associated with a third service tier, and the second service tier is updated from the first service tier and the third service tier is updated from the second service tier.

\* \* \* \* \*